(12) United States Patent
Xu et al.

(10) Patent No.: US 10,374,863 B2
(45) Date of Patent: Aug. 6, 2019

(54) APPARATUS, SYSTEMS AND METHODS FOR EVENT RECOGNITION BASED ON A WIRELESS SIGNAL

(71) Applicant: ORIGIN WIRELESS, INC., Greenbelt, MD (US)

(72) Inventors: Qinyi Xu, College Park, MD (US); Feng Zhang, Greenbelt, MD (US); Chen Chen, Burlingame, CA (US); Beibei Wang, Clarksville, MD (US); Chenshu Wu, Greenbelt, MD (US); Hangfang Zhang, Greenbelt, MD (US); Chau-Wai Wong, Raleigh, NC (US); David N. Claffey, Somerville, MA (US); Chun-I Chen, Brookeville, MD (US); Hung-Quoc Duc Lai, Parkville, MD (US); Zhung-Han Wu, College Park, MD (US); Min Wu, Clarksville, MD (US); Yi Han, Ellicott City, MD (US); Oscar Chi-Lim Au, San Jose, CA (US); K. J. Ray Liu, Potomac, MD (US)

(73) Assignee: ORIGIN WIRELESS, INC., Greenbelt, MD (US)

( * ) Notice: Subject to any disclaimer, the term of this patent is extended or adjusted under 35 U.S.C. 154(b) by 0 days.

(21) Appl. No.: 16/203,299

(22) Filed: Nov. 28, 2018

(65) Prior Publication Data

US 2019/0097865 A1   Mar. 28, 2019

Related U.S. Application Data

(63) Continuation-in-part of application No. 15/326,112, filed as application No. PCT/US2015/041037 on Jul.
(Continued)

(51) Int. Cl.
*H04L 27/36* (2006.01)
*H04W 72/04* (2009.01)
*H04B 1/38* (2015.01)

(52) U.S. Cl.
CPC ............ *H04L 27/362* (2013.01); *H04B 1/38* (2013.01); *H04W 72/0413* (2013.01)

(58) Field of Classification Search
CPC .................................................. H04L 27/362
See application file for complete search history.

(56) References Cited

U.S. PATENT DOCUMENTS 9,078,153 B1 * 7/2015 Schelstraete .......... H04W 88/08
9,119,236 B1   8/2015 Martin
(Continued)

FOREIGN PATENT DOCUMENTS

EP   3387849 A1   10/2018
EP   3426137 A1   1/2019
(Continued)

OTHER PUBLICATIONS

M. Spadacini et al., "Wireless networks for smart surveillance: Technologies, protocol design and experiments", 2012 IEEE Wireless Communications and Networking Conference Workshops (WCNCW), 2012, pp. 214-219, Paris.
(Continued)

*Primary Examiner* — Kevin M Cunningham
(74) *Attorney, Agent, or Firm* — Yingxin Xiao

(57) ABSTRACT

Apparatus, systems and methods for recognizing and classifying events in a venue based on a wireless signal are disclosed. In one example, a disclosed system comprises a first transmitter, a second transmitter, at least one first receiver, at least one second receiver, and an event recognition engine, in the venue. The first transmitter transmits a training wireless signal through a wireless multipath channel
(Continued)

impacted by a known event in the venue in a training time period associated with the known event. Each first receiver receives asynchronously the training wireless signal, and obtains, asynchronously based on the training wireless signal, at least one time series of training channel information of the wireless multipath channel between the first receiver and the first transmitter. The second transmitter transmits a current wireless signal through the wireless multipath channel impacted by a current event in a current time period associated with the current event. Each second receiver receives asynchronously the current wireless signal, and obtains, asynchronously based on the current wireless signal, at least one time series of current channel information of the wireless multipath channel between the second receiver and the second transmitter. The event recognition engine trains a classifier based on the training channel information; and apples the classifier to: classify the current channel information and associate the current event with at least one of: a known event, an unknown event and another event.

30 Claims, 25 Drawing Sheets

Related U.S. Application Data 17, 2015, which is a continuation-in-part of application No. 14/605,611, filed on Jan. 26, 2015, now Pat. No. 10,168,414, application No. 16/203,299, which is a continuation-in-part of application No. 15/584,052, filed on May 2, 2017, and a continuation-in-part of application No. 15/434,813, filed on Feb. 16, 2017, now Pat. No. 10,129,862, and a continuation-in-part of application No. PCT/US2017/021963, filed on Mar. 10, 2017, and a continuation-in-part of application No. PCT/US2017/021957, filed on Mar. 10, 2017, and a continuation-in-part of application No. PCT/US2017/027131, filed on Apr. 12, 2017, and a continuation-in-part of application No. 15/384,217, filed on Dec. 19, 2016, which is a continuation-in-part of application No. 13/706,342, filed on Dec. 5, 2012, now Pat. No. 9,883,511, and a continuation-in-part of application No. 13/969,271, filed on Aug. 16, 2013, now Pat. No. 9,882,675, and a continuation-in-part of application No. 13/969,320, filed on Aug. 16, 2013, now Pat. No. 9,559,874, and a continuation-in-part of application No. 15/041,677, filed on Feb. 11, 2016, now Pat. No. 9,794,156, and a continuation-in-part of application No. 15/200,430, filed on Jul. 1, 2016, now Pat. No. 9,736,002, which is a continuation of application No. 14/262,153, filed on Apr. 25, 2014, now Pat. No. 9,407,306, said application No. 15/384,217 is a continuation-in-part of application No. 15/200,429, filed on Jul. 1, 2016, now Pat. No. 9,781,700, which is a continuation of application No. 14/943,648, filed on Nov. 17, 2015, now Pat. No. 9,402,245, which is a continuation of application No. 14/202,651, filed on Mar. 10, 2014, now Pat. No. 9,226,304, said application No. 15/384,217 is a continuation-in-part of application No. 14/605,611, filed on Jan. 26, 2015, now Pat. No. 10,168,414, and a continuation-in-part of application No. 14/615,984, filed on Feb. 6, 2015, now Pat. No. 9,686,054, and a continuation-in-part of application No. 15/004,314, filed on Jan. 22, 2016, now Pat. No. 10,014,982, and a continuation-in-part of application No. 15/061,059, filed on Mar. 4, 2016, and a continuation-in-part of application No. PCT/US2015/041037, filed on Jul. 17, 2015, which is a continuation-in-part of application No. 14/605,611, filed on Jan. 26, 2015, now Pat. No. 10,168,414, said application No. 15/384,217 is a continuation-in-part of application No. 15/268,477, filed on Sep. 16, 2016, now Pat. No. 9,887,864, which is a continuation-in-part of application No. 15/200,429, filed on Jul. 1, 2016, now Pat. No. 9,781,700, which is a continuation of application No. 14/943,648, filed on Nov. 17, 2015, now Pat. No. 9,402,245, which is a continuation of application No. 14/202,651, filed on Mar. 10, 2014, now Pat. No. 9,226,304, said application No. 15/384,217 is a continuation-in-part of application No. 15/284,496, filed on Oct. 3, 2016, and a continuation-in-part of application No. PCT/US2016/066015, filed on Dec. 9, 2016, application No. 16/203,299, which is a continuation-in-part of application No. PCT/US2017/015909, filed on Jan. 31, 2017, which is a continuation-in-part of application No. PCT/US2016/066015, filed on Dec. 9, 2016, application No. 16/203,299, which is a continuation-in-part of application No. 15/861,422, filed on Jan. 3, 2018, and a continuation-in-part of application No. 15/873,806, filed on Jan. 17, 2018, now Pat. No. 10,270,642, and a continuation-in-part of application No. 16/101,444, filed on Aug. 11, 2018, now Pat. No. 10,291,460, which is a continuation-in-part of application No. 16/200,608, filed on Nov. 26, 2018, which is a continuation-in-part of application No. 16/200,616, filed on Nov. 26, 2018.

(60) Provisional application No. 62/148,019, filed on Apr. 15, 2015, provisional application No. 62/025,795, filed on Jul. 17, 2014, provisional application No. 62/069,090, filed on Oct. 27, 2014, provisional application No. 62/331,278, filed on May 3, 2016, provisional application No. 62/295,970, filed on Feb. 16, 2016, provisional application No. 62/320,962, filed on Apr. 11, 2016, provisional application No. 62/307,081, filed on Mar. 11, 2016, provisional application No. 62/316,850, filed on Apr. 1, 2016, provisional application No. 62/307,172, filed on Mar. 11, 2016, provisional application No. 62/334,110, filed on May 10, 2016, provisional application No. 62/322,575, filed on Apr. 14, 2016, provisional application No. 62/409,796, filed on Oct. 18, 2016, provisional application No. 62/593,826, filed on Dec. 1, 2017, provisional application No. 62/106,395, filed on Jan. 22, 2015, provisional application No. 62/128,574, filed on Mar. 5, 2015, provisional application No. 62/219,315, filed on Sep. 16, 2015, provisional application No. 62/235,958, filed on Oct. 1, 2015, provisional application No. 62/265,155, filed on Dec. 9, 2015, provisional application No. 62/411,504, filed on Oct. 21, 2016, provisional application No. 62/383,235, filed on Sep. 2, 2016, provisional application No. 62/307,081, filed on Mar. 11, 2016, provisional application No. 62/316,850, filed on Apr. 1, 2016, provisional application No. 62/320,965, filed on Apr. 11, 2016, provisional application No. 62/384,060, filed on Sep. 6, 2016, provisional application No. 62/678,207, filed on May 30, 2018, provisional application No. 62/734,224, filed on Sep. 20, 2018, provisional application No.

62/744,093, filed on Oct. 10, 2018, provisional application No. 62/753,017, filed on Oct. 30, 2018.

(56) References Cited

U.S. PATENT DOCUMENTS

| | | | |
|---|---|---|---|
| 9,413,580 | B2 | 8/2016 | Dhayni |
| 9,753,796 | B2 | 9/2017 | Mahaffey et al. |
| 2012/0077468 | A1 | 3/2012 | Fan et al. |
| 2014/0266669 | A1 | 9/2014 | Fadell et al. |
| 2015/0163121 | A1 | 6/2015 | Mahaffey et al. |
| 2015/0256379 | A1 | 9/2015 | Dhayni et al. |
| 2016/0018508 | A1 | 1/2016 | Chen et al. |
| 2017/0212210 | A1 | 7/2017 | Chen et al. |
| 2018/0183650 | A1 | 6/2018 | Zhang et al. |
| 2018/0306609 | A1* | 10/2018 | Agarwal .................. H04L 67/12 |
| 2018/0351775 | A1 | 12/2018 | Zhang et al. |
| 2018/0357542 | A1* | 12/2018 | Wu .......................... G06N 3/08 |
| 2018/0365975 | A1 | 12/2018 | Xu et al. |
| 2019/0007256 | A1 | 1/2019 | Chen et al. |
| 2019/0028320 | A1 | 1/2019 | Xu et al. |

FOREIGN PATENT DOCUMENTS

| | | |
|---|---|---|
| WO | 2016/011433 A2 | 1/2016 |
| WO | 2017/100706 A1 | 6/2017 |
| WO | 2017/156487 A1 | 9/2017 |
| WO | 2017/156492 A1 | 9/2017 |
| WO | 2017/180698 A1 | 10/2017 |

OTHER PUBLICATIONS

Zimu Zhou et al., "On Muitipath Link Characterization and Adaptation for Device-Free Human Detection", 2015 IEEE 35th International Conference on Distributed Computing Systems, 2015, pp. 389-398, Columbus, OH.

Bo Tan et al., "Wi-Fi based passive human motion sensing for in-home healthcare applications", 2015 IEEE 2nd World Forum on Internet of Things (WF-IoT), 2015, pp. 609-614, Milan.

Jiang Mao et al., "FIMD: Fine-grained Device-free Motion Detection", 2012 IEEE 18th International Conference on Parallel and Distributed Systems, 2012, pp. 229-235, Singapore.

Na Pang et al., "WarnFi: Non-invasive wili-based abnormal activity sensing using non-parametric model", MILCOM 2017—2017 IEEE Military Communications Conference (MILCOM), 2017, pp. 800-805, Baltimore, MD.

Qin Yi Xu et al., "Statistical Learning Over Time-Reversal Space for Indoor Monitoring System", IEEE Internet of Things Journal, Apr. 2018, pp. 970-983, vol. 5, No. 2.

Qinyi Xu et al, "TRIEDS: Wireless Events Detection Through the Wall", IEEE Internet of Things Journal, Jun. 2017, pp. 723-735, vol. 4, No. 3.

Mohammed Abdulaziz Aide Al-Qaness et al., "Device-free home intruder detection and alarm system using WiFi channel state information", International Journal of Future Computer and Communication, Aug. 2016, pp. 180-186, vol. 5, No. 4.

Kazuya Ohara et al., "Detecting state changes of indoor everyday objects using Wi-Fi channel state information", Proceedings of the ACM on Interactive, Mobile, Wearable and Ubiquitous Technologies, Sep. 2017, pp. 88:1-88:28, vol. 1, No. 3, Article 88.

Thilina Dissanayake et al., "Detecting Door Events Using a Smartphone via Active Sound Sensing", Proc. ACM Interact. Mob. Wearable Ubiquitous Technol., Dec. 2018, pp. 160:1-160:26, vol. 2, No. 4, Article 160.

Yu Gu et al., "PAWS: Passive human activity recognition based on WiFi ambient signals", IEEE Internet of Things Journal, Oct. 2016, pp. 796-805, vol. 3, No. 5.

Chenshu Wu et al., "Non-invasive detection of moving and stationary human with WiFi", IEEE Journal on Selected Areas in Communications, Nov. 2015, pp. 2329-2342, vol. 33, No. 11.

Yunze Zeng et al., "Your AP knows how you move: fine-grained device motion recognition through WiFi", Proceedings of the 1st ACM workshop on Hot topics in wireless, 2014, pp. 49-54.

Sevgi Zubeyde Gurbuz et al., "Micro-Doppler-based in-home aided and unaided walking recognition with multiple radar and sonar systems", IET Radar, Sonar & Navigation, Apr. 2017, pp. 107-115, vol. 11, No, 1.

Fadel Adib et al., "See through walls with WiFi!", ACM SIGCOMM Computer Communication Review, Aug. 2013, pp. 75-86, vol. 43.

Fadel Adib et al., "3D tracking via body radio reflections", The 11th USENIX Symposium on Networked Systems Design and Implementation, USENIX Association, 2014, pp. 317-329.

Jiguang LV et al., "Robust wlan-based indoor fine-grained intrusion detection", IEEE Global Communications Conference (GLOBECOM), IEEE, 2016, pp. 1-6.

Tong Xin et al., "Freesense: A robust approach for indoor human detection using wi-fi signals", Proc. ACM Interact. Mob. Wearable Ubiquitous Technol., Sep. 2018, pp. 143:1-143:23, vol. 2, No. 3, Article 143.

Feng Zhang et al., "Wispeed: A statistical electromagnetic approach for device-free indoor speed estimation", IEEE Internet of Things Journal, Jun. 2018, pp. 2163-2177, vol. 5, No. 3.

Yu Gu et al., "MoSense: An RF-Based Motion Detection System via Off-the-Shelf WiFi Devices", IEEE Internet of Things Journal, Dec. 2017, pp. 2326-2341, vol. 4, No. 6.

Christian Siebert et al., "Human Motion Detection and Classification Using Ambient WiFi Signals", 2017 Sensor Signal Processing for Defence Conference (SSPD), 2017, pp. 1-5, London.

Kun Qian et al, "Enabling contactless detection of moving humans with dynamic speeds using csi," ACM Transactions on Embedded Computing Systems, Jan. 2018, pp. 52:1-52:18, vol. 17, No. 2, Article 52.

* cited by examiner

APPARATUS, SYSTEMS AND METHODS FOR EVENT RECOGNITION BASED ON A WIRELESS SIGNAL

CROSS-REFERENCE TO RELATED APPLICATIONS

The present application hereby claims priority to, and incorporates by reference the entirety of the disclosures of, each of the following applications:
(a) U.S. patent application Ser. No. 15/326,112, entitled "WIRELESS POSITIONING SYSTEMS", filed on Jan. 13, 2017,
  (1) which is a national stage entry of PCT patent application PCT/US2015/041037, entitled "WIRELESS POSITIONING SYSETMS", filed on Jul. 17, 2015, published as WO 2016/011433A2 on Jan. 21, 2016,
    a. which claims priority to U.S. Provisional patent application 62/148,019, entitled "WIRELESS POSITIONING SYSTEMS", filed on Apr. 15, 2015,
    b. which is a continuation-in-part of U.S. patent application Ser. No. 14/605,611, entitled "WIRELESS POSITIONING SYSTEMS", filed on Jan. 26, 2015, published as US2016/0018508A1 on Jan. 21, 2016,
      1. which claims priority to U.S. Provisional patent application 62/025,795, entitled "TIME-REVERSAL POSITIONING SYSTEMS", filed on Jul. 17, 2014, and
      2. which claims priority to U.S. Provisional patent application 62/069,090, entitled "TIME-REVERSAL POSITIONING SYSTEMS", filed on Oct. 27, 2014,
(b) U.S. patent application Ser. No. 15/584,052, entitled "METHOD, SYSTEM, AND APPARATUS FOR WIRELESS POWER TRANSMISSION BASED ON POWER WAVEFORMING", filed on May 2, 2017,
  (1) which claims priority to U.S. Provisional patent application 62/331,278, entitled "USING VIRTUAL ANTENNAS FOR POWER WAVEFORMING IN WIRELESS POWER TRANSMISSION SYSTEMS", filed on May 3, 2016,
(c) U.S. patent application Ser. No. 15/434,813, entitled "METHODS, DEVICES, APPARATUS, AND SYSTEMS FOR MEDIUM ACCESS CONTROL IN WIRELESS COMMUNICATION SYSTEMS UTILIZING SPATIAL FOCUSING EFFECT", filed on Feb. 16, 2017,
  (1) which claims priority to U.S. Provisional patent application 62/295,970, entitled "THE IMPACT OF SPATIAL FOCUSING EFFECTS ON MEDIUM ACCESS CONTROL DESIGN FOR 5G", filed on Feb. 16, 2016,
  (2) which claims priority to U.S. Provisional patent application 62/320,965, entitled "OPTIMAL RATE ADAPTATION FOR THROUGHPUT MAXIMIZATION IN TIME REVERSAL DIVISION MULTIPLE ACCESS", filed on Apr. 11, 2016,
(d) PCT patent application PCT/US2017/021963, entitled "METHODS, APPARATUS, SERVERS, AND SYSTEMS FOR VITAL SIGNS DETECTION AND MONITORING", filed on Mar. 10, 2017, published as WO2017/156492A1 on Sep. 14, 2017,
  (1) which claims priority to U.S. Provisional patent application 62/307,081, entitled "TR-BREATH: TIME-REVERSAL BREATHING RATE ESTIMATION AND DETECTION", filed on Mar. 11, 2016,
  (2) which claims priority to U.S. Provisional patent application 62/316,850, entitled "TR-BREATH: TIME-REVERSAL BREATHING RATE ESTIMATION AND DETECTION", filed on Apr. 1, 2016,
(e) PCT patent application PCT/US2017/021957, entitled "METHODS, APPARATUS, SERVERS, AND SYSTEMS FOR HUMAN IDENTIFICATION BASED ON HUMAN RADIO BIOMETRIC INFORMATION", filed on Mar. 10, 2017, published as WO2017/156487A1 on Sep. 14, 2017,
  (1) which claims priority to U.S. Provisional patent application 62/307,172, entitled "RADIO SHOT: THROUGH-THE-WALL HUMAN IDENTIFICATION", filed on Mar. 11, 2016,
  (2) which claims priority to U.S. Provisional patent application 62/334,110, entitled "TIME-REVERSAL TRACKING WITHOUT MAPPING", filed on May 10, 2016,
(f) PCT patent application PCT/US2017/027131, entitled "METHODS, APPARATUS, SERVERS, AND SYSTEMS FOR OBJECT TRACKING", filed on Apr. 12, 2017, published as WO2017/180698A1 on Oct. 19, 2017,
  (1) which claims priority to U.S. Provisional patent application 62/322,575, entitled "TIME-REVERSAL RESONATING EFFECT AND ITS APPLICATION IN WALKING SPEED ESTIMATION", filed on Apr. 14, 2016,
  (2) which claims priority to U.S. Provisional patent application 62/334,110, entitled "TIME-REVERSAL TRACKING WITHOUT MAPPING", filed on May 10, 2016, and
  (3) which claims priority to U.S. Provisional patent application 62/409,796, entitled "METHODS, DEVICES, SERVERS, AND SYSTEMS OF TIME REVERSAL BASED TRACKING", filed on Oct. 18, 2016,
(g) U.S. Provisional patent application 62/557,117, entitled "METHODS, DEVICES, SERVERS, APPARATUS, AND SYSTEMS FOR WIRELESS INTERNET OF THINGS APPLICATIONS", filed on Sep. 11, 2017,
(h) U.S. Provisional patent application 62/593,826, entitled "METHOD, APPARATUS, AND SYSTEM FOR OBJECT TRACKING AND NAVIGATION", filed on Dec. 1, 2017,
(i) U.S. patent application Ser. No. 15/384,217, entitled "METHOD, APPARATUS, SERVER, AND SYSTEMS OF TIME-REVERSAL TECHNOLOGY", filed on Dec. 19, 2016, published as US2017/0188359A1 on Jun. 29, 2017,
  (1) which is a Continuation-in-Part of U.S. patent application Ser. No. 13/706,342, entitled "WAVEFORM DESIGN FOR TIME-REVERSAL SYSTEMS," filed on Dec. 5, 2012, issued as U.S. Pat. No. 9,883,511 on Jan. 30, 2018,
  (2) which is a Continuation-in-Part of U.S. patent application Ser. No. 13/969,271, entitled "TIME-REVERSAL WIRELESS SYSTEMS HAVING ASYMMETRIC ARCHITECTURE", filed on Aug. 16, 2013, published as US2015/0049745A1 on Feb. 19, 2015, issued as U.S. Pat. No. 9,882,675 on Jan. 30, 2018,
  (3) which is a Continuation-in-Part of U.S. patent application Ser. No. 13/969,320, entitled "MUL- TIUSER TIME-REVERSAL DIVISION MULTIPLE ACCESS UPLINK SYSTEM WITH PARALLEL INTERFERENCE CANCELLATION", filed on Aug. 16, 2013, issued as U.S. Pat. No. 9,559,874 on Jan. 31, 2017, (4) which is a Continuation-in-Part of U.S. patent application Ser. No. 15/041,677, entitled "HANDSHAKING PROTOCOL FOR TIME-REVERSAL SYSTEM", filed on Feb. 11, 2016, published as US2016/0164669A1 on Jun. 9, 2016, issued as U.S. Pat. No. 9,794,156 on Oct. 17, 2017, (5) which is a Continuation-in-Part of U.S. patent application Ser. No. 15/200,430, entitled "QUADRATURE AMPLITUDE MODULATION FOR TIME-REVERSAL SYSTEMS", filed on Jul. 1, 2016, published as US2016/0315797A1 on Oct. 27, 2016, issued as U.S. Pat. No. 9,736,002 on Aug. 15, 2017,
   a. which is a Continuation of U.S. patent application Ser. No. 14/262,153, entitled "QUADRATURE AMPLITUDE MODULATION FOR TIME-REVERSAL SYSTEMS", filed on Apr. 25, 2014, issued as U.S. Pat. No. 9,407,306 on Aug. 2, 2016, (6) which is a Continuation-in-Part of U.S. patent application Ser. No. 15/200,429, entitled "TIME-REVERSAL WIRELESS PARADIGM FOR INTERNET OF THINGS", filed on Jul. 1, 2016, issued as U.S. Pat. No. 9,781,700 on Oct. 3, 2017,
   a. which is a Continuation of U.S. patent application Ser. No. 14/943,648, entitled "TIME-REVERSAL WIRELESS PARADIGM FOR INTERNET OF THINGS", filed on Nov. 17, 2015, issued as U.S. Pat. No. 9,402,245 on Jul. 26, 2016,
      1. which is a Continuation of U.S. patent application Ser. No. 14/202,651, entitled "TIME-REVERSAL WIRELESS PARADIGM FOR INTERNET OF THINGS", filed on Mar. 10, 2014, issued as U.S. Pat. No. 9,226,304 on Dec. 29, 2015, (7) which is a Continuation-in-Part of U.S. patent application Ser. No. 14/605,611, entitled "WIRELESS POSITIONING SYSTEM", filed on Jan. 26, 2015, published as US2016/0018508A1 on Jan. 21, 2016,
   a. which claims priority to U.S. Provisional patent application 62/069,090, entitled "TIME-REVERSAL POSITIONING SYSTEMS", filed on Oct. 27, 2014,
   b. which claims priority to U.S. Provisional patent application 62/025,795, entitled "TIME-REVERSAL POSITIONING SYSTEMS", filed on Jul. 17, 2014, (8) which is a Continuation-in-Part of U.S. patent application Ser. No. 14/615,984, entitled "JOINT WAVEFORM DESIGN AND INTERFERENCE PRE-CANCELLATION FOR TIME-REVERSAL SYSTEMS", filed on Feb. 6, 2015, issued as U.S. Pat. No. 9,686,054 on Jun. 20, 2017,
   a. which claims priority to U.S. Provisional patent application 62/025,795, entitled "TIME-REVERSAL POSITIONING SYSTEMS", filed on Jul. 17, 2014, (9) which is a Continuation-in-Part of U.S. patent application Ser. No. 15/004,314, entitled "TIME-REVERSAL TECHNOLOGIES FOR HYBRID WIRELESS NETWORKS", filed on Jan. 22, 2016, issued as U.S. Pat. No. 10,014,982 on Jul. 3, 2018,
   a. which claims priority to U.S. Provisional patent application 62/106,395, entitled "TIME-REVERSAL TECHNOLOGIES FOR HYBRID WIRELESS NETWORKS", filed on Jan. 22, 2015,

(10) which is a Continuation-in-Part of U.S. patent application Ser. No. 15/061,059, entitled "TIME-REVERSAL SCALABILITY FOR HIGH NETWORK DENSIFICATION", filed on Mar. 4, 2016,
   a. which claims priority to U.S. Provisional patent application 62/128,574, entitled "TIME-REVERSAL SCALABILITY FOR HIGH NETWORK DENSIFICATION", filed on Mar. 5, 2015,

(11) which is a Continuation-in-Part of PCT patent application PCT/US2015/041037, entitled "WIRELESS POSITIONING SYSTEMS", filed on Jul. 17, 2015, published as WO2016/011433A2 on Jan. 21, 2016,
   a. which claims priority to U.S. Provisional patent application 62/148,019, entitled "WIRELESS POSITIONING SYSTEMS", filed on Apr. 15, 2015,
   b. which is a continuation-in-part of U.S. patent application Ser. No. 14/605,611, entitled "WIRELESS POSITIONING SYSTEMS", filed on Jan. 26, 2015, published as US2016/0018508A1 on Jan. 21, 2016,
      1. which claims priority to U.S. Provisional patent application 62/025,795 entitled "TIME-REVERSAL POSITIONING SYSTEMS", filed on Jul. 17, 2014, and
      2. which claims priority to U.S. Provisional patent application 62/069,090 entitled "TIME-REVERSAL POSITIONING SYSTEMS", filed on Oct. 27, 2014,

(12) which is a Continuation-in-Part of U.S. patent application Ser. No. 15/268,477, entitled "METHODS, DEVICES AND SYSTEMS OF HETEROGENEOUS TIME-REVERSAL PARADIGM ENABLING DIRECT CONNECTIVITY IN INTERNET OF THINGS", filed on Sep. 16, 2016, issued as U.S. Pat. No. 9,887,864 on Feb. 6, 2018,
   a. which claims priority to U.S. Provisional patent application 62/219,315, entitled "ENABLING DIRECT CONNECTIVITY IN INTERNET OF THINGS: A HETEROGENEOUS TIME-REVERSAL PARADIGM", filed on Sep. 16, 2015,
   b. which is a Continuation-in-part of U.S. patent application Ser. No. 15/200,429, entitled "TIME-REVERSAL WIRELESS PARADIGM FOR INTERNET OF THINGS", filed on Jul. 1, 2016, issued as U.S. Pat. No. 9,781,700 on Oct. 3, 2017,
      1. which is a Continuation of U.S. patent application Ser. No. 14/943,648, entitled "TIME-REVERSAL WIRELESS PARADIGM FOR INTERNET OF THINGS", filed on Nov. 17, 2015, issued as U.S. Pat. No. 9,402,245 on Jul. 26, 2016,
         i. which is a Continuation of U.S. patent application Ser. No. 14/202,651, entitled "TIME-REVERSAL WIRELESS PARADIGM FOR INTERNET OF THINGS", filed on Mar. 10, 2014, issued as U.S. Pat. No. 9,226,304 on Dec. 29, 2015,

(13) which is a Continuation-in-Part of U.S. patent application Ser. No. 15/284,496, entitled "TIME-REVERSAL COMMUNICATION SYSTEMS", filed on Oct. 3, 2016, a. which claims priority to U.S. Provisional patent application 62/235,958, entitled "SYMBOL TIMING FOR TIME-REVERSAL SYSTEMS WITH SIGNATURE DESIGN", filed on Oct. 1, 2015,
(14) which is a Continuation-in-Part of
PCT patent application PCT/US2016/066015, entitled "METHOD, APPARATUS, AND SYSTEMS FOR WIRELESS EVENT DETECTION AND MONITORING", filed on Dec. 9, 2016, published as WO2017/100706A1 on Jun. 15, 2017, whose US national stage entry is Ser. No. 16/060,710, filed on Jun. 8, 2018,
  a. which claims priority to U.S. Provisional patent application 62/265,155, entitled "INDOOR EVENTS DETECTION SYSTEM", filed on Dec. 9, 2015,
  b. which claims priority to U.S. Provisional patent application 62/411,504, entitled "METHOD, APPARATUS, AND SYSTEM FOR WIRELESS INTERNET OF THINGS APPLICATIONS", filed on Oct. 21, 2016,
  c. which claims priority to U.S. Provisional patent application 62/383,235, entitled "TIME REVERSAL MONITORING SYSTEM", filed on Sep. 2, 2016,
  d. which claims priority to U.S. Provisional patent application 62/307,081, entitled "TR-BREATH: TIME-REVERSAL BREATHING RATE ESTIMATION AND DETECTION", filed on Mar. 11, 2016,
  e. which claims priority to U.S. Provisional patent application 62/316,850, entitled "TR-BREATH: TIME-REVERSAL BREATHING RATE ESTIMATION AND DETECTION", filed on Apr. 1, 2016,
(15) which claims priority to U.S. Provisional patent application 62/331,278, entitled "USING VIRTUAL ANTENNAS FOR POWER WAVEFORMING IN WIRELESS POWER TRANSMISSION SYSTEMS", filed on May 3, 2016,
(16) which claims priority to U.S. Provisional patent application 62/295,970, entitled "THE IMPACT OF SPATIAL FOCUSING EFFECTS ON THE MEDIUM ACCESS CONTROL DESIGN FOR 5G", filed on Feb. 16, 2016,
(17) which claims priority to U.S. Provisional patent application 62/320,965, entitled "OPTIMAL RATE ADAPTATION FOR THROUGHPUT MAXIMIZATION IN TIME REVERSAL DIVISION MULTIPLE ACCESS", filed on Apr. 11, 2016,
(18) which claims priority to U.S. Provisional patent application 62/307,081, entitled "TR-BREATH: TIME-REVERSAL BREATHING RATE ESTIMATION AND DETECTION", filed on Mar. 11, 2016,
(19) which claims priority to U.S. Provisional patent application 62/316,850, entitled "TR-BREATH: TIME-REVERSAL BREATHING RATE ESTIMATION AND DETECTION", filed on Apr. 1, 2016,
(20) which claims priority to U.S. Provisional patent application 62/307,172, entitled "RADIO SHOT: THROUGH-THE-WALL HUMAN IDENTIFICATION", filed on Mar. 11, 2016,
(21) which claims priority to U.S. Provisional patent application 62/322,575, entitled "TIME-REVERSAL RESONATING EFFECT AND ITS APPLICATION IN WALKING SPEED ESTIMATION", filed on Apr. 14, 2016,
(22) which claims priority to U.S. Provisional patent application 62/334,110, entitled "TIME-REVERSAL TRACKING WITHOUT MAPPING", filed on May 10, 2016,
(23) which claims priority to U.S. Provisional patent application 62/409,796, entitled "METHODS, DEVICES, SERVERS, AND SYSTEMS OF TIME REVERSAL BASED TRACKING", filed on Oct. 18, 2016,
(24) which claims priority to U.S. Provisional patent application 62/383,235, entitled "TIME REVERSAL MONITORING SYSTEM", filed on Sep. 2, 2016,
(25) which claims priority to U.S. Provisional patent application 62/384,060, entitled "METHODS, DEVICES, SERVERS, SYSTEMS OF TIME REVERSAL MACHINE PLATFORM FOR BROADBAND WIRELESS APPLICATIONS", filed on Sep. 6, 2016,
(26) which claims priority to U.S. Provisional patent application 62/411,504, entitled "METHOD, APPARATUS, AND SYSTEM FOR WIRELESS INTERNET OF THINGS APPLICATIONS", filed on Oct. 21, 2016,
(j) PCT patent application PCT/US2017/015909, entitled "METHODS, DEVICES, SERVERS, APPARATUS, AND SYSTEMS FOR WIRELESS INTERNET OF THINGS APPLICATIONS", filed on Jan. 31, 2017, published as WO2017/155634A1 on Sep. 14, 2017,
  (1) which claims priority to U.S. Provisional patent application 62/384,060, entitled "METHODS, DEVICES, SERVERS, SYSTEMS OF TIME REVERSAL MACHINE PLATFORM FOR BROADBAND WIRELESS APPLICATIONS", filed on Sep. 6, 2016,
  (2) which claims priority to U.S. Provisional patent application 62/331,278, entitled "USING VIRTUAL ANTENNAS FOR POWER WAVEFORMING IN WIRELESS POWER TRANSMISSION SYSTEMS", filed on May 3, 2016,
  (3) which claims priority to U.S. Provisional patent application 62/307,081, entitled "TR-BREATH: TIME-REVERSAL BREATHING RATE ESTIMATION AND DETECTION", filed on Mar. 11, 2016,
  (4) which claims priority to U.S. Provisional patent application 62/316,850, entitled "TR-BREATH: TIME-REVERSAL BREATHING RATE ESTIMATION AND DETECTION", filed on Apr. 1, 2016,
  (5) which claims priority to U.S. Provisional patent application 62/322,575, entitled "TIME-REVERSAL RESONATING EFFECT AND ITS APPLICATION IN WALKING SPEED ESTIMATION", filed on Apr. 14, 2016,
  (6) which claims priority to U.S. Provisional patent application 62/334,110, entitled "TIME-REVERSAL TRACKING WITHOUT MAPPING", filed on May 10, 2016,
  (7) which claims priority to U.S. Provisional patent application 62/409,796, entitled "METHODS, DEVICES, SERVERS, AND SYSTEMS OF TIME REVERSAL BASED TRACKING", filed on Oct. 18, 2016,
  (8) which claims priority to U.S. Provisional patent application 62/383,235, entitled "TIME REVERSAL MONITORING SYSTEM", filed on Sep. 2, 2016, (9) which claims priority to U.S. Provisional patent application 62/411,504, entitled "METHOD, APPARATUS, AND SYSTEM FOR WIRELESS INTERNET OF THINGS APPLICATIONS", filed on Oct. 21, 2016,

(10) which claims priority to U.S. Provisional patent application 62/307,172, entitled "RADIO SHOT: THROUGH-THE-WALL HUMAN IDENTIFICATION", filed on Mar. 11, 2016,

(11) which claims priority to PCT patent application PCT/US2016/066015, entitled "METHOD, APPARATUS, AND SYSTEMS FOR WIRELESS EVENT DETECTION AND MONITORING", filed on Dec. 9, 2016, published as WO2017/100706A1 on Jun. 15, 2017, whose US national stage entry is U.S. patent application Ser. No. 16/060,710, entitled "METHOD, APPARATUS, AND SYSTEMS FOR WIRELESS EVENT DETECTION AND MONITORING", filed on Jun. 8, 2018, (k) U.S. Provisional patent application 62/678,207, entitled "METHOD, APPARATUS, AND SYSTEM FOR OBJECT TRACKING AND MOTION MONITORING", filed on May 30, 2018, (l) U.S. patent application Ser. No. 15/861,422, entitled "METHOD, APPARATUS, SERVER, AND SYSTEMS OF TIME-REVERSAL TECHNOLOGY", filed on Jan. 3, 2018, (m) U.S. patent application Ser. No. 15/873,806, entitled "METHOD, APPARATUS, AND SYSTEM FOR OBJECT TRACKING AND NAVIGATION", filed on Jan. 17, 2018.

(n) U.S. patent application Ser. No. 16/101,444, entitled "METHOD, APPARATUS, AND SYSTEM FOR WIRELESS MOTION MONITORING", filed on Aug. 11, 2018.

(o) U.S. Provisional Patent application 62/734,224, entitled "METHOD, APPARATUS, AND SYSTEM FOR WIRELESS SLEEP MONITORING", filed on Sep. 20, 2018.

(p) U.S. Provisional Patent application 62/744,093, entitled "METHOD, APPARATUS, AND SYSTEM FOR WIRELESS PROXIMITY AND PRESENCE MONITORING", filed on Oct. 10, 2018.

(q) U.S. Provisional Patent application 62/753,017, entitled "METHOD, APPARATUS, AND SYSTEM FOR HUMAN IDENTIFICATION BASED ON HUMAN RADIO BIOMETRIC INFORMATION", filed on Oct. 30, 2018.

(r) U.S. patent application Ser. No. 16/200,608, entitled "METHOD, APPARATUS, SERVER AND SYSTEM FOR VITAL SIGN DETECTION AND MONITORING", filed on Nov. 26, 2018.

(s) U.S. patent application Ser. No. 16/200,616, entitled "METHOD, APPARATUS, SERVER AND SYSTEM FOR REAL-TIME VITAL SIGN DETECTION AND MONITORING", filed on Nov. 26, 2018.

TECHNICAL FIELD

The present teaching generally relates to event recognition and monitoring. More specifically, the present teaching relates to recognizing and classifying events in a venue based on a wireless signal.

BACKGROUND

Security systems are becoming increasingly prevalent for both public buildings and private dwellings. A conventional security system typically uses contact sensors that are monitored and/or controlled by a central panel that is usually mounted in the house. Various sensors can be installed at windows, doors, and other locations to detect intrusion, e.g. one sensor per door or window. A typical house (e.g. with a size of 1500 sqft) may need at least 6-8 sensors. This induces a considerable hardware cost. The installation of the conventional security system (especially the wiring) is tedious, time consuming and expensive. A conventional security system is very difficult, if not impossible, to upgrade, which is needed over time as technology develops. Maintenance and repair of a conventional security system are also tedious, expensive, and close to impossible.

In addition, existing security systems based on object motion detection cannot provide enough accuracy and often lead to false alarms. Existing approaches include those based on passive infrared (PIR), active infrared (AIR) and Ultrasonic. PIR sensors are the most widely used motion sensor in home security systems, and can detect human motions by sensing the difference between background heat and the heat emitted by moving people. However, systems based on PIR sensors are prone to false alarms due to its sensitivity to environmental changes, like hot/cold air flow and sunlight. They are easily defeated by blocking the body heat emission by e.g. wearing a heat-insulating full-body suit. Their range is limited and need a line-of-sight (LOS) condition; thus multiple devices are needed. In AIR based systems, an IR emitter sends a beam of IR which will be received by an IR receiver. When the beam is interrupted, a motion is detected. This solution can be easily seen using a regular camera or any IR detection mechanism and also has a limited range and thus needs LOS. Ultrasonic sensors detect human motion by sending out ultrasonic sound waves into a space and measuring the speed at which they return, and motion can be detected if there is a frequency change. But this approach can be defeated by wearing an anechoic suit. Also, ultrasound cannot penetrate solid objects such as furniture or boxes, which causes gaps in detection field. Slow movements by a burglar may not trigger an alarm in this case.

Therefore, there is a need for apparatus and methods for recognizing events (e.g. events related to object motion and/or security) to solve the above-mentioned problems and to avoid the above-mentioned drawbacks.

SUMMARY

The present teaching generally relates to periodic motion (e.g. human breathing) detection. More specifically, the present teaching relates to periodic motion detection and monitoring based on time-reversal technology in a rich-scattering wireless environment, such as an indoor environment or urban metropolitan area, enclosed environment, underground environment, open-air venue with barriers such as parking lot, storage, yard, square, forest, cavern, valley, etc.

In one embodiment, a method implemented on a machine having a processor, a memory communicatively coupled with the processor and a set of instructions stored in the memory for recognizing an event is disclosed. The method comprises: for each of at least one known event happening in a venue in a respective training time period: transmitting, by an antenna of a first transmitter, a respective training wireless signal to at least one first receiver through a wireless multipath channel impacted by the known event in the venue in the training time period associated with the known event, obtaining, asynchronously by each of the at least one first receiver based on the training wireless signal, at least one time series of training channel information (training CI time series) of the wireless multipath channel between the first receiver and the first transmitter in the training time period associated with the known event, and pre-processing the at least one training CI time series; training at least one classifier for the at least one known event based on the at least one training CI time series; and for a current event happening in the venue in a current time period, transmitting, by an antenna of a second transmitter, a current wireless signal to at least one second receiver through the wireless multipath channel impacted by the current event in the venue in the current time period associated with the current event, obtaining, asynchronously by each of the at least one second receiver based on the current wireless signal, at least one time series of current channel information (current CI time series) of the wireless multipath channel between the second receiver and the second transmitter in the current time period associated with the current event, pre-processing the at least one current CI time series, and applying the at least one classifier to: classify at least one of: the at least one current CI time series, a portion of a particular current CI time series, and a combination of the portion of the particular current CI time series and a portion of an additional CI time series, and associate the current event with at least one of: a known event, an unknown event and another event. A training CI time series associated with a first receiver and a current CI time series associated with a second receiver have at least one of: different starting times, different time durations, different stopping times, different counts of items in their respective time series, different sampling frequencies, different sampling periods between two consecutive items in their respective time series, and channel information (CI) with different features.

In another embodiment, a system having a processor, a memory communicatively coupled with the processor and a set of instructions stored in the memory for recognizing an event is disclosed. The system comprises a first transmitter and a second transmitter in a venue, at least one first receiver and at least one second receiver in the venue, and an event recognition engine. The first transmitter is configured for: for each of at least one known event happening in the venue in a respective training time period, transmitting a respective training wireless signal through a wireless multipath channel impacted by the known event in the venue in the training time period associated with the known event. Each of the at least one first receiver is configured for: for each of the at least one known event happening in the venue, receiving asynchronously the respective training wireless signal through the wireless multipath channel, obtaining, asynchronously based on the respective training wireless signal, at least one time series of training channel information (training CI time series) of the wireless multipath channel between the first receiver and the first transmitter in the training time period associated with the known event, and pre-processing the at least one training CI time series. The second transmitter is configured for: for a current event happening in the venue in a current time period, transmitting a current wireless signal through the wireless multipath channel impacted by the current event in the venue in the current time period associated with the current event. Each of the at least one second receiver is configured for: for the current event happening in the venue in the current time period, receiving asynchronously the current wireless signal through the wireless multipath channel, obtaining, asynchronously based on the current wireless signal, at least one time series of current channel information (current CI time series) of the wireless multipath channel between the second receiver and the second transmitter in the current time period associated with the current event, and pre-processing the at least one current CI time series. The event recognition engine is configured for: training at least one classifier for the at least one known event based on the at least one training CI time series; and applying the at least one classifier to: classify at least one of: the at least one current CI time series, a portion of a particular current CI time series, and a combination of the portion of the particular current CI time series and a portion of an additional CI time series, and associate the current event with at least one of: a known event, an unknown event and another event. A training CI time series associated with a first receiver and a current CI time series associated with a second receiver have at least one of: different starting times, different time durations, different stopping times, different counts of items in their respective time series, different sampling frequencies, different sampling periods between two consecutive items in their respective time series, and channel information (CI) with different features.

In yet another embodiment, an event recognition engine of a wireless monitoring system is disclosed. The system comprises a first transmitter and a second transmitter in a venue, at least one first receiver and at least one second receiver in the venue, and the event recognition engine. The event recognition engine comprises: a processor, a memory communicatively coupled with the processor, and a set of instructions stored in the memory. The set of instructions, when executed, causes the processor to perform: for each of at least one known event happening in a venue, obtaining, from each of at least one first receiver in the venue, at least one time series of training channel information (training CI time series) of a wireless multipath channel, wherein the first receiver extracts the training CI time series from a respective training wireless signal received from a first transmitter in the venue through the wireless multipath channel between the first receiver and the first transmitter in a training time period associated with the known event, training at least one classifier for the at least one known event based on the at least one training CI time series, for a current event happening in the venue in a current time period, obtaining, from each of at least one second receiver in the venue, at least one time series of current channel information (current CI time series) of the wireless multipath channel impacted by the current event, wherein the second receiver extracts the current CI time series from a current wireless signal received from a second transmitter in the venue through the wireless multipath channel between the second receiver and the second transmitter in the current time period associated with the current event, and applying the at least one classifier to: classify at least one of: the at least one current CI time series, a portion of a particular current CI time series, and a combination of the portion of the particular current CI time series and a portion of an additional CI time series, and associate the current event with at least one of: a known event, an unknown event and another event. A training CI time series associated with a first receiver and a current CI time series associated with a second receiver have at least one of: different starting times, different time durations, different stopping times, different counts of items in their respective time series, different sampling frequencies, different sampling periods between two consecutive items in their respective time series, and channel information (CI) with different features.

In still another embodiment, a receiver of a wireless monitoring system is disclosed. The receiver comprises: a wireless circuitry, a processor communicatively coupled with the wireless circuitry, a memory communicatively coupled with the processor, and a set of instructions stored in the memory. The wireless circuitry is configured to: for each of at least one known event happening in a venue, receive a respective training wireless signal through a wireless multipath channel, wherein the respective training wireless signal is transmitted by a first transmitter through the wireless multipath channel between the receiver and the first transmitter in a training time period associated with the known event, and for a current event happening in the venue in a current time period, receive a current wireless signal through the wireless multipath channel impacted by the current event, wherein the current wireless signal is transmitted by a second transmitter through the wireless multipath channel between the receiver and the second transmitter in the current time period associated with the current event. The set of instructions, when executed, causes the processor to: for each of the at least one known event happening in the venue, obtain, asynchronously based on the respective training wireless signal, at least one time series of training channel information (training CI time series) of the wireless multipath channel, and for the current event happening in the venue in the current time period, obtain, asynchronously based on the current wireless signal, at least one time series of current channel information (current CI time series) of the wireless multipath channel. The at least one training CI time series is used by an event recognition engine of the wireless monitoring system to train at least one classifier for the at least one known event. The at least one classifier is applied to: classify at least one of: the at least one current CI time series, a portion of a particular current CI time series, and a combination of the portion of the particular current CI time series and a portion of an additional CI time series, and associate the current event with at least one of: a known event, an unknown event and another event.

Other concepts are related to software for implementing the present teaching on recognizing security related events based on wireless channel information in a rich-scattering environment.

Additional novel features will be set forth in part in the description which follows, and in part will become apparent to those skilled in the art upon examination of the following and the accompanying drawings or may be learned by production or operation of the examples. The novel features of the present teachings may be realized and attained by practice or use of various aspects of the methodologies, instrumentalities and combinations set forth in the detailed examples discussed below.

BRIEF DESCRIPTION OF DRAWINGS

The methods, systems, and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings.

DETAILED DESCRIPTION

Figure 1:
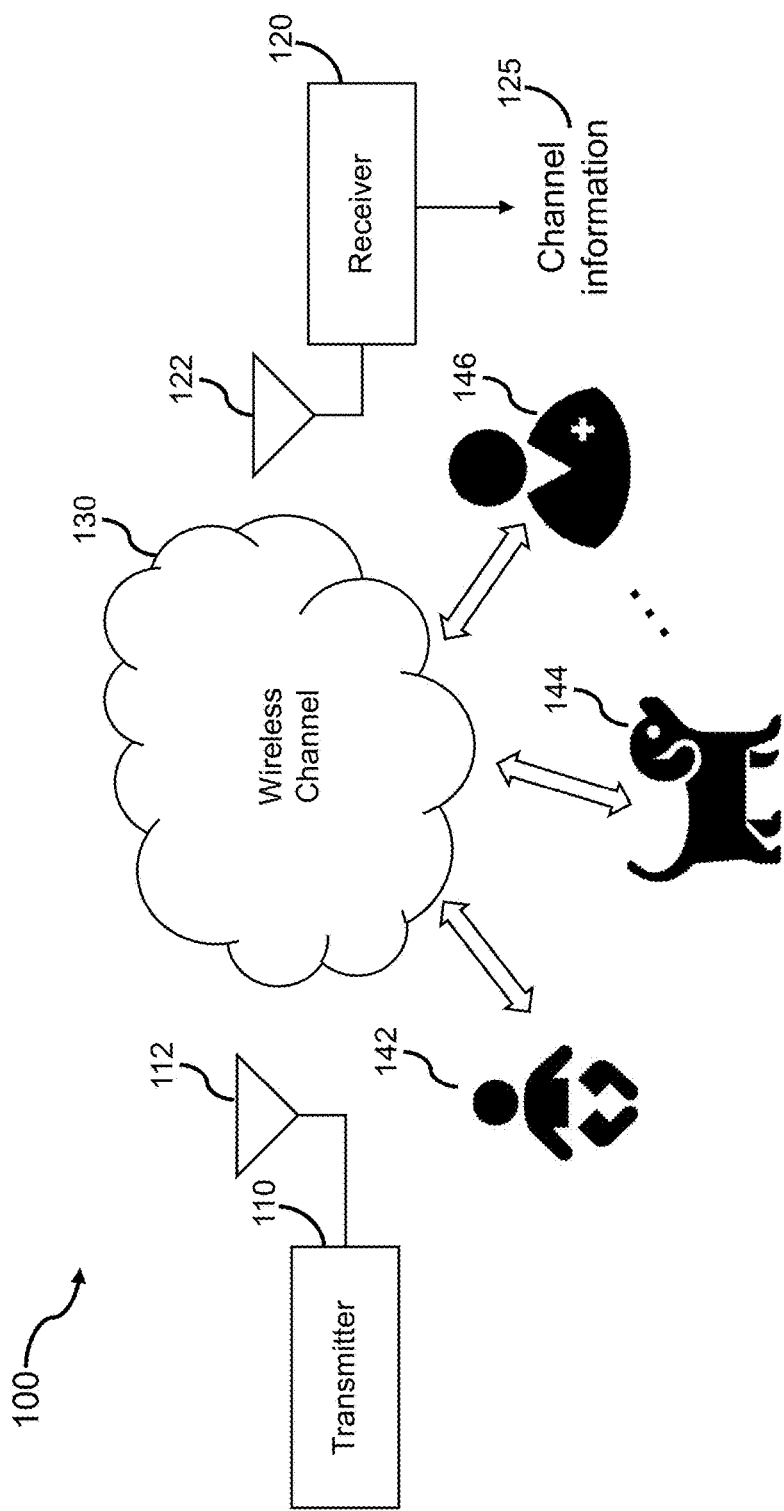
FIG. 1 illustrates an exemplary network environment for event detection and monitoring in a venue, according to one embodiment of the present teaching.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The present teaching discloses systems, apparatus, and methods for recognizing events (e.g. events related to object motion and/or security) in a venue based on a time series of channel information (CI) of a wireless multipath channel that is impacted by the object motion. According to various embodiments, the disclosed system can be integrated into a security system to monitor opening of front door (e.g. by intruders or by dementia patients), opening of window, etc. The disclosed system can be trained to know "when the door is opened", "when the door is closed", etc.

In one embodiment, the system uses discrete training to recognize: "door fully open", "door fully close", and "door half open". In another embodiment, the system is trained for continuous monitoring, and may use dynamic time warping (DTW) to monitor the door movement continuously so that every position of the door (e.g. x % open with x being between 0 and 100) can be detected and recognized.

In one embodiment, the disclosed system has hardware components (e.g. wireless transmitter/receiver with antenna, analog circuitry, power supply, processor, memory, etc.) and corresponding software components. According to various embodiments of the present teaching, the disclosed system includes a Bot (referred to as a Type 1 device) and an Origin (referred to as a Type 2 device) for transient motion detection and monitoring. Each device comprises a transceiver, a processor and a memory.

The disclosed system is easy and simple to install with a low hardware cost. In one embodiment, the disclosed system only needs two wireless devices (a Type 1 device and a Type 2 device) to cover a 1500-sqft house. The wireless devices are plug-and-play, and can be plugged into wall power sockets in opposite corner of the house. The disclosed system can be improved over time with machine learning, and can be upgraded via remote software upgrade. The system can do software diagnosis, which makes its maintenance and repair an easy job.

The disclosed system includes features that are significantly more than an abstract idea. A security system with low cost and high accuracy has been desired for a long time. The disclosed system solves the long-time problem using physical WiFi chips as sensors to monitor the environment with WiFi signals and the associated multipath patterns. The disclosed system has hardware components (e.g. Type 1 device, Type 2 device each with processor, memory, wireless transceivers, cloud server, etc.). The WiFi signals are electromagnetic (EM) waves in the air which are measurable and with deterministic structure and frequency characteristics. The system has matching software components (e.g. embedded software in Type 1 device, in Type 2 device, in servers, etc.). The software can interface with low-level WiFi chips and firmware to extract CSI. Experimental results show that the disclosed system can recognize security related events and motions with very high accuracy.

The disclosed system can be applied in many cases. In one example, the Type 1 device (transmitter) may be a small WiFi-enabled device resting on the table. It may also be a WiFi-enabled television (TV), set-top box (STB), a smart speaker (e.g. Amazon echo), a smart refrigerator, a smart microwave oven, a mesh network router, a mesh network satellite, a smart phone, a computer, a tablet, a smart plug, etc. In one example, the Type 2 (receiver) may be a WiFi-enabled device resting on the table. It may also be a WiFi-enabled television (TV), set-top box (STB), a smart speaker (e.g. Amazon echo), a smart refrigerator, a smart microwave oven, a mesh network router, a mesh network satellite, a smart phone, a computer, a tablet, a smart plug, etc. The Type 1 device and Type 2 devices may be in a home security system for an owner of a house to detect any intrusion and any unexpected activity in and around the house. The Type 1 device and Type 2 devices may be placed in bedrooms, bathrooms, baby-rooms, restrooms to monitor unexpected intrusion or suspicious activities. The Type 1 device and Type 2 devices may be deployed in an area to detect sudden or unexpected motions indicating any intruder or accident.

Hardware modules may be constructed to contain the Type 1 transceiver and/or the Type 2 transceiver. The hardware modules may be sold to/used by variable brands to design, build and sell final commercial products. Products using the disclosed system and/or method may be home/office security products, motion monitoring products, WiFi products, mesh products, TV, STB, entertainment system, HiFi, speaker, home appliance, lamps, stoves, oven, microwave oven, table, chair, bed, shelves, tools, utensils, torches, vacuum cleaner, smoke detector, sofa, piano, fan, door, window, door/window handle, locks, smoke detectors, car accessories, computing devices, office devices, air conditioner, heater, pipes, connectors, surveillance camera, access point, computing devices, mobile devices, LTE devices, 3G/4G/5G/6G devices, gaming devices, eyeglasses, glass panels, VR goggles, necklace, watch, waist band, belt, wallet, pen, hat, wearables, implantable device, tags, parking tickets, smart phones, etc.

In addition, sleep monitoring acts as a critical and challenging task that attracts increasing demands and interests. The present teaching discloses the model, design, and implementation of SMARS (Sleep Monitoring via Ambient Radio Signals), which is the first practical Sleep Monitoring system that exploits Ambient Radio Signals to recognize sleep stages and assess sleep quality. This will enable a future smart home that monitors daily sleep in a ubiquitous, non-invasive and contactless manner, without instrumenting the subject's body or the bed. Different from previous RF-based approaches, the present teaching devises a statistical model that accounts for all reflecting and scattering multipaths, allowing highly accurate and instantaneous breathing estimation with ever best performance achieved on commodity devices. On this basis, SMARS then recognizes different sleep stages, including wake, REM, and NREM, which is previously only possible with dedicated hardware. A real-time system is implemented on commercial WiFi chipsets and deployed in 6 homes with 6 participants, resulting in 32 nights of data in total. The results demonstrate that SMARS yields a median error of 0.47 bpm and a 95% error of only 2.92 bpm for breathing estimation, and detects breathing robustly even when a person is 10 m away from the link, or behind a wall. SMARS achieves sleep staging accuracy of 85%, outperforming advanced solutions using contact sensor or radar. Furthermore, SMARS is evaluated upon a recently released dataset that measures 20 patients' overnight sleep, which confirms the performance. By achieving promising results with merely a single commodity RF link, SMARS will set the stage for a practical in-home sleep monitoring solution.

Sleep plays a vital role in an individual's health and well-being, both mentally and physically. It is well recognized that sleep quantity and quality is fundamentally related to health risks like cardiovascular decease, stroke, kidney failure, diabetes, and adverse mental conditions, etc. Unfortunately, in modern society, a number of people suffer from sleep disorders. As recently reported, 10% of the population suffers from chronic insomnia (which is even higher among elders), and ⅓ of Americans do not get sufficient sleep. Monitoring sleep emerges as an essential demand to help, manage, diagnose, and treat the growing group of sleep disorders as well as to keep regular tabs on personal health.

Sleep monitoring, however, is a challenging task that has drawn tremendous efforts for decades. Generally, it measures sleep time, recognizes different sleep stages, e.g., wake, REM (Rapid Eye Movement) and NREM (Non-REM), and accordingly assesses an individual's sleep quality. Various solutions have been proposed. The medical gold standard relies on Polysomnography (PSG), which monitors various physiological parameters such as brain activities, respirations, and body movements by a number of wired sensors attached to the patient. Albeit accurate and comprehensive, PSG is usually expensive and cumbersome with the invasive sensors that may cause sleep difficulties, limiting itself to clinical usage for confirmed patients. Other approaches including photoplethysmography (PPG) and actigraphy (ACT) require users to wear dedicated sensors during sleep. Ballistocardiogram (BCG) needs to instrument the mattress with an array of EMFi sensors to measure ballistic force. Despite of the costs, these approaches provide suitable solutions for those who need special cares but are less-than-ideal for the public. Recent efforts in mobile computing envision in-home sleep monitoring using smartphones and wearables. These methods, however, only provide coarse-grained, less accurate measurements and fail to monitor vital signs like respiratory rate. In addition, mobiles and wearables are undesirable for especially elders and those with dementia.

Different from prevailing solutions, the disclosed solution looks forward to a future smart home that monitors daily sleep in a ubiquitous, non-invasive, contactless, and accurate manner, without instrumenting the body or the bed. One can observe an opportunity towards such a system by two perspectives: 1) Clinical study has shown that physiological activity varies among different sleep stages. For example, breathing rate becomes irregular and fast since brain oxygen consumption increases during REM sleep, and is more stable and slower during NREM sleep, rendering the feasibility of sleep staging based on breathing monitoring. 2) Recent advances in wireless technology have demonstrated non-contact sensing of body motions in the environments. Chest and abdomen motions caused by breathing can alter radio signal propagations and thus modulate the received signals, from which it is then possible to decipher breathing. One can explore a synergy between the two perspectives, resulting in a system to leverage ambient radio signals (e.g., WiFi) to capture a person's breathing and motion during sleep and further monitor the sleep behaviors.

While early works have investigated the feasibility of RF-based breathing estimation and sleep monitoring, they either rely on specialized hardware like FMCW radar, or only work in controlled environments. Solutions based on dedicated radios are usually expensive and not ubiquitously applicable. Others using commodity devices typically require the user to lay still on a bed with radios exceedingly close to his/her chest and fail in presence of extraneous motions or in Non-Line-Of-Sight (NLOS) scenarios. In addition, none of them can identify different sleep stages due to their limited accuracy in breathing estimation. Such limitations prevent them from application for practical in-home sleep monitoring.

The present teaching disclose the model, design, and implementation of SMARS, the first practical Sleep Monitoring system that exploits commodity Ambient Radio Signals to recognize sleep stages and assess the otherwise elusive sleep quality. SMARS works in a non-obtrusive way without any body contact. All that a user needs to do is to set up one single link between two commodity radios by, e.g., simply placing a receiver if a wireless router is already installed inside the home. SMARS advances the literature by a novel statistical model that allows highly accurate and instantaneous breathing estimation. On this basis, SMARS is able to distinguish different sleep stages, which is previously only obtainable by expensive dedicated hardware. Specifically, SMARS excels in three unique aspects to deliver practical sleep monitoring. First, one can devise a statistical model on motion in Channel State Information (CSI) that leverages all reflection and scattering multipaths indoors. Existing works usually assume a geometrical model with a few multipaths and one major path reflected off the human body (e.g., using a 2-ray model developed for outdoor space). Under real-world indoor environments, however, there could be as many as hundreds of multipaths, and signals not only reflect but also scatter off a person's body and other objects in the space. As a consequence, previous approaches fail in NLOS environments and for minute motions due to the lack of a dominant reflection path. In contrast, the disclosed model investigates the statistical characteristics of motion in CSI without making such unrealistic assumptions, underlying robust detection of arbitrary motions including breathing.

Second, SMARS achieves accurate respiratory rate estimation instantaneously and robustly. Most of previous breathing estimation schemes assume constant breathing rate during a relatively large time window to gain sufficient frequency resolution, losing fine-grained breathing variations during sleep. In addition, minute breathing motions can be easily buried in CSI measurement noises, rendering existing philosophies effective only in extraordinary close proximity (typically within 2-3 m) without any extraneous motions. To improve time resolution, SMARS exploits the time-domain Auto-Correlation Function (ACF) to estimate breathing rate, which can report real-time breathing rates as frequent as every one second and make it possible to capture instantaneous breathing rate changes. By using ACF, SMARS also circumvents the use of noisy phase and the usually handcrafted CSI denoising procedure. More importantly, by eliminating the frequency offsets and thus synchronizing breathing signal over different subcarriers, ACF allows us to perform Maximal Ratio Combining (MRC) to combine multiple subcarriers to combat measurement noises and maximize breathing signals in an optimal way. By doing so, one can push the limit of the breathing signal to noise ratio (SNR) and thus significantly increase the sensing sensitivity for larger coverage as well as weaker breathing. Specifically, SMARS can reliably detect breathing when a person is 10 m away from the link, or behind a wall, which is even better than specialized low-power radars.

Finally, based on the extracted breathing rates and motion statistics during sleep, one can recognize different sleep stages (including wake, REM and NREM) and comprehensively assess the overall sleep quantity and quality. Based on in-depth understanding of the relationship between breathing rates and sleep stages, one can extract distinctive breathing features for classification for sleep staging. None of existing works using off-the-shelf devices can achieve the same goal of staging sleep.

A real-time system has been implemented on different commercial WiFi chipsets and its performance is evaluated through extensive experiments. The evaluation includes two parts: 1) One can deploy SMARS in 6 homes with 6 healthy subjects and collect 32 nights of data, 5 out of which have PSG data recorded by commercial devices. The results show that SMARS achieves great performance, with a median breathing estimation error of 0.47 breath per minute (bpm) and a 95% tile error of 2.92 bmp. Regarding sleep staging, SMARS produces a remarkable accuracy of 85.2%, while commercial solutions, e.g., EMFIT based on contact sensors and ResMed using radar, have accuracies of only 69.8% and 83.7% respectively. 2) One can further validate SMARS on a recently released dataset on RF-based respiration monitoring. The dataset collected 20 patients' overnight sleep for comparative evaluation of four state-of-the-art breathing monitoring systems, using clinically labeled PSG data as ground truths. All the four systems (based on ZigBee, Sub-RSS radio, UWB radar, and WiFi CSI, respectively) produce significant median errors of about 2-3 bpm and 95% tile errors of around or above 10 bpm. As comparison, SMARS achieves significant improvements by decreasing the median error to 0.66 bpm and the 95% tile error to 3.79 bpm. By achieving promising performance, SMARS can deliver clinically meaningful sleep monitoring for daily and regular use in practice and takes an important step towards a future smart home that monitors personal health everyday life.

In a nutshell, the core contribution here is SMARS, the first system that enables a smart home to stage an inhabitant's sleep using commodity off-the-shelf WiFi devices, by achieving highly accurate and instantaneous breathing estimation in the wild. SMARS also contributes the first statistical model for understanding and capturing motions in CSI, which will renovate various applications in wireless sensing.

In one embodiment, the present teaching discloses a method, an apparatus, a device, a system, and/or software (method/apparatus/device/system/software) of a wireless monitoring system. A time series of channel information (CI) of a wireless multipath channel may be obtained using a processor, a memory communicatively coupled with the processor and a set of instructions stored in the memory. The time series of CI may be extracted from a wireless signal transmitted between a Type 1 heterogeneous wireless device and a Type 2 heterogeneous wireless device in a venue through the wireless multipath channel. The wireless multipath channel may be impacted by a motion of an object in the venue. A characteristics and/or a spatial-temporal information of the object and/or of the motion of an object may be monitored based on the time series of CI. A task may be performed based on the characteristics and/or the spatial-temporal information. A presentation associated with the task may be generated in a user-interface (UI) on a device of a user. The time series of CI may be preprocessed.

The Type 1 device may comprise at least one heterogeneous wireless transmitter. The Type 2 device may comprise at least one heterogeneous wireless receiver. The Type 1 device and the Type 2 device may be the same device. Any device may have a processor, a memory communicatively coupled with the processor, and a set of instructions stored in the memory to be executed by the processor.

There may be multiple Type 1 heterogeneous wireless devices interacting with the same Type 2 heterogeneous wireless device, and/or there may be multiple Type 2 heterogeneous wireless devices interacting with the same Type 1 heterogeneous wireless device. The multiple Type 1 devices/Type 2 devices may be synchronized and/or asynchronous, with same/different window width/size and/or time shift. The multiple Type 1 devices/Type 2 devices may operate independently and/or collaboratively. The multiple Type 1 devices/Type 2 devices may be communicatively coupled to same or different servers (e.g. cloud server, edge server, local server). Operation of one device may be based on operation, state, internal state, storage, processor, memory output, physical location, computing resources, network of another device. Difference devices may communicate directly, and/or via another device/server/cloud server. The devices may be associated with one or more users, with associated settings. The settings may be chosen once, pre-programmed, and/or changed over time.

In the case of multiple Type 1 devices interacting with multiple Type 2 devices, any processing (e.g. time domain processing and/or frequency domain processing) may be different for different devices. The processing may be based on locations, orientation, direction, roles, user-related characteristics, settings, configurations, available resources, available bandwidth, network connection, hardware, software, processor, co-processor, memory, battery life, available power, antennas, antenna types, directional/unidirectional characteristics of the antenna, power setting, and/or other parameters/characteristics of the devices.

The wireless receiver (e.g. Type 2 device) may receive the wireless signal and/or another wireless signal from the wireless transmitter (e.g. Type 1 device). The wireless receiver may receive another wireless signal from another wireless transmitter (e.g. a second Type 1 device). The wireless transmitter may transmit the wireless signal and/or another wireless signal to another wireless receiver (e.g. a second Type 2 device). The wireless transmitter, the wireless receiver, the another wireless receiver and/or the another wireless transmitter may be moving with the object and/or another object. The another object may be tracked.

The Type 1 device may be capable of wirelessly coupling with at least two Type 2 devices. The Type 2 device may be capable of wirelessly coupling with at least two Type 1 devices. The Type 1 device may be caused to switch/establish wireless coupling from the Type 2 device to a second Type 2 heterogeneous wireless device at another location in the venue. Similarly, the Type 2 device may be caused to switch/establish wireless coupling from the Type 1 device to a second Type 1 heterogeneous wireless device at yet another location in the venue. The switching may be controlled by a server, the processor, the Type 1 device, the Type 2 device, and/or another device. The radio used before switching may be different from the radio used after the switching. A second wireless signal may be caused to be transmitted between the Type 1 device and the second Type 2 device (or between the Type 2 device and the second Type 1 device) through the wireless multipath channel. A second time series of CI of the wireless multipath channel extracted from the second wireless signal may be obtained. The second wireless signal may be the first wireless signal. The characteristics, the spatial-temporal information and/or another quantity of the motion of the object may be monitored based on the second time series of CI. The Type 1 device and the Type 2 device may be the same device.

The wireless signal and/or the another wireless signal may have data embedded. The wireless receiver, the wireless transmitter, the another wireless receiver and/or the another wireless transmitter may be associated with at least one processor, memory communicatively coupled with respective processor, and/or respective set of instructions stored in the memory which when executed cause the processor to perform any and/or all steps needed to determine the spatial-temporal information, the initial spatial-temporal information, the initial time, the direction, the instantaneous location, the instantaneous angle, and/or the speed, of the object.

The processor, the memory and/or the set of instructions may be associated with the Type 1 heterogeneous wireless transceiver, one of the at least one Type 2 heterogeneous wireless transceiver, the object, a device associated with the object, another device associated with the venue, a cloud server, and/or another server.

The Type 1 device may transmit the wireless signal (e.g. a series of probe signals) in a broadcasting manner to at least one Type 2 device(s) through the wireless multipath channel in the venue. The wireless signal is transmitted without the Type 1 device establishing wireless connection with any of the at least one Type 2 device receiver(s).

The Type 1 device may transmit to a particular destination media access control (MAC) address common for more than one Type 2 devices. Each of the more than one Type 2 devices may adjust their MAC address to the particular MAC address.

The particular destination MAC address (common destination MAC address) may be associated with the venue. The association may be recorded in an association table of an Association Server. The venue may be identified by the Type 1 device, a Type 2 device and/or another device based on the particular destination MAC address, the series of probe signals, and/or the at least one time series of CI extracted from the probe signals.

For example, a Type 2 device may be moved to a new location in the venue (e.g. from another venue). And the Type 1 device may be newly set up in the venue such that the Type 1 device and the Type 2 device are not aware of the existence of each other, and they may not establish wireless connection at all. During set up, the Type 1 device may be instructed/guided/caused/controlled to send the series of probe signals to the particular destination MAC address (e.g. using a dummy receiver, using a hardware pin setting/connection, using a stored setting, using a local setting, using a remote setting, using a downloaded setting, or using a server). Upon power up, the Type 2 device may scan for probe signals according to a table of destination MAC addresses that may be used at different locations (e.g. different MAC address for different venue such as house, office, enclosure, floor, multi-storey building, store, airport, mall, stadium, hall, station, subway, lot, area, zone, region, district, city, country, continent). When the Type 2 device detects the probe signals sent to the particular destination MAC address, the Type 2 device can use the table to identify the venue based on the particular destination MAC address.

A location of a Type 2 device in the venue may be computed based on the particular destination MAC address, the series of probe signals, and/or the at least one time series of CI obtained by the Type 2 device from the probe signals. The computing may be performed by the Type 2 device.

The particular destination MAC address may be changed over time. It may be changed according to a time table, a rule, a policy, a mode, a condition, a situation and/or a change. The particular destination MAC address may be selected based on availability of the MAC address, a pre-selected list, collision pattern, traffic pattern, data traffic between the Type 1 device and another device, effective bandwidth, random selection, and/or a MAC address switching plan. The particular destination MAC address may be the MAC address of a second wireless device (e.g. a dummy receiver, or a receiver that serves as a dummy receiver).

The Type 1 device may transmit the probe signals in a channel selected from a set of channels. At least one CI of the selected channel may be obtained by a respective Type 2 device from the probe signal transmitted in the selected channel.

The selected channel may be changed over time. The change may be according to a time table, a rule, a policy, a mode, a condition, a situation, and/or a change. The selected channel may be selected based on availability of channels, a pre-selected list, co-channel interference, inter-channel interference, channel traffic patterns, data traffic between the Type 1 device and another device, effective bandwidth associated with channels, a security criterion, random selection, a channel switching plan, a criterion, and/or a consideration.

The particular destination MAC address and/or an information of the selected channel may be communicated between the Type 1 device and a server through a network. The particular destination MAC address and/or the information of the selected channel may also be communicated between a Type 2 device and a server through another network. The Type 2 device may communicate the particular destination MAC address and/or the information of the selected channel to another Type 2 device (e.g. via a mesh network, via Bluetooth, via WiFi, etc). The particular destination MAC address and/or the information of the selected channel may be chosen by a server. The particular destination MAC address and/or the information of the selected channel may be signaled in an announcement channel by the Type 1 device and/or a server. Before the particular destination MAC address and/or the information of the selected channel is being communicated, it may be pre-processed.

Wireless connection between the Type 1 device and another wireless device may be established. The Type 1 device may send a first wireless signal (e.g. a sounding frame, a probe signal, a request-to-send RTS) to the another wireless device. The another wireless device may reply by sending a second wireless signal (e.g. a command, or a clear-to-send CTS) to the Type 1 device, triggering the Type 1 device to transmit the wireless signal (e.g. series of probe signals) in the broadcasting manner to the at least one Type 2 device without establishing wireless connection with any of the at least one Type 2 device. The second wireless signal may be a response or an acknowledge (e.g. ACK) to the first wireless signal. The second wireless signal may contain a data with information of at least one of: the venue, and the Type 1 device. The first wireless signal may also be in response to the second wireless signal.

The another wireless device may be a dummy wireless device with a purpose (e.g. a primary purpose, a secondary purpose) to establish the wireless connection with the Type 1 device, to receive the first wireless signal, and/or to send the second wireless signal. The another wireless device may be physically attached to the Type 1 device.

In another example, the another wireless device may send a third wireless signal to the Type 1 device triggering the Type 1 device to transmit the wireless signal (e.g. series of probe signals) in the broadcasting manner to the at least one Type 2 device without establishing wireless connection with any of the at least one Type 2 device. The Type 1 device may reply to the third wireless signal by transmitting a fourth wireless signal to the another wireless device.

The another wireless device may not communicate further with the Type 1 device after establishing the connection with the Type 1 device. The another wireless device may suspend communication with the Type 1 device after establishing the connection. The communication may be resumed in the future. The another wireless device may enter an inactive mode, a hibernation mode, a sleep mode, a stand-by mode, a low-power mode, an OFF mode and/or a power-down mode, after establishing the wireless connection with the Type 1 device.

The another wireless device may have the particular destination MAC address. It may use the wireless connection to trigger the Type 1 device to send the at least one series of probe signals in a broadcasting manner to the particular destination MAC address. Each of the at least one Type 2 device may set its MAC address to the particular destination MAC address so as to receive the at least one series of probe signals from the Type 1 device. A new Type 2 device in the venue may obtain the particular destination MAC address from a designated source (e.g. a cloud server, an edge server, a remote server, a local server, a web server, an internet server, a webpage, a database) and set its MAC address to the particular destination MAC address so as to receive the at least one series of probe signals from the Type 1 device Both the Type 1 device and the another wireless device may be controlled and/or coordinated by at least one of: a first processor associated with the Type 1 device, a second processor associated with the another wireless device, a third processor associated with the designated source and/or a fourth processor associated with another device. The first processor and the second processor may coordinate with each other.

A first series of probe signals may be transmitted by a first antenna of the Type 1 device to at least one first Type 2 device through a first wireless multipath channel in a first venue. A second series of probe signals may be transmitted by a second antenna of the Type 1 device to at least one second Type 2 device through a second wireless multipath channel in a second venue. The first series and the second series may/may not be different. The at least one first Type 2 device may/may not be different from the at least one second Type 2 device. The first series and/or the second series of probe signals may be transmitted in a broadcasting manner. The first antenna may/may not be different from the second antenna.

The Type 1 device may send the two separate series of probe signals to two separate groups of Type 2 devices located in two venues. The first set of Type 2 devices (the at least one first Type 2 device) may receive the first time series of probe signals through a first wireless multipath channel of the first venue. The second set of Type 2 devices (the at least one second Type 2 device) may receive the second time series of probe signals through a second wireless multipath channel in the second venue. If in broadcasting mode, Type 1 device may not establish wireless connection with any of the at least one first and second Type 2 devices.

The two venues may have different sizes, shape, multipath characteristics. The first venue and the second venue may overlap partially. The immediate area around the first antenna and second antenna may be part of the overlapped area. The first venue may be a subset of the second venue, or vice versa. The first wireless multipath channel and the second wireless multipath channel may be different. For example, the first one may be WiFi while the second may be LTE. Or, both may be WiFi, but the first one may be 2.4 GHz WiFi and the second may be 5 GHz WiFi. Or, both may be 2.4 GHz WiFi, but may have different channel numbers, with different SSID names, and WiFi settings (e.g. encryption—the first may use PKA and the second may use PKA2).

Each first Type 2 device may obtain at least one first time series of CI from the first series of probe signals, the CI being of the first wireless multipath channel between the first Type 2 device and the Type 1 device. Each second Type 2 device may obtain at least one second time series of CI from the second series of probe signals, the CI being of the second wireless multipath channel between the second Type 2 device and the Type 1 device.

The first antenna may/may not be the second antenna. The at least one first Type 2 device may/may not be the same as the at least one second Type 2 device. A particular first Type 2 device may be the same as a particular second Type 2 device. The first and second series of probe signals may/may not be synchronous. The transmission of the first series of probe signals may not be synchronous to the transmission of the second series of probe signals. A probe signal may be transmitted with data. A probe signal may be replaced by a data signal.

The first series of probe signals may be transmitted at a first pseudo-regular interval (e.g. at a rate of 30 Hz). The second series of probe signals may be transmitted at a second pseudo-regular interval (e.g. at a rate of 300 Hz). The first pseudo-regular interval may/may not be different from the second pseudo-regular interval. The first and/or second pseudo-regular interval may be changed over time. The change may be according to at least one of: a time table, a rule, a policy, a mode, a condition, a situation, and/or a change. Any pseudo-regular interval may be changed over time.

The first series of probe signals may be transmitted to a first destination MAC address. The second series of probe signals may be transmitted to a second destination MAC address. The two destination MAC addresses may/may not be different. Any of the two destination MAC addresses may be changed over time. The change may be according to at least one of: a time table, a rule, a policy, a mode, a condition, a situation, and/or a change.

The first series of probe signals may be transmitted in a first channel. The second series of probe signals may be transmitted in a second channel. The first channel and the second channel may/may not be different. The first channel and/or the second channel may be changed over time. The change may be according to at least one of: a time table, a rule, a policy, a mode, a condition, a situation, and/or a change.

A first wireless connection may be established between the Type 1 device and another wireless device. The Type 1 device may establish the first wireless connection with the another wireless device. The Type 1 device may send a first wireless signal to the another wireless device. The another wireless device may send a second wireless signal to the Type 1 device. One of the first wireless signal and the second wireless signal may be in response to the other. The second wireless signal to the Type 1 device may trigger the Type 1 device to transmit the first series of probe signals in the broadcasting manner. The second wireless signal may be an acknowledge to the first wireless signal.

A second wireless connection may be established between the Type 1 device and yet another wireless device. The Type 1 device may establish the second wireless connection with the yet another wireless device. The Type 1 device may send a third wireless signal to the yet another wireless device. The yet another wireless device may send a fourth wireless signal to the Type 1 device. One of the third wireless signal and the fourth wireless signal may be in response to the other. The fourth wireless signal to the Type 1 device may trigger the Type 1 device to transmit the second series of probe signals in the broadcasting manner. The fourth wireless signal may be an acknowledge to the third wireless signal. The third wireless signal may be similar to the first wireless signal. The fourth wireless signal may be similar to the second wireless signal. The yet another wireless device may be the another wireless device. The third wireless signal may be sent by the Type 1 device before the first wireless communication is fully established and/or completed.

The another wireless device and the yet another wireless device may be the same device, which may perform signal handshake (e.g. the handshake with the first wireless signal and second wireless signal, or the handshake with the third signal and the fourth signal) with all Type 1 devices sequentially to trigger them to transmit in the broadcasting manner. The signal handshake with the Type 1 devices may be performed in at least one of: a sequential manner, a parallel manner and a mixed manner (partially sequential, partially parallel).

The Type 1 device, the another wireless device and/or the yet another wireless device may be controlled and/or coordinated, physically attached, or may be of/in/of a common device. At least two of the Type 1 device, the another wireless device and/or the yet another wireless device may be controlled by/connected to a common data processor, or may be connected to a common bus interconnect/network/LAN/Bluetooth network/BLE network/wired network/wireless network/mesh network/mobile network/cloud, or may share a common memory, or may be associated with a common user/user profile/user account/identity (ID)/household/house/physical address/location/geographic coordinate/IP subnet/SSID/user device/home device/office device/manufacturing device.

The Type 1 device, the another wireless device and/or the yet another wireless device may each be associated a processor, a memory communicatively coupled with the processor, and a set of instruction stored in the memory to be executed by the processor. The Type 1 device, the another wireless device and/or the yet another wireless device may each comprise a processor, a memory communicatively coupled with the processor, and a set of instruction stored in the memory to be executed by the processor. When executed, the set of instructions may cause the device to perform an operation. Their processors may be coordinated.

At least one series of probe signals may be transmitted asynchronously and contemporaneously by each of more than one Type 1 heterogeneous wireless devices. Each respective series of probe signals is transmitted by an antenna of respective Type 1 heterogeneous wireless device in a broadcasting manner to a respective set of Type 2 devices through a wireless multipath channel, without the respective Type 1 device establishing wireless connection with any of the respective set of Type 2 receivers.

The transmitting may be using a respective processor, a respective memory and a respective set of instructions. Each of the more than one Type 1 heterogeneous wireless devices may have a heterogeneous integrated circuit (IC). Each of the respective set of Type 2 device may have a respective heterogeneous IC.

Each Type 1 device may be the signal source of a set of respective Type 2 devices (i.e. the Type 1 device sends a respective wireless signal (series of probe signals) to the set of respective Type 2 devices. Each respective Type 2 device chooses the Type 1 device from among all Type 1 devices as its signal source. Each Type 2 device may choose asynchronously (at different time). At least one time series of CI may be obtained by each respective Type 2 device from the respective series of probe signals from the Type 1 device, the CI being of the wireless multipath channel between the Type 2 device and the Type 1 device.

The respective Type 2 device chooses the Type 1 device from among all Type 1 devices as its signal source based on at least one of: identity (ID) of the Type 1 device and/or the respective Type 2 receiver, information of at least one of: a user, an account, access info, a parameter, a characteristics, and a signal strength associated with the Type 1 device and/or the respective Type 2 receiver, a task to be performed by the Type 1 device and/or the respective Type 2 receiver, whether the Type 1 device is the same as a past signal source, a history (of the past signal source, the Type 1 device, another Type 1 device, the respective Type 2 receiver, and another Type 2 receiver), and/or at least one threshold for switching signal source.

Initially, the Type 1 device may be the signal source of a set of initial respective Type 2 devices (i.e. the Type 1 device sends a respective wireless signal (series of probe signals) to the set of initial respective Type 2 devices) at an initial time. Each initial respective Type 2 device chooses the Type 1 device from among all Type 1 devices as its signal source.

The signal source (Type 1 device) of a particular Type 2 device may be changed when at least one of the following occurs: (1) a time interval between two adjacent probe signals (e.g. between the current probe signal and an immediate past probe signal, or between the next probe signal and the current probe signal) received from the current signal source of the particular Type 2 device exceeds a first threshold, (2) a signal strength associated with the current signal source of the Type 2 device is below a second threshold at the respective current time, (3) a processed signal strength associated with the current signal source of the Type 2 device is below a second threshold at the respective current time after the signal strength is processed with at least one of: a low pass filter, a band pass filter, a median filter, a moving average filter, a weighted averaging filter, a linear filter and a non-linear filter, and/or (4) the signal strength (or processed signal strength) associated with the current signal source of the Type 2 device is below a fourth threshold for a significant percentage of a recent time window (e.g. 70%, 80%, 90%, etc.). The percentage may exceed a fifth threshold. Any of first threshold, second threshold, third threshold, fourth threshold and fifth threshold may be time varying.

Condition (1) may occur when the Type 1 device and the Type 2 device become progressively far away from each other, such that some probe signal from the Type 1 device becomes too weak and is not received by the Type 2 device. Conditions (2)-(4) may occur when the two devices become far from each other such that the signal strength becomes very weak.

The signal source of the particular Type 2 device may not change if the other Type 1 devices have signal strength weaker than the current signal source (current selected Type 1 device). In another example, the signal source of the particular Type 2 device may also not change if the other Type 1 devices have signal strength weaker than a factor (e.g. 1.1, 1.2, or 1.5, etc.) of signal strength of the current signal source.

If the signal source is changed, the new signal source may take effect at a near future time (e.g. the respective next time). The new signal source may be the Type 1 device with strongest signal strength. The new signal source may also be the Type 1 device with strongest processed signal strength, wherein the signal strength of each Type 1 device may be processed with at least one of: a low pass filter, a band pass filter, a median filter, a moving average filter, a weighted averaging filter, a linear filter and a non-linear filter.

A list of available Type 1 devices may be initialized. The list may be updated by examining signal strength associated with the respective set of Type 1 devices. The list of available Type 1 devices may also be updated by examining processed signal strength associated with the respective set of Type 1 devices.

The respective chosen Type 1 device may/may not be different from the current signal source.

A Type 2 device may choose between the first series of probe signals and the second series of probe signals based on: respective pseudo-regular intervals, respective destination MAC addresses, respective channels, respective characteristics/properties/states, a respective task to be performed by the Type 2 device, signal strength of first series and second series, and/or another consideration.

The yet another wireless device and the another wireless device may be the same device. They may be in/on/of a common device. The Type 1 device may first establish the first wireless communication with the another wireless device, and then establish the second wireless communication with the yet another wireless device. The Type 1 device may start establishing the second wireless communication with the yet another wireless device before the first wireless communication is fully established. The Type 1 device may start establishing the second wireless communication with the yet another wireless device while the first wireless communication is being established.

The another wireless device may set its MAC address to a first destination MAC address and establish the first wireless connection with the Type 1 device using the first destination MAC address. The yet another wireless device may set its MAC address to a second destination MAC address and establish the second wireless connection with the Type 1 device using the second destination MAC address.

The transmitting may be using a processor, a memory and a set of instructions. Each of the Type 1 device and/or at least one Type 2 device may also have a heterogeneous IC. The heterogeneous IC may comprise the processor, memory and the set of instructions. The heterogeneous IC in different devices may be the same or different. Each Type 2 device may extract at least one time series of CI of the wireless multipath channel between the Type 1 device and the Type 2 device from the wireless signal. Each time series of CI is associated with an antenna of the Type 1 device and an antenna of the Type 2 device. The heterogeneous IC may generate the wireless signal, transmit or receive the wireless signal, extract the time series of CI from the wireless signal, and make the time series of CI available (e.g. to the processor/memory, other processors/memory).

Multiple Type 1 devices may transmit wireless signals asynchronously (e.g. to the same Type 2 device, to a number of Type 2 devices).

Multiple Type 2 devices may receive the wireless signal asynchronously. They may extract respective time series of CI from the wireless signal asynchronously, with respective heterogeneous starting time.

The wireless signal may be a series of probe signals. A probe signal may be transmitted with data. A probe signal may be replaced by a data signal.

The series of probe signals may be transmitted at a pseudo-regular interval (e.g. 100 probe signals per second). The pseudo-regular interval may be changed. The series of probe signals may be scheduled at a regular interval (e.g. 100 probe signals per second), but each probe signal may experience small time perturbation, perhaps due to timing requirement, timing control, network control, handshaking, message passing, collision avoidance, carrier sensing, congestion, availability of resources, and/or another consideration.

The series of probe signals may be transmitted at the pseudo-regular interval for a period of time. The pseudo-regular interval, the duration of the period of time and/or the starting time of the period of time, may be changed over time. For example, it may be 100 probe signals per second (probe/sec in short) for 2 hours and then changed to 1000 probe/sec for 30 minutes, and may change again.

The change may be according to a time table, a rule, a policy, a mode, a condition and/or a change (e.g. once every hour, or changed whenever a certain event occur). For example, the pseudo-regular interval may normally be 100 probe/sec, but will be changed to 1000 probe/sec in some demanding situations, and may be changed to 10 probe/sec in some low power and/or standby situation. The probe signals may be sent in burst also, e.g. at 100 probe/sec for 1 minute and no signal for some time before and after the burst. Or, the probe signal may be sent at 100 probe/sec and then momentarily at a burst rate of 1000 probe/sec for 1 minute and then back to 100 probe/sec. In another example, the probe signal may be sent at 1 probe/sec in a low power mode, at 10 probe/sec in a standby mode, at 100 probe/sec in a normal mode, and at 1000 probe/sec in an armed mode, etc.

The change based on at least one task performed by Type 1 device or Type 2 device. For example, the task of one receiver may need 10 probe/sec while the task of another receiver may need 1000 probe/sec. The pseudo-regular interval may be increased to 1000 probe/sec to satisfy the most demanding receiver. In one example, the receivers, the tasks associated with the receivers and/or the wireless multipath channel as experienced by the receivers may be divided into at least one class (e.g. a low priority class, a high priority class, an emergency class, a critical-task class, a regular class, a privileged class, a non-subscription class, a subscription class, a paying class, a non-paying class, etc.) and the pseudo-regular interval may be adjusted for the sake of some selected class (e.g. the high priority class). When the need of that selected class is less demanding, the pseudo-regular interval may be changed (increased or decreased). When a receiver has critically low power, the pseudo-regular interval may be reduced to reduce the power consumption of the receiver to respond to the probe signals.

In one example, the probe signals may be used to transfer power wirelessly to a receiver, and the pseudo-regular interval may be adjusted to control the amount of power being wirelessly transferred to the receiver.

The pseudo-regular interval may be changed by and/or based on a server, the Type 1 device and/or the Type 2 device. The server may be communicatively coupled with the Type 1 device and/or the Type 2 device. The change may be communicated between the server, the Type 1 device and/or the Type 2 device. For example, the server may monitor, track, forecast and/or anticipate the needs of the Type 2 device and/or the tasks performed by the receivers, and may decide to change the pseudo-regular interval accordingly. The server may send the change request to the Type 1 device (immediately or with some time delay) and the Type 1 device may then make the change. The server may keep track of a time table and may make scheduled changes to the pseudo-regular interval according to the time table. The server may detect an emergency situation of a receiver and change the pseudo-regular interval immediately. The server may detect a slowly happening condition (and/or an evolving condition) associated with a receiver and gradually adjust the pseudo-regular interval accordingly.

There may be more than one Type 1 devices. Each Type 1 device may transmit a respective wireless signal to more than one respective Type 2 devices through the wireless multipath channel in the venue. A CI time series may be obtained, each CI time series associated with a Type 1 device and a Type 2 device.

The characteristics and/or the spatial-temporal information of the motion of the object may be monitored individually based on a CI time series associated with a particular Type 1 device and a particular Type 2 device.

The characteristics and/or the spatial-temporal information of the motion of the object may be monitored jointly based on any CI time series associated with the particular Type 1 device and any Type 2 device.

The characteristics and/or the spatial-temporal information of the motion of the object may also be monitored jointly based on any CI time series associated with the particular Type 2 device and any Type 1 device.

The characteristics and/or the spatial-temporal information of the motion of the object may be monitored globally based on any CI time series associated with any Type 1 device and any Type 2 device.

Any joint monitoring (of the same motion or of the same object) may be associated with at least one of: a user, a user account, a profile, a household, a room, a location, and/or a user history, etc.

A first wireless multipath channel between a Type 1 device and a Type 2 device may be different from a second wireless multipath channel between another Type 1 device and another Type 2 device. The two wireless multipath channels may be associated with different frequency bands, different bandwidth, different carrier frequency, different modulation, different wireless standards, different coding, different encryption, different payload characteristics, different networks, different network parameters, etc.

The first wireless multipath channel and the second wireless multipath channel may be associated with different kinds of wireless system (e.g. two of the following: WiFi, LTE, LTE-A, 2.5G, 3G, 3.5G, 4G, beyond 4G, 5G, 6G, 7G, a 802.11 system, a 802.15 system, a 802.16 system, mesh network, Zigbee, WiMax, Bluetooth, BLE, RFID, UWB, microwave system, radar like system, etc.). For example, the first may be WiFi while the second may be LTE.

The first wireless multipath channel and the second wireless multipath channel may be associated with similar kinds of wireless system, but in different network. For example, the first wireless multipath channel may be associated with a WiFi network named "Pizza and Pizza" in the 2.4 GHz band with a bandwidth of 20 MHz while the second may be associated with a WiFi network called "StarBud hotspot" in the 5 GHz band with a bandwidth of 40 MHz.

The first wireless multipath channel may be associated with a particular wireless system (e.g. WiFi, or LTE, or 3G, or BLE, or mesh network, or adhoc network) while the second wireless multipath channel may be associated another wireless system of same kind as the first wireless multipath channel (e.g. both WiFi, or both LTE, or both 3G, etc.) with different network ID, SSID, characteristics, settings, and/or parameters. The first wireless multipath channel may also be a WiFi channel while the second wireless multipath channel may be another WiFi channel. For example, both first and second wireless multipath channels may be in the same WiFi network named "StarBud hotspot", using two different WiFi channels in "StarBud hotspot".

In one embodiment, a wireless monitoring system may comprise training at least one classifier of at least one known events in a venue based on training CI time series associated with the at least one events.

For each of the at least one known event happening in the venue in a respective training time period associated with the known event, a respective training wireless signal (e.g. a respective series of training probe signals) may be transmitted by an antenna of a first Type 1 heterogeneous wireless device using a processor, a memory and a set of instructions of the first Type 1 device to at least one first Type 2 heterogeneous wireless device through a wireless multipath channel in the venue in the respective training time period.

At least one respective time series of training CI (training CI time series) may be obtained asynchronously by each of the at least one first Type 2 device from the (respective) training wireless signal. The CI may be CI of the wireless multipath channel between the first Type 2 device and the first Type 1 device in the training time period associated with the known event. The at least one training CI time series may be preprocessed.

For a current event happening in the venue in a current time period, a current wireless signal (e.g. a series of current probe signals) may be transmitted by an antenna of a second Type 1 heterogeneous wireless device using a processor, a memory and a set of instructions of the second Type 1 device to at least one second Type 2 heterogeneous wireless device through the wireless multipath channel impacted by the current event in the venue in the current time period associated with the current event.

At least one time series of current CI (current CI time series) may be obtained asynchronously by each of the at least one second Type 2 device from the current wireless signal (e.g. the series of current probe signals). The CI may be CI of the wireless multipath channel between the second Type 2 device and the second Type 1 device in the current time period associated with the current event. The at least one current CI time series may be preprocessed.

The at least one classifier may be applied to classify at least one current CI time series obtained from the series of current probe signals by the at least one second Type 2 device, to classify at least one portion of a particular current CI time series, and/or to classify a combination of the at least one portion of the particular current CI time series and another portion of another CI time series. The at least one classifier may also be applied to associate the current event with a known event, an unknown event and/or another event.

Each wireless signal (e.g. each series of probe signals) may comprise at least two CI each with an associated time stamp. Each CI may be associated with a respective time stamp.

A current CI time series associated with a second Type 2 device and another current CI time series associated with another second Type 2 device may have different starting time, different time duration, different stopping time, different count of items in the time series, different sampling frequency, different sampling period between two consecutive items in the time series, and/or CI (CI) with different features.

The first Type 1 device and the second Type 1 device may be the same device. The first Type 1 device and the second Type 1 device may be at same location in the venue.

The at least one first Type 2 device and the at least one second Type 2 device may be the same. The at least one first Type 2 device may be a permutation of the at least one second Type 2 device. A particular first Type 2 device and a particular second Type 2 device may be the same device.

The at least one first Type 2 device and/or a subset of the at least one first Type 2 device may be a subset of the at least one second Type 2 device. The at least one second Type 2 device and/or a subset of the at least one second Type 2 device may be a subset of the at least one first Type 2 device.

The at least one first Type 2 device and/or a subset of the at least one first Type 2 device may be a permutation of a subset of the at least one second Type 2 device. The at least one second Type 2 device and/or a subset of the at least one second Type 2 device may be a permutation of a subset of the at least one first Type 2 device.

The at least one second Type 2 device and/or a subset of the at least one second Type 2 device may be at same respective location as a subset of the at least one first Type 2 device. The at least one first Type 2 device and/or a subset of the at least one first Type 2 device may be at same respective location as a subset of the at least one second Type 2 device.

The antenna of the Type 1 device and the antenna of the second Type 1 device may be at same location in the venue. Antenna(s) of the at least one second Type 2 device and/or antenna(s) of a subset of the at least one second Type 2 device may be at same respective location as respective antenna(s) of a subset of the at least one first Type 2 device. Antenna(s) of the at least one first Type 2 device and/or antenna(s) of a subset of the at least one first Type 2 device may be at same respective location(s) as respective antenna(s) of a subset of the at least one second Type 2 device.

A first section of a first time duration of the first CI time series and a second section of a second time duration of the second section of the second CI time series may be aligned. A map between items of the first section and items of the second section may be computed.

The first CI time series may be processed by a first operation.

The second CI time series may be processed by a second operation.

The first operation and/or the second operation may comprise at least one of: subsampling, re-sampling, interpolation, filtering, transformation, feature extraction, pre-processing, and/or another operation.

A first item of the first section may be mapped to a second item of the second section. The first item of the first section may also be mapped to another item of the second section. Another item of the first section may also be mapped to the second item of the second section. The mapping may be one-to-one, one-to-many, many-to-one, many-to-many.

At least one function of at least one of: the first item of the first section of the first CI time series, another item of the first CI time series, a time stamp of the first item, a time difference of the first item, a time differential of the first item, a neighboring time stamp of the first item, another time stamp associated with the first item, the second item of the second section of the second CI time series, another item of the second CI time series, a time stamp of the second item, a time difference of the second item, a time differential of the second item, a neighboring time stamp of the second item, and another time stamp associated with the second item, may satisfy at least one constraint.

One constraint may be that a difference between the time stamp of the first item and the time stamp of the second item may be upper-bounded by an adaptive upper threshold and lower-bounded by an adaptive lower threshold.

The first section may be the entire first CI time series. The second section may be the entire second CI time series. The first time duration may be equal to the second time duration.

A section of a time duration of a CI time series may be determined adaptively. A tentative section of the CI time series may be computed. A starting time and an ending time of a section (e.g. the tentative section, the section) may be determined. The section may be determined by removing a beginning portion and an ending portion of the tentative section.

A beginning portion of a tentative section may be determined as follows. Iteratively, items of the tentative section with increasing time stamp may be considered as a current item, one item at a time.

In each iteration, at least one activity measure may be computed and/or considered. The at least one activity measure may be associated with at least one of: the current item associated with a current time stamp, past items of the tentative section with time stamps not larger than the current time stamp, and/or future items of the tentative section with time stamps not smaller than the current time stamp. The current item may be added to the beginning portion of the tentative section if at least one criterion associated with the at least one activity measure is satisfied.

The at least one criterion associated with the activity measure may comprise at least one of: (a) the activity measure is smaller than an adaptive upper threshold, (b) the activity measure is larger than an adaptive lower threshold, (c) the activity measure is smaller than an adaptive upper threshold consecutively for at least a predetermined amount of consecutive time stamps, (d) the activity measure is larger than an adaptive lower threshold consecutively for at least another predetermined amount of consecutive time stamps, (e) the activity measure is smaller than an adaptive upper threshold consecutively for at least a predetermined percentage of the predetermined amount of consecutive time stamps, (f) the activity measure is larger than an adaptive lower threshold consecutively for at least another predetermined percentage of the another predetermined amount of consecutive time stamps, (g) another activity measure associated with another time stamp associated with the current time stamp is smaller than another adaptive upper threshold and larger than another adaptive lower threshold, (h) at least one activity measure associated with at least one respective time stamp associated with the current time stamp is smaller than respective upper threshold and larger than respective lower threshold, (i) percentage of time stamps with associated activity measure smaller than respective upper threshold and larger than respective lower threshold in a set of time stamps associated with the current time stamp exceeds a threshold, and (j) another criterion.

An activity measure associated with an item at time $T1$ may comprise at least one of: (1) a first function of the item at time $T1$ and an item at time $T1-D1$, wherein $D1$ is a pre-determined positive quantity (e.g. a constant time offset), (2) a second function of the item at time $T1$ and an item at time $T1+D1$, (3) a third function of the item at time $T1$ and an item at time $T2$, wherein $T2$ is a pre-determined quantity (e.g. a fixed initial reference time; $T2$ may be changed over time; $T2$ may be updated periodically; $T2$ may be the beginning of a time period and $T1$ may be a sliding time in the time period), and (4) a fourth function of the item at time $T1$ and another item.

At least one of: the first function, the second function, the third function, and/or the fourth function may be a function (e.g. $F(X, Y, \ldots)$) with at least two arguments: $X$ and $Y$.

The two arguments may be scalars. The function (e.g. F) may be a function of at least one of: $X$, $Y$, $(X-Y)$, $(Y-X)$, $abs(X-Y)$, $X^a$, $Y^b$, $abs(X^a-Y^b)$, $(X-Y)^a$, $(X/Y)$, $(X+a)/(Y+b)$, $(X^a/Y^b)$, and $((X/Y)^a-b)$, wherein a and b are may be some predetermined quantities. For example, the function may simply be $abs(X-Y)$, or $(X-Y)^2$, $(X-Y)^4$. The function may be a robust function. For example, the function may be $(X-Y)^2$ when $abs(X-Y)$ is less than a threshold T, and $(X-Y)+a$ when $abs(X-Y)$ is larger than T. Alternatively, the function may be a constant when $abs(X-Y)$ is larger than T. The function may also be bounded by a slowly increasing function when $abs(X-y)$ is larger than T, so that outliers cannot severely affect the result. Another example of the function may be $(abs(X/Y)-a)$, where $a=1$. In this way, if $X=Y$ (i.e. no change or no activity), the function will give a value of 0. If X is larger than Y, (X/Y) will be larger than 1 (assuming X and Y are positive) and the function will be positive. And if X is less than Y, (X/Y) will be smaller than 1 and the function will be negative.

In another example, both arguments X and Y may be n-tuples such that $X=(x\_1, x\_2, \ldots, x\_n)$ and $Y=(y\_1, y\_2, \ldots, y\_n)$. The function may be a function of at least one of: x_i, y_i (x_i−y_i), (y_i−x_i), abs(x_i−y_i), x_i^a, y_i^b, abs(x_i^a−y_i^b), (x_i−y_i)^a, (x_i/y_i), (x_i+a)/(y_i+b), (x_i^a/y_i^b), and ((x_i/y_i)^a−b), wherein i is a component index of the n-tuple X and Y, and 1<=i<=n. E.g. component index of x_1 is i=1, component index of x_2 is i=2.

The function may comprise a component-by-component summation of another function of at least one of the following: x_i, y_i, (x_i—y_i), (y_i−x_i), abs(x_i−y_i), x_i^a, y_i^b, abs(x_i^a−y_i^b), (x_i−y_i)^a, (x_i/y_i), (x_i+a)/(y^i+b), (x_i^a/y_i^b), and ((x_i/y_i)^a−b), wherein i is the component index of the n-tuple X and Y. For example, the function may be in a form of sum {i=1}^n (abs(x_i/y_i)−1)/n, or sum_{i=1}^n w_i*(abs(x_i/y_i)−1), where w_i is some weight for component i.

The map may be computed using dynamic time warping (DTW). The DTW may comprise a constraint on at least one of: the map, the items of the first CI time series, the items of the second CI time series, the first time duration, the second time duration, the first section, and/or the second section. Suppose in the map, the i^{th} domain item is mapped to the j^{th} range item. The constraint may be on admissible combination of i and j (constraint on relationship between i and j).

Mismatch cost between a first section of a first time duration of a first CI time series and a second section of a second time duration of a second CI time series may be computed.

The first section and the second section may be aligned such that a map comprising more than one links may be established between first items of the first CI time series and second items of the second CI time series. With each link, one of the first items with a first time stamp may be associated with one of the second items with a second time stamp.

A mismatch cost between the aligned first section and the aligned second section may be computed. The mismatch cost may comprise a function of: an item-wise cost between a first item and a second item associated by a particular link of the map, and a link-wise cost associated with the particular link of the map.

The aligned first section and the aligned second section may be represented respectively as a first vector and a second vector of same vector length. The mismatch cost may comprise at least one of: an inner product, an inner-product-like quantity, a quantity based on correlation, a quantity based on covariance, a discriminating score, a distance, a Euclidean distance, an absolute distance, an Lk distance (e.g. L1, L2, . . . ), a weighted distance, a distance-like quantity and/or another similarity value, between the first vector and the second vector. The mismatch cost may be normalized by the respective vector length.

A parameter derived from the mismatch cost between the first section of the first time duration of the first CI time series and the second section of the second time duration of the second CI time series may be modeled with a statistical distribution. At least one of: a scale parameter, a location parameter and/or another parameter, of the statistical distribution may be estimated.

The first section of the first time duration of the first CI time series may be a sliding section of the first CI time series. The second section of the second time duration of the second CI time series may be a sliding section of the second CI time series.

A first sliding window may be applied to the first CI time series and a corresponding second sliding window may be applied to the second CI time series. The first sliding window of the first CI time series and the corresponding second sliding window of the second CI time series may be aligned.

Mismatch cost between the aligned first sliding window of the first CI time series and the corresponding aligned second sliding window of the second CI time series may be computed. The current event may be associated with at least one of: the known event, the unknown event and/or the another event, based on the mismatch cost.

The classifier may be applied to at least one of: each first section of the first time duration of the first CI time series, and/or each second section of the second time duration of the second CI time series, to obtain at least one tentative classification results. Each tentative classification result may be associated with a respective first section and a respective second section.

The current event may be associated with at least one of: the known event, the unknown event and/or the another event, based on the mismatch cost.

The current event may be associated with at least one of: the known event, the unknown event and/or the another event, based on a largest number of tentative classification results in more than one sections of the first CI time series and corresponding more than sections of the second CI time series. For example, the current event may be associated with a particular known event if the mismatch cost points to the particular known event for N consecutive times (e.g. N=10). In another example, the current event may be associated with a particular known event if the percentage of mismatch cost within the immediate past N consecutive N pointing to the particular known event exceeds a certain threshold (e.g. >80%).

In another example, the current event may be associated with a known event that achieves smallest mismatch cost for the most times within a time period. The current event may be associated with a known event that achieves smallest overall mismatch cost, which is a weighted average of at least one mismatch cost associated with the at least one first sections. The current event may be associated with a particular known event that achieves smallest of another overall cost.

The current event may be associated with the "unknown event" if none of the known events achieve mismatch cost lower than a first threshold T1 in a sufficient percentage of the at least one first section. The current event may also be associated with the "unknown event" if none of the events achieve an overall mismatch cost lower than a second threshold T2.

The current event may be associated with at least one of: the known event, the unknown event and/or the another event, based on the mismatch cost and additional mismatch cost associated with at least one additional section of the first CI time series and at least one additional section of the second CI time series.

The known events may comprise at least one of: a door closed event, a door open event, a window closed event, a window open event, a multi-state event, an on-state event, an off-state event, an intermediate state event, a continuous state event, a discrete state event, a human-present event, a human-absent event, a sign-of-life-present event, and/or a sign-of-life-absent event.

A projection for each CI may be trained using a dimension reduction method based on the training CI time series. The dimension reduction method may comprise at least one of: principal component analysis (PCA), PCA with different kernel, independent component analysis (ICA), Fisher linear discriminant, vector quantization, supervised learning, unsupervised learning, self-organizing maps, auto-encoder, neural network, deep neural network, and/or another method. The projection may be applied to at least one of: the training CI time series associated with the at least one event, and/or the current CI time series, for the at least one classifier.

The at least one classifier of the at least one event may be trained based on the projection and the training CI time series associated with the at least one event. The at least one current CI time series may be classified based on the projection and the current CI time series.

The projection may be re-trained using at least one of: the dimension reduction method, and another dimension reduction method, based on at least one of: the projection before the re-training, the training CI time series, at least one current CI time series before retraining the projection, and/or additional training CI time series.

The another dimension reduction method may comprise at least one of: a simplified dimension reduction method, principal component analysis (PCA), PCA with different kernels, independent component analysis (ICA), Fisher linear discriminant, vector quantization, supervised learning, unsupervised learning, self-organizing maps, auto-encoder, neural network, deep neural network, and/or yet another method, The at least one classifier of the at least one event may be re-trained based on at least one of: the re-trained projection, the training CI time series associated with the at least one events, and/or at least one current CI time series.

The at least one current CI time series may be classified based on: the re-trained projection, the re-trained classifier, and/or the current CI time series.

Each CI may comprise a vector of complex values. Each complex value may be preprocessed to give the magnitude of the complex value. Each CI may be preprocessed to give a vector of non-negative real numbers comprising the magnitude of corresponding complex values.

Each training CI time series may be weighted in the training of the projection.

The projection may comprise more than one projected components. The projection may comprise at least one most significant projected component. The projection may comprise at least one projected component that may be beneficial for the at least one classifier.

The channel information (CI) may be associated with/may comprise signal strength, signal amplitude, signal phase, received signal strength indicator (RSSI), channel state information (CSI), a channel impulse response (CIR), a channel frequency response (CFR). The CI may be associated with information associated with a frequency band, a frequency signature, a frequency phase, a frequency amplitude, a frequency trend, a frequency characteristics, a frequency-like characteristics, a time domain element, a frequency domain element, a time-frequency domain element, an orthogonal decomposition characteristics, and/or a non-orthogonal decomposition characteristics of the wireless signal through the wireless multipath channel.

The CI may also be associated with information associated with a time period, a time signature, a time stamp, a time amplitude, a time phase, a time trend, and/or a time characteristics of the wireless signal. The CI may be associated with information associated with a time-frequency partition, a time-frequency signature, a time-frequency amplitude, a time-frequency phase, a time-frequency trend, and/or a time-frequency characteristics of the wireless signal. The CI may be associated with a decomposition of the wireless signal. The CI may be associated with information associated with a direction, an angle of arrival (AoA), an angle of a directional antenna, and/or a phase of the wireless signal through the wireless multipath channel. The CI may be associated with attenuation patterns of the wireless signal through the wireless multipath channel. Each CI may be associated with a Type 1 device and a Type 2 device. Each CI may be associated with an antenna of the Type 1 device and an antenna of the Type 2 device.

The channel information (CI) may be obtained from a communication hardware that is capable of providing the CI. The communication hardware may be a WiFi-capable chip/IC (integrated circuit), a chip compliant with a 802.11 or 802.16 or another wireless/radio standard, a next generation WiFi-capable chip, a LTE-capable chip, a 5G-capable chip, a 6G/7G/8G-capable chip, a Bluetooth-enabled chip, a BLE (Bluetooth low power)-enabled chip, a UWB chip, another communication chip (e.g. Zigbee, WiMax, mesh network), etc. The communication hardware computes the CI and stores the CI in a buffer memory and make the CI available for extraction. The CI may comprise data and/or at least one matrices related to channel state information (CSI). The at least one matrices may be used for channel equalization, and/or beam forming, etc.

The wireless multipath channel may be associated with a venue. The attenuation may be due to signal propagation in the venue, signal propagating/reflection/refraction/diffraction through/at/around air (e.g. air of venue), refraction medium/reflection surface such as wall, doors, furniture, obstacles and/or barriers, etc. The attenuation may be due to reflection at surfaces and obstacles (e.g. reflection surface, obstacle) such as floor, ceiling, furniture, fixtures, objects, people, pets, etc.

Each CI may be associated with a time stamp. Each CI may comprise N1 components (e.g. N1 frequency domain components in CFR, N1 time domain components in CIR, or N1 decomposition components). Each component may be associated with a component index. Each component may be a real quantity, an imaginary quantity, a complex quantity, a magnitude, a phase, a flag, and/or a set. Each CI may comprise a vector of complex numbers, a matrix of complex numbers, a set of mixed quantities, and/or a multi-dimensional collection of at least one complex numbers.

Components of a CI time series associated with a particular component index may form a respective component time series associated with the respective index. A CI time series may be divided into N1 component time series. Each respective component time series is associated with a respective component index. The characteristics/spatial-temporal information of the motion of the object may be monitored based on the component time series.

A component-wise characteristics of a component-feature time series of a CI time series may be computed. The component-wise characteristics may be a scalar (e.g. energy) or a function with a domain and a range (e.g. an autocorrelation function, a transform, an inverse transform). The characteristics/spatial-temporal information of the motion of the object may be monitored based on the component-wise characteristics.

A total characteristics of the CI time series may be computed based on the component-wise characteristics of each component time series of the CI time series. The total characteristics may be a weighted average of the component-wise characteristics. The characteristics/spatial-temporal information of the motion of the object may be monitored based on the total characteristics.

The Type 1 device and Type 2 device may support WiFi, WiMax, 3G/beyond 3G, 4G/beyond 4G, LTE, 5G, 6G, 7G, Bluetooth, BLE, Zigbee, a proprietary wireless system, and/or another wireless system.

A common wireless system and/or a common wireless channel may be shared by the Type 1 transceiver and/or the at least one Type 2 transceiver. The at least one Type 2 transceiver may transmit respective wireless signal contemporaneously using the common wireless system and/or the common wireless channel. The Type 1 transceiver may transmit a wireless signal to the at least one Type 2 transceiver using the common wireless system and/or the common wireless channel.

A Type 1 device may temporarily function as a Type 2 device, and vice versa.

Each Type 1 device and Type 2 device may have at least one transmitting/receiving antenna. Each CI may be associated with one of the transmitting antenna of the Type 1 device and one of the receiving antenna of the Type 2 device.

The at least one time series of CI may correspond to various antenna pairs between the Type 1 device and the Type 2 device. The Type 1 device may have at least one antenna. The Type 2 device may also have at least one antenna. Each time series of CI may be associated with an antenna of the Type 1 device and an antenna of the Type 2 device. Averaging or weighted averaging over antenna links may be performed. The averaging or weighted averaging may be over the at least one time series of CI. The averaging may optionally be performed on a subset of the at least one time series of CI corresponding to a subset of the antenna pairs.

Time stamps of CI of a portion of a time series of CI may be irregular and may be corrected so that corrected timestamps of time-corrected CI may be uniformly spaced in time. In the case of multiple Type 1 devices and/or multiple Type 2 devices, the corrected time stamp may be with respect to the same or different clock.

An original timestamp associated with each of the CI may be determined. The original timestamp may not be uniformly spaced in time. Original timestamps of all CI of the particular portion of the particular time series of CI in the current sliding time window may be corrected so that corrected timestamps of time-corrected CI may be uniformly spaced in time.

The characteristics and/or spatial-temporal information may comprise: a location, a position (e.g. initial position, new position), a position on a map, a height, a horizontal location, a vertical location, a distance, a displacement, a speed, an acceleration, a rotational speed, a rotational acceleration, an angle of motion, direction of motion, rotation, a path, deformation, transformation, shrinking, expanding, a gait, a gait cycle, a head motion, a repeated motion, a periodic motion, a pseudo-periodic motion, an impulsive motion, a sudden motion, a fall-down motion, a transient motion, a behavior, a transient behavior, a period of motion, a frequency of motion, a time trend, a temporal profile, a temporal characteristics, an occurrence, a change, a change in frequency, a change in timing, a change of gait cycle, a timing, a starting time, an ending time, a duration, a history of motion, a motion type, a motion classification, a frequency, a frequency spectrum, a frequency characteristics, a presence, an absence, a proximity, an approaching, a receding, an identity of the object, a composition of the object, a head motion rate, a head motion direction, a mouth-related rate, an eye-related rate, a breathing rate, a heart rate, a hand motion rate, a hand motion direction, a leg motion, a body motion, a walking rate, a hand motion rate, a positional characteristics, a characteristics associated with movement of the object, a tool motion, a machine motion, a complex motion, and/or a combination of multiple motions, an event and/or another information. The processor shares computational workload with the Type 1 heterogeneous wireless device and Type 2 heterogeneous wireless device.

The Type 1 device and/or Type 2 device may be a local device. The local device may be: a smart phone, a smart device, TV, sound bar, set-top box, access point, router, repeater, remote control, speaker, fan, refrigerator, microwave, oven, coffee machine, hot water pot, utensil, table, chair, light, lamp, door lock, camera, microphone, motion sensor, security device, fire hydrant, garage door, switch, power adapter, computer, dongle, computer peripheral, electronic pad, sofa, tile, accessory, smart home device, smart vehicle device, smart office device, smart building device, smart manufacturing device, smart watch, smart glasses, smart clock, smart television, smart oven, smart refrigerator, smart air-conditioner, smart chair, smart table, smart accessory, smart utility, smart appliance, smart machine, smart vehicle, an internet-of-thing (IoT) device, an internet-enabled device, a computer, a portable computer, a tablet, a smart house, a smart office, a smart building, a smart parking lot, a smart system, and/or another device.

Each Type 1 device may be associated with a respective identify (ID). Each Type 2 device may also be associated with a respective identify (ID). The ID may comprise: a numeral, a combination of text and numbers, a name, a password, an account, an account ID, a web link, a web address, index to some information, and/or another ID. The ID may be assigned. The ID may be assigned by hardware (e.g. hardwired, via a dongle and/or other hardware), software and/or firmware. The ID may be stored (e.g. in a database, in memory, in a server, in the cloud, stored locally, stored remotely, stored permanently, stored temporarily) and may be retrieved. The ID may be associated with at least one record, account, user, household, address, phone number, social security number, customer number, another ID, time stamp, and/or collection of data. The ID and/or part of the ID of a Type 1 device may be made available to a Type 2 device. The ID may be used for registration, initialization, communication, identification, verification, detection, recognition, authentication, access control, cloud access, networking, social networking, logging, recording, cataloging, classification, tagging, association, pairing, transaction, electronic transaction, and/or intellectual property control, by the Type 1 device and/or the Type 2 device.

The object may be a person, passenger, child, older person, baby, sleeping baby, baby in a vehicle, patient, worker, high-value worker, expert, specialist, waiter, customer in a mall, traveler in airport/train station/bus terminal/shipping terminals, staff/worker/customer service personnel in a factory/mall/supermarket/office/workplace, serviceman in sewage/air ventilation system/lift well, lifts in lift wells, elevator, inmate, people to be tracked/monitored, animal, a plant, a living object, a pet, dog, cat, smart phone, phone accessory, computer, tablet, portable computer, dongle, computing accessory, networked devices, WiFi devices, IoT devices, smart watch, smart glasses, smart devices, speaker, keys, smart key, wallet, purse, handbag, backpack, goods, cargo, luggage, equipment, motor, machine, air conditioner, fan, air conditioning equipment, light fixture, moveable light, television, camera, audio and/or video equipment, stationary, surveillance equipment, parts, signage, tool, cart, ticket, parking ticket, toll ticket, airplane ticket, credit card, plastic card, access card, food packaging, utensil, table, chair, cleaning equipment/tool, vehicle, car, cars in parking facilities, merchandise in a warehouse/store/supermarket/distribution center, boat, bicycle, airplane, drone, remote control car/plane/boat, robot, manufacturing device, assembly line, material/unfinished part/robot/wagon/transports on a factory floor, object to be tracked in airport/shopping mart/supermarket, non-object, absence of an object, presence of an object, object with a form, object with a changing form, object with no form, mass of fluid, mass of liquid, mass of gas/smoke, fire, flame, electromagnetic (EM) source, EM medium, and/or another object.

The object itself may be communicatively coupled with some network, such as WiFi, MiFi, 3G/4G/LTE/5G, Bluetooth, BLE, WiMax, Zigbee, mesh network, adhoc network, and/or other network. The object itself may be bulky with AC power supply, but is moved during installation, cleaning, maintenance, renovation, etc. It may also be installed in a moveable platform such as a lift, a pad, a movable, platform, an elevator, a conveyor belt, a robot, a drone, a forklift, a car, a boat, a vehicle, etc.

The object may have multiple parts, each part with different movement. For example, the object may be a person walking forward. While walking, his left hand and right hand may move in different direction, with different instantaneous speed, acceleration, motion, etc.

The wireless transmitter (e.g. Type 1 device), the wireless receiver (e.g. Type 2 device), another wireless transmitter and/or another wireless receiver may move with the object and/or another object (e.g. in prior movement, current movement and/or future movement. They may be communicatively coupled to one or more nearby device. They may transmit time series of CI and/or information associated with the time series of CI to the nearby device, and/or each other. They may be with the nearby device.

The wireless transmitter and/or the wireless receiver may be part of a small (e.g. coin-size, cigarette box size, or even smaller), light-weight portable device. The portable device may be wirelessly coupled with a nearby device.

The nearby device may be smart phone, iPhone, Android phone, smart device, smart appliance, smart vehicle, smart gadget, smart TV, smart refrigerator, smart speaker, smart watch, smart glasses, smart pad, iPad, computer, wearable computer, notebook computer, gateway. The nearby device may be connected to a cloud server, a local server and/or other server via internet, wired internet connection and/or wireless internet connection. The nearby device may be portable.

The portable device, the nearby device, a local server and/or a cloud server may share the computation and/or storage for a task (e.g. obtain time series of CI, determine characteristics/spatial-temporal information of the object associated with the movement of the object, computation of time series of power information, determining/computing the particular function, searching for local extremum, classification, identifying particular value of time offset, denoising, processing, simplification, cleaning, wireless smart sensing task, extract CI from wireless signal, switching, segmentation, estimate trajectory, process the map, correction, corrective adjustment, adjustment, map-based correction, detecting error, checking for boundary hitting, thresholding, etc.) and information (e.g. time series of CI).

The nearby device may/may not move with the object. The nearby device may be portable/not portable/moveable/non-moveable. The nearby device may use battery power, solar power, AC power and/or other power source. The nearby device may have replaceable/non-replaceable battery, and/or rechargeable/non-rechargeable battery. The nearby device may be similar to the object. The nearby device may have identical (and/or similar) hardware and/or software to the object. The nearby device may be a smart device, a network enabled device, a device with connection to WiFi/3G/4G/5G/6G/Zigbee/Bluetooth/adhoc network/other network, a smart speaker, a smart watch, a smart clock, a smart appliance, a smart machine, a smart equipment, a smart tool, a smart vehicle, an internet-of-thing (IoT) device, an internet-enabled device, a computer, a portable computer, a tablet, and another device.

The nearby device and/or at least one processor associated with the wireless receiver, the wireless transmitter, the another wireless receiver, the another wireless transmitter and/or a cloud server (in the cloud) may determine the initial spatial-temporal information of the object. Two or more of them may determine the initial spatial-temporal info jointly. Two or more of them may share intermediate information in the determination of the initial spatial-temporal information (e.g. initial position).

In one example, the wireless transmitter (e.g. Type 1 device, or Tracker Bot) may move with the object. The wireless transmitter may send the wireless signal to the wireless receiver (e.g. Type 2 device, or Origin Register) or determining the initial spatial-temporal information (e.g. initial position) of the object. The wireless transmitter may also send the wireless signal and/or another wireless signal to another wireless receiver (e.g. another Type 2 device, or another Origin Register) for the monitoring of the motion (spatial-temporal info) of the object. The wireless receiver may also receive the wireless signal and/or another wireless signal from the wireless transmitter and/or the another wireless transmitter for monitoring the motion of the object. The location of the wireless receiver and/or the another wireless receiver may be known.

In another example, the wireless receiver (e.g. Type 2 device, or Tracker Bot) may move with the object. The wireless receiver may receive the wireless signal transmitted from the wireless transmitter (e.g. Type 1 device, or Origin Register) for determining the initial spatial-temporal info (e.g. initial position) of the object. The wireless receiver may also receive the wireless signal and/or another wireless signal from another wireless transmitter (e.g. another Type 1 device, or another Origin Register) for the monitoring of the current motion (e.g. spatial-temporal info) of the object. The wireless transmitter may also transmit the wireless signal and/or another wireless signal to the wireless receiver and/or the another wireless receiver (e.g. another Type 2 device, or another Tracker Bot) for monitoring the motion of the object. The location of the wireless transmitter and/or the another wireless transmitter may be known.

The venue may be a space such as a room, a house, an office, a workplace, a hallway, a walkway, a lift, a lift well, an escalator, an elevator, a sewage system, air ventilations system, a staircase, a gathering area, a duct, an air duct, a pipe, a tube, an enclosed structure, a semi-enclosed structure, an enclosed area, an area with at least one wall, a plant, a machine, an engine, a structure with wood, a structure with glass, a structure with metal, a structure with walls, a structure with doors, a structure with gaps, a structure with reflection surface, a structure with fluid, a building, a roof top, a store, a factory, an assembly line, a hotel room, a museum, a classroom, a school, a university, a government building, a warehouse, a garage, a mall, an airport, a train station, a bus terminal, a hub, a transportation hub, a shipping terminal, a government facility, a public facility, a school, a university, an entertainment facility, a recreational facility, a hospital, a seniors home, an elderly care facility, a community center, a stadium, a playground, a park, a field, a sports facility, a swimming facility, a track and/or field, a basketball court, a tennis court, a soccer stadium, a baseball stadium, a gymnasium, a hall, a garage, a shopping mart, a mall, a supermarket, a manufacturing facility, a parking facility, a construction site, a mining facility, a transportation facility, a highway, a road, a valley, a forest, a wood, a terrain, a landscape, a den, a patio, a land, a path, an amusement park, an urban area, a rural area, a suburban area, a metropolitan area, a garden, a square, a plaza, a music hall, a downtown facility, an over-air facility, a semi-open facility, a closed area, a train platform, a train station, a distribution center, a warehouse, a store, a distribution center, a storage facility, an underground facility, a space (e.g. above ground, outer-space) facility, a floating facility, a cavern, a tunnel facility, an indoor facility, an open-air facility, an outdoor facility with some walls/doors/reflective barriers, an open facility, a semi-open facility, a car, a truck, a bus, a van, a container, a ship/boat, a submersible, a train, a tram, an airplane, a vehicle, a mobile home, a cave, a tunnel, a pipe, a channel, a metropolitan area, downtown area with relatively tall buildings, a valley, a well, a duct, a pathway, a gas line, an oil line, a water pipe, a network of interconnecting pathways/alleys/roads/tubes/cavities/caves/pipe-like structure/air space/fluid space, a human body, an animal body, a body cavity, an organ, a bone, a teeth, a soft tissue, a hard tissue, a rigid tissue, a non-rigid tissue, a blood/body fluid vessel, windpipe, air duct, a den, etc. The venue may be an indoor space, an outdoor space, The venue may include both the inside and outside of the space. For example, the venue may include both the inside of a building and the outside of the building. For example, the venue can be a building that has one floor or multiple floors, and a portion of the building can be underground. The shape of the building can be, e.g., round, square, rectangular, triangle, or irregular-shaped. These are merely examples. The disclosure can be used to detect events in other types of venue or spaces.

The wireless transmitter (e.g. Type 1 device) and/or the wireless receiver (e.g. Type 2 device) may be embedded in a portable device (e.g. a module, or a device with the module) that may move with the object (e.g. in prior movement and/or current movement). The portable device may be communicatively coupled with the object using a wired connection (e.g. through USB, microUSB, Firewire, HDMI, serial port, parallel port, and other connectors) and/or a wireless connection (e.g. Bluetooth, Bluetooth Low Energy (BLE), WiFi, LTE, ZigBee, etc.). The portable device may be a lightweight device. The portable may be powered by battery, rechargeable battery and/or AC power. The portable device may be very small (e.g. at sub-millimeter scale and/or sub-centimeter scale), and/or small (e.g. coin-size, card-size, pocket-size, or larger). The portable device may be large, sizable, and/or bulky (e.g. heavy machinery to be installed). The portable device may be a WiFi hotspot, an access point, a mobile WiFi (MiFi), a dongle with USB/micro USB/Firewlire/other connector, a smartphone, a portable computer, a computer, a tablet, a smart device, an internet-of-thing (IoT) device, a WiFi-enabled device, an LTE-enabled device, a smart watch, a smart glass, a smart mirror, a smart antenna, a smart battery, a smart light, a smart pen, a smart ring, a smart door, a smart window, a smart clock, a small battery, a smart wallet, a smart belt, a smart handbag, a smart clothing/garment, a smart ornament, a smart packaging, a smart paper/book/magazine/poster/printed matter/signage/display/lighted system/lighting system, a smart key/tool, a smart bracelet/chain/necklace/wearable/accessory, a smart pad/cushion, a smart tile/block/brick/building material/other material, a smart garbage can/waste container, a smart food carriage/storage, a smart ball/racket, a smart chair/sofa/bed, a smart shoe/footwear/carpet/mat/shoe rack, a smart glove/hand wear/ring/hand ware, a smart hat/headwear/makeup/sticker/tattoo, a smart mirror, a smart toy, a smart pill, a smart utensil, a smart bottle/food container, a smart tool, a smart device, an IoT device, a WiFi enabled device, a network enabled device, a 3G/4G/5G/6G enabled device, an embeddable device, an implantable device, air conditioner, refrigerator, heater, furnace, furniture, oven, cooking device, television/set-top box (STB)/DVD player/audio player/video player/remote control, hi-fi, audio device, speaker, lamp/light, wall, door, window, roof, roof tile/shingle/structure/attic structure/device/feature/installation/fixtures, lawn mower/garden tools/yard tools/mechanics tools/garage tools, garbage can/container, 20-ft/40-ft container, storage container, factory/manufacturing/production device, repair tools, fluid container, machine, machinery to be installed, a vehicle, a cart, a wagon, warehouse vehicle, a car, a bicycle, a motorcycle, a boat, a vessel, an airplane, a basket/box/bag/bucket/container, a smart plate/cup/bowl/pot/mat/utensils/kitchen tools/kitchen devices/kitchen accessories/cabinets/tables/chairs/tiles/lights/water pipes/taps/gas range/oven/dishwashing machine/etc. The portable device may have a battery that may be replaceable, irreplaceable, rechargeable, and/or non-rechargeable. The portable device may be wirelessly charged. The portable device may be a smart payment card. The portable device may be a payment card used in parking lots, highways, entertainment parks, or other venues/facilities that need payment. The portable device may have an identity (ID) as described above.

An event may be monitored based on the time series of CI. The event may be an object related event, such as fall-down of the object (e.g. an person and/or a sick person), a rotation, a hesitation, a pause, an impact (e.g. a person hitting a sandbag, a door, a window, a bed, a chair, a table, a desk, a cabinet, a box, another person, an animal, a bird, a fly, a table, a chair, a ball, a bowling ball, a tennis ball, a football, a soccer ball, a baseball, a basketball, a volley ball, etc.), a two-body action (e.g. a person letting go a balloon, catching a fish, molding a clay, writing a paper, a person typing on a computer, etc.), a car moving in a garage, a person carrying a smart phone and walking around an airport/mall/government building/office/etc, an autonomous moveable object/machine moving around (e.g. vacuum cleaner, utility vehicle, a car, drone, self-driving car, etc.).

The task or the wireless smart sensing task may comprise: object detection, presence detection, object recognition, object verification, tool detection, tool recognition, tool verification, machine detection, machine recognition, machine verification, human detection, human recognition, human verification, baby detection, baby recognition, baby verification, human breathing detection, motion detection, motion estimation, motion verification, periodic motion detection, periodic motion estimation, periodic motion verification, stationary motion detection, stationary motion estimation, stationary motion verification, cyclo-stationary motion detection, cyclo-stationary motion estimation, cyclo-stationary motion verification, transient motion detection, transient motion estimation, transient motion verification, trend detection, trend estimation, trend verification, breathing detection, breathing estimation, breathing estimation, human biometrics detection, human biometrics estimation, human biometrics verification, environment informatics detection, environment informatics estimation, environment informatics verification, gait detection, gait estimation, gait verification, gesture detection, gesture estimation, gesture verification, machine learning, supervised learning, unsupervised learning, semi-supervised learning, clustering, feature extraction, featuring training, principal component analysis, eigen-decomposition, frequency decomposition, time decomposition, time-frequency decomposition, functional decomposition, other decomposition, training, discriminative training, supervised training, unsupervised training, semi-supervised training, neural network, sudden motion detection, fall-down detection, danger detection, life-threat detection, regular motion detection, stationary motion detection, cyclo-stationary motion detection, intrusion detection, suspicious motion detection, security, safety monitoring, navigation, guidance, map-based processing, map-based correction, irregularity detection, locationing, tracking, multiple object tracking, indoor tracking, indoor position, indoor navigation, power transfer, wireless power transfer, object counting, car tracking in parking garage, patient detection, patient monitoring, patient verification, wireless communication, data communication, signal broadcasting, networking, coordination, administration, encryption, protection, cloud computing, other processing and/or other task. The task may be performed by the Type 1 device, the Type 2 device, another Type 1 device, another Type 2 device, a nearby device, a local server, an edge server, a cloud server, and/or another device.

A first part of the task may comprise at least one of: preprocessing, signal conditioning, signal processing, post-processing, denoising, feature extraction, coding, encryption, transformation, mapping, motion detection, motion estimation, motion change detection, motion pattern detection, motion pattern estimation, motion pattern recognition, vital sign detection, vital sign estimation, vital sign recognition, periodic motion detection, periodic motion estimation, breathing rate detection, breathing rate estimation, breathing pattern detection, breathing pattern estimation, breathing pattern recognition, heart beat detection, heart beat estimation, heart pattern detection, heart pattern estimation, heart pattern recognition, gesture detection, gesture estimation, gesture recognition, speed detection, speed estimation, object locationing, object tracking, navigation, acceleration estimation, acceleration detection, fall-down detection, change detection, intruder detection, baby detection, baby monitoring, patient monitoring, object recognition, wireless power transfer, and/or wireless charging.

A second part of the task may comprise at least one of: a smart home task, a smart office task, a smart building task, a smart factory task (e.g. manufacturing using a machine or an assembly line), a smart internet-of-thing (IoT) task, a smart system task, a smart home operation, a smart office operation, a smart building operation, a smart manufacturing operation (e.g. moving supplies/parts/raw material to a machine/an assembly line), an IoT operation, a smart system operation, turning on a light, turning off the light, controlling the light in at least one of: a room, a region, and/or the venue, playing a sound clip, playing the sound clip in at least one of: the room, the region, and/or the venue, playing the sound clip of at least one of: a welcome, a greeting, a farewell, a first message, and/or a second message associated with the first part of the task, turning on an appliance, turning off the appliance, controlling the appliance in at least one of: the room, the region, and/or the venue, turning on an electrical system, turning off the electrical system, controlling the electrical system in at least one of: the room, the region, and/or the venue, turning on a security system, turning off the security system, controlling the security system in at least one of: the room, the region, and/or the venue, turning on a mechanical system, turning off a mechanical system, controlling the mechanical system in at least one of: the room, the region, and/or the venue, and/or controlling at least one of: an air conditioning system, a heating system, a ventilation system, a lighting system, a heating device, a stove, an entertainment system, a door, a fence, a window, a garage, a computer system, a networked device, a networked system, a home appliance, an office equipment, a lighting device, a robot (e.g. robotic arm), a smart vehicle, a smart machine, an assembly line, a smart device, an internet-of-thing (IoT) device, a smart home device, and/or a smart office device.

The task may include: detect a user returning home, detect a user leaving home, detect a user moving from one room to another, detect/control/lock/unlock/open/close/partially open a window/door/garage door/blind/curtain/panel/solar panel/sun shade, detect a pet, detect/monitor a user doing something (e.g. sleeping on sofa, sleeping in bedroom, running on treadmill, cooking, sitting on sofa, watching TV, eating in kitchen, eating in dining room, going upstairs/downstairs, going outside/coming back, in the rest room, etc.), monitor/detect location of a user/pet, do something automatically upon detection, do something for the user automatically upon detecting the user, turn on/off/dim a light, turn on/off music/radio/home entertainment system, turn on/off/adjust/control TV/HiFi/set-top-box (STB)/home entertainment system/smart speaker/smart device, turn on/off/adjust air conditioning system, turn on/off/adjust ventilation system, turn on/off/adjust heating system, adjust/control curtains/light shades, turn on/off/wake a computer, turn on/off/pre-heat/control coffee machine/hot water pot, turn on/off/control/preheat cooker/oven/microwave oven/ another cooking device, check/adjust temperature, check weather forecast, check telephone message box, check mail, do a system check, control/adjust a system, check/control/arm/disarm security system/baby monitor, check/control refrigerator, give a report (e.g. through a speaker such as Google home, Amazon Echo, on a display/screen, via a webpage/email/messaging system/notification system, etc.).

For example, when a user arrives home in his car, the task may be to, automatically, detect the user or his car approaching, open the garage door upon detection, turn on the driveway/garage light as the user approaches the garage, turn on air conditioner/heater/fan, etc. As the user enters the house, the task may be to, automatically, turn on the entrance light, turn off driveway/garage light, play a greeting message to welcome the user, turn on the music, turn on the radio and tuning to the user's favorite radio news channel, open the curtain/blind, monitor the user's mood, adjust the lighting and sound environment according to the user's mood or the current/imminent event (e.g. do romantic lighting and music because the user is scheduled to eat dinner with girlfriend in 1 hour) on the user's daily calendar, warm the food in microwave that the user prepared in the morning, do a diagnostic check of all systems in the house, check weather forecast for tomorrow's work, check news of interest to the user, check user's calendar and to-do list and play reminder, check telephone answer system/messaging system/email and give a verbal report using dialog system/speech synthesis, remind (e.g. using audible tool such as speakers/HiFi/speech synthesis/sound/voice/music/song/sound field/background sound field/dialog system, using visual tool such as TV/entertainment system/computer/notebook/smart pad/display/light/color/brightness/patterns/symbols, using haptic tool/virtual reality tool/gesture/tool, using a smart device/ appliance/material/furniture/fixture, using web tool/server/cloud server/fog server/edge server/home network/mesh network, using messaging tool/notification tool/communication tool/scheduling tool/email, using user interface/GUI, using scent/smell/fragrance/taste, using neural tool/nervous system tool, using a combination, etc.) the user of his mother's birthday and to call her, prepare a report, and give the report (e.g. using a tool for reminding as discussed above). The task may turn on the air conditioner/heater/ventilation system in advance, or adjust temperature setting of smart thermostat in advance, etc. As the user moves from the entrance to the living room, the task may be to turn on the living room light, open the living room curtain, open the window, turn off the entrance light behind the user, turn on the TV and set-top box, set TV to the user's favorite channel, adjust an appliance according to the user's preference and conditions/states (e.g. adjust lighting and choose/play music to build a romantic atmosphere), etc.

Another example may be: When the user wakes up in the morning, the task may be to detect the user moving around in the bedroom, open the blind/curtain, open the window, turn off the alarm clock, adjust indoor temperature from night-time temperature profile to day-time temperature profile, turn on the bedroom light, turn on the restroom light as the user approaches the restroom, check radio or streaming channel and play morning news, turn on the coffee machine and preheat the water, turn off security system, etc. When the user walks from bedroom to kitchen, the task may be to turn on the kitchen and hallway lights, turn off the bedroom and restroom lights, move the music/message/reminder from the bedroom to the kitchen, turn on the kitchen TV, change TV to morning news channel, lower the kitchen blind and open the kitchen window to bring in fresh air, unlock backdoor for the user to check the backyard, adjust temperature setting for the kitchen, etc.

Another example may be: When the user leaves home for work, the task may be to detect the user leaving, play a farewell and/or have-a-good-day message, open/close garage door, turn on/off garage light and driveway light, turn off/dim lights to save energy (just in case the user forgets), close/lock all windows/doors (just in case the user forgets), turn off appliance (especially stove, oven, microwave oven), turn on/arm the home security system to guard the home against any intruder, adjust air conditioning/heating/ventilation systems to "away-from-home" profile to save energy, send alerts/reports/updates to the user's smart phone, etc.

A motion may comprise at least one of: a no-motion, a resting motion, a non-moving motion, a deterministic motion, a transient motion, a fall-down motion, a repeating motion, a periodic motion, a pseudo-periodic motion, a periodic motion associated with breathing, a periodic motion associated with heartbeat, a periodic motion associated with a living object, a periodic motion associated with a machine, a periodic motion associated with a man-made object, a periodic motion associated with nature, a complex motion with a transient element and a periodic element, a repetitive motion, a non-deterministic motion, a probabilistic motion, a chaotic motion, a random motion, a complex motion with a non-deterministic element and a deterministic element, a stationary random motion, a pseudo-stationary random motion, a cyclo-stationary random motion, a non-stationary random motion, a stationary random motion with a periodic autocorrelation function (ACF), a random motion with a periodic ACF for a period of time, a random motion that is pseudo-stationary for a period of time, a random motion of which an instantaneous ACF has a pseudo-periodic element for a period of time, a machine motion, a mechanical motion, a vehicle motion, a drone motion, an air-related motion, a wind-related motion, a weather-related motion, a water-related motion, a fluid-related motion, an ground-related motion, a change in electro-magnetic characteristics, a sub-surface motion, a seismic motion, a plant motion, an animal motion, a human motion, a normal motion, an abnormal motion, a dangerous motion, a warning motion, a suspicious motion, a rain, a fire, a flood, a tsunami, an explosion, a collision, an imminent collision, a human body motion, a head motion, a facial motion, an eye motion, a mouth motion, a tongue motion, a neck motion, a finger motion, a hand motion, an arm motion, a shoulder motion, a body motion, a chest motion, an abdominal motion, a hip motion, a leg motion, a foot motion, a body joint motion, a knee motion, an elbow motion, an upper body motion, a lower body motion, a skin motion, a below-skin motion, a subcutaneous tissue motion, a blood vessel motion, an intravenous motion, an organ motion, a heart motion, a lung motion, a stomach motion, an intestine motion, a bowel motion, an eating motion, a breathing motion, a facial expression, an eye expression, a mouth expression, a talking motion, a singing motion, an eating motion, a gesture, a hand gesture, an arm gesture, a keystroke, a typing stroke, a user-interface gesture, a man-machine interaction, a gait, a dancing movement, a coordinated movement, and/or a coordinated body movement.

The heterogeneous IC of the Type 1 device and/or any Type 2 receiver may comprise a low-noise amplifier (LNA), a power amplifier, a transmit-receive switch, a media access controller, a baseband radio, a 2.4 GHz radio, a 3.65 GHz radio, a 4.9 GHz radio, a 5 GHz radio, a 5.9 GHz radio, a below 6 GHz radio, a below 60 GHz radio and/or another radio.

The heterogeneous IC may comprise a processor, a memory communicatively coupled with the processor, and a set of instructions stored in the memory to be executed by the processor. The IC may be an application specific integrated circuit (ASIC), a field programmable gate array (FPGA), other programmable logic device, discrete logic, and/or a combination.

The heterogeneous IC may support a broadband network, a wireless network, a mobile network, a mesh network, a cellular network, a wireless local area network (WLAN), a wide area network (WAN), and a metropolitan area network (MAN), a WLAN standard, WiFi, LTE, a 802.11 standard, 802.11a, 802.11b, 802.11g, 802.11n, 802.11ac, 802.11ad, 802.11af, 802.11ah, 802.11ax, 802.11ay, a mesh network standard, a 802.15 standard, a 802.16 standard, a cellular network standard, 3G, 3.5G, 4G, beyond 4G, 4.5G, 5G, 6G, 7G, 8G, 9G, Bluetooth, Bluetooth Low-Energy (BLE), Zigbee, WiMax, and/or another wireless network protocol.

The processor may comprise a general purpose processor, a special purpose processor, a microprocessor, a microcontroller, an embedded processor, a digital signal processor, a central processing unit (CPU), a graphical processing unit (GPU), a multi-processor, a multi-core processor, and/or a processor with graphics capability, and/or a combination.

The memory may be volatile, non-volatile, random access memory (RAM), Read Only Memory (ROM), Electrically Programmable ROM (EPROM), Electrically Erasable Programmable ROM (EEPROM), hard disk, flash memory, CD-ROM, DVD-ROM, a magnetic storage, an optical storage, an organic storage, a storage system, a storage network, network storage, cloud storage, or other form of non-transitory storage medium known in the art.

The set of instructions (machine executable code) corresponding to the method steps may be embodied directly in hardware, in software, in firmware, or in combinations thereof.

The presentation may be a presentation in an audio-visual way, a graphical way (e.g. using GUI), a textual way, a symbolic way or a mechanical way.

Computational workload associated with the method is shared among the processor, the Type 1 heterogeneous wireless device, the Type 2 heterogeneous wireless device, a local server, a cloud server, and another processor.

An operation, a pre-processing, a processing and/or a postprocessing may be applied to data (e.g. time series of CI, autocorrelation). An operation may be preprocessing, processing and/or postprocessing. The preprocessing, processing and/or postprocessing may be an operation. An operation may comprise preprocessing, processing, post-processing, computing a function of the operands, filtering, linear filtering, nonlinear filtering, folding, grouping, energy computation, lowpass filtering, bandpass filtering, highpass filtering, median filtering, rank filtering, quartile filtering, percentile filtering, mode filtering, finite impulse response (FIR) filtering, infinite impulse response (IIR) filtering, moving average (MA) filtering, autoregressive (AR) filtering, autoregressive moving averaging (ARMA) filtering, selective filtering, adaptive filtering, interpolation, decimation, subsampling, upsampling, resampling, time correction, time base correction, phase correction, magnitude correction, phase cleaning, magnitude cleaning, matched filtering, enhancement, restoration, denoising, smoothing, signal conditioning, enhancement, restoration, spectral analysis, linear transform, nonlinear transform, frequency transform, inverse frequency transform, Fourier transform, wavelet transform, Laplace transform, Hilbert transform, Hadamard transform, trigonometric transform, sine transform, cosine transform, power-of-2 transform, sparse transform, graph-based transform, graph signal processing, fast transform, a transform combined with zero padding, cyclic padding, padding, zero padding, feature extraction, decomposition, projection, orthogonal projection, non-orthogonal projection, over-complete projection, eigen-decomposition, singular value decomposition (SVD), principle component analysis (PCA), independent component analysis (ICA), grouping, sorting, thresholding, soft thresholding, hard thresholding, clipping, soft clipping, first derivative, second order derivative, high order derivative, convolution, multiplication, division, addition, subtraction, integration, maximization, minimization, local maximization, local minimization, optimization of a cost function, neural network, recognition, labeling, training, clustering, machine learning, supervised learning, unsupervised learning, semi-supervised learning, comparison with another time series of CI, similarity score computation, quantization, vector quantization, matching pursuit, compression, encryption, coding, storing, transmitting, normalization, temporal normalization, frequency domain normalization, classification, clustering, labeling, tagging, learning, detection, estimation, learning network, mapping, remapping, expansion, storing, retrieving, transmitting, receiving, representing, merging, combining, splitting, tracking, monitoring, matched filtering, Kalman filtering, particle filter, intrapolation, extrapolation, importance sampling, Monte Carlo sampling, compressive sensing, representing, merging, combining, splitting, scrambling, error protection, forward error correction, doing nothing, time varying processing, conditioning averaging, weighted averaging, arithmetic mean, geometric mean, averaging over selected frequency, averaging over antenna links, a logical operation, permutation, combination, sorting, AND, OR, XOR, union, intersection, vector addition, vector subtraction, vector multiplication, vector division, inverse, a norm, a distance, and/or another operation. The operation may be the preprocessing, processing, and/or post-processing. Operations may be applied jointly on multiple time series or functions.

The function (e.g. function of the operands) may comprise: a scalar function, a vector function, a discrete function, a continuous function, a polynomial function, a magnitude, a phase, an exponential function, a logarithmic function, a trigonometric function, a transcendental function, a logical function, a linear function, an algebraic function, a nonlinear function, a piecewise linear function, a real function, a complex function, a vector-valued function, an inverse function, a derivative of a function, an integration of a function, a circular function, a function of another function, a one-to-one function, a one-to-many function, a many-to-one function, a many-to-many function, a zero crossing, absolute function, indicator function, a mean, a mode, a median, a range, a statistics, a variance, a trimmed mean, a percentile, a square, a cube, a root, a power, a sine, a cosine, a tangent, a cotangent, a secant, a cosecant, an elliptical function, a parabolic function, a hyperbolic function, a game function, a zeta function, an absolute value, a thresholding, a quantization, a piecewise constant function, a composite function, a function of function, an input time function processed with an operation (e.g. filtering), a probabilistic function, a stochastic function, a random function, an ergodic function, a stationary function, a deterministic function, a transformation, a frequency transform, an inverse frequency transform, a discrete time transform, Laplace transform, Hilbert transform, sine transform, cosine transform, triangular transform, wavelet transform, integer transform, power-of-2 transform, sparse transform, projection, decomposition, principle component analysis (PCA), independent component analysis (ICA), neural network, feature extraction, a moving function, a function of a moving window of neighboring items of a time series, a filtering function, a convolution, a mean function, a variance function, a statistical function, short-time transform, discrete transform, discrete Fourier transform, discrete cosine transform, discrete sine transform, Hadamard transform, eigen-decomposition, eigenvalue, singular value decomposition (SVD), singular value, orthogonal decomposition, matching pursuit, sparse transform, sparse approximation, any decomposition, graph-based processing, graph-based transform, graph signal processing, classification, labeling, learning, machine learning, detection, estimation, feature extraction, learning network, feature extraction, denoising, signal enhancement, coding, encryption, mapping, remapping, vector quantization, lowpass filtering, highpass filtering, bandpass filtering, matched filtering, Kalman filtering, preprocessing, postprocessing, particle filter, FIR filtering, IIR filtering, autoregressive (AR) filtering, adaptive filtering, first order derivative, high order derivative, integration, zero crossing, smoothing, median filtering, mode filtering, sampling, random sampling, resampling function, downsampling, upsampling, interpolation, extrapolation, importance sampling, Monte Carlo sampling, compressive sensing, statistics, short term statistics, long term statistics, mean, variance, autocorrelation function, cross correlation, moment generating function, time averaging, etc.

Machine learn, training, discriminative training, deep learning, neural network, continuous time processing, distributed computing, distributed storage, acceleration using GPU/DSP/coprocessor/multicore/multiprocessing may be applied to a step (or each step) of this disclosure.

A frequency transform may include Fourier transform, Laplace transform, Hadamard transform, Hilbert transform, sine transform, cosine transform, triangular transform, wavelet transform, integer transform, power-of-2 transform, combined zero padding and transform, Fourier transform with zero padding, and/or another transform. Fast versions and/or approximated versions of the transform may be performed. The transform may be performed using floating point, and/or fixed point arithmetic.

An inverse frequency transform may include inverse Fourier transform, inverse Laplace transform, inverse Hadamard transform, inverse Hilbert transform, inverse sine transform, inverse cosine transform, inverse triangular transform, inverse wavelet transform, inverse integer transform, inverse power-of-2 transform, combined zero padding and transform, inverse Fourier transform with zero padding, and/or another transform. Fast versions and/or approximated versions of the transform may be performed. The transform may be performed using floating point, and/or fixed point arithmetic.

Sliding time window may have time varying window width. It may be smaller at the beginning to enable fast acquisition and may increase over time to a steady-state size. The steady-state size may be related to the frequency, repeated motion, transient motion, and/or spatial-temporal information to be monitored. Even in steady state, the window size may be adaptively changed based on battery life, power consumption, available computing power, a change in amount of targets, the nature of motion to be monitored, etc.

The time shift between two sliding time windows at adjacent time instance may be constant/variable/locally adaptive over time. When shorter time shift is used, the update of any monitoring may be more frequent which may be used for fast changing situations, object motions, and/or objects. Longer time shift may be used for slower situations, object motions, and/or objects.

The window width/size and/or time shift may be changed upon a user request/choice. The time shift may be changed automatically (e.g. as controlled by processor/computer/server/cloud server) and/or adaptively.

At least one characteristics of a function (e.g. auto-correlation function, auto-covariance function, cross-correlation function, cross-covariance function, power spectral density, a time function, a frequency domain function, a frequency transform) may be determined (e.g. by an object tracking server, the processor, the Type 1 heterogeneous device, the Type 2 heterogeneous device, and/or another device). The at least one characteristics of the function may include: a local maximum, a local minimum, a local extremum, a local extremum with positive time offset, a first local extremum with positive time offset, an n^th local extremum with positive time offset, a local extremum with negative time offset, a first local extremum with negative time offset, an n^th local extremum with negative time offset, a constrained (with argument within a constraint) maximum, minimum, constrained maximum, constrained minimum, a constrained extremum, a slope, a derivative, a higher order derivative, a maximum slope, a minimum slope, a local maximum slope, a local maximum slope with positive time offset, a local minimum slope, a constrained maximum slope, a constrained minimum slope, a maximum higher order derivative, a minimum higher order derivative, a constrained higher order derivative, a zero-crossing, a zero crossing with positive time offset, an n^th zero crossing with positive time offset, a zero crossing with negative time offset, an n^th zero crossing with negative time offset, a constrained zero-crossing, a zero-crossing of slope, a zero-crossing of higher order derivative, and/or another characteristics. At least one argument of the function associated with the at least one characteristics of the function may be identified. Some quantity (e.g. a spatial-temporal information of the object) may be determined based on the at least one argument of the function.

A characteristics of a motion of an object in the venue may comprise at least one of: an instantaneous characteristics, a short-term characteristics, repetitive characteristics, a recurring characteristics, a history, an incremental characteristics, a changing characteristics, a deviational characteristics, a phase, a magnitude, a time characteristics, a frequency characteristics, a time-frequency characteristics, a decomposition characteristics, an orthogonal decomposition characteristics, a non-orthogonal decomposition characteristics, a deterministic characteristics, a probabilistic characteristics, a stochastic characteristics, an autocorrelation function (ACF), a mean, a variance, a statistics, a duration, a timing, a trend, a periodic characteristics, a long-term characteristics, a historical characteristics, an average characteristics, a current characteristics, a past characteristics, a future characteristics, a predicted characteristics, a location, a distance, a height, a speed, a direction, a velocity, an acceleration, a change of the acceleration, an angle, an angular speed, an angular velocity, an angular acceleration of the object, a change of the angular acceleration, an orientation of the object, an angular of a rotation, a deformation of the object, a shape of the object, a change of shape of the object, a change of size of the object, a change of structure of the object, and/or a change of characteristics of the object.

At least one local maximum and at least one local minimum of the function may be identified. At least one local signal-to-noise-ratio-like (SNR-like) parameter may be computed for each pair of adjacent local maximum and local minimum. The SNR-like parameter may be a function (e.g. linear, log, exponential function, a monotonic function) of a fraction of a quantity (e.g. power, magnitude, etc.) of the local maximum over the same quantity of the local minimum. It may also be the function of a difference between the quantity of the local maximum and the same quantity of the local minimum.

Significant local peaks may be identified or selected. Each significant local peak may be a local maximum with SNR-like parameter greater than a threshold T1 and/or a local maximum with amplitude greater than a threshold T2.

The at least one local minimum and the at least one local minimum in the frequency domain may be identified/computed using a persistence-based approach.

A set of selected significant local peaks may be selected from the set of identified significant local peaks based on a selection criterion. The characteristics/spatial-temporal information of the object may be computed based on the set of selected significant local peaks and frequency values associated with the set of selected significant local peaks.

In one example, the selection criterion may always correspond to select the strongest peaks in a range. While the strongest peaks may be selected, the unselected peaks may still be significant (rather strong).

Unselected significant peaks may be stored and/or monitored as "reserved" peaks for use in future selection in future sliding time windows. As an example, there may be a particular peak (at a particular frequency) appearing consistently over time. Initially, it may be significant but not selected (as other peaks may be stronger). But in later time, the peak may become stronger and more dominant and may be selected. When it became "selected", it may be back-traced in time and made "selected" in the earlier time when it was significant but not selected. In such case, the back-traced peak may replace a previously selected peak in an early time. The replaced peak may be the relatively weakest, or a peak that appear in isolation in time (i.e. appearing only briefly in time).

In another example, the selection criterion may not correspond to select the strongest peaks in the range. Instead, it may consider not only the "strength" of the peak, but the "trace" of the peak—peaks that may have happened in the past, especially those peaks that have been identified for a long time.

For example, if a finite state machine (FSM) is used, it may select the peak(s) based on the state of the FSM. Decision thresholds may be computed adaptively based on the state of the FSM.

A similarity score may be computed (e.g. by a server, the processor, the Type 1 device, the Type 2 device, a local server, a cloud server, and/or another device) based on a pair of temporally adjacent CI of a time series of CI. The pair may come from the same sliding window or two different sliding windows. The similarity score may also be based on a pair of, temporally adjacent or not so adjacent, CI from two different time series of CI. The similarity score may be or may include: a time reversal resonating strength (TRRS), a correlation, a cross-correlation, an auto-correlation, a covariance, a cross-covariance, an auto-covariance, an inner product of two vectors, a distance score, a discrimination score, a metric, a neural network output, a deep learning network output, and/or another score. The characteristics and/or spatial-temporal information may be determined/computed based on the similarity score.

Any threshold may be pre-determined, adaptively determined and/or determined by a finite state machine. The adaptive determination may be based on time, space, location, antenna, path, link, state, battery life, remaining battery life, available power, available computational resources, available network bandwidth, etc.

A threshold to be applied to a test statistics to differentiate two events (or two conditions, or two situations, or two states), A and B, may be determined. Data (e.g. CI, channel state information (CSI)) may be collected under A and/or under B in a training situation. The test statistics may be computed based on the data. Distributions of the test statistics under A may be compared with distributions of the test statistics under B, and the threshold may be chosen according to some criteria. The criteria may comprise: maximum likelihood (ML), maximum aposterior probability (MAP), discriminative training, minimum type 1 error for a given type 2 error, minimum type 2 error for a given type 1 error, and/or other criteria. The threshold may be adjusted to achieve different sensitivity to the A, B and/or another event/condition/situation/state. The threshold adjustment may be automatic, semi-automatic and/or manual. The threshold adjustment may be applied once, sometimes, often, periodically, occasionally, sporadically, and/or on demand. The threshold adjustment may be adaptive. The threshold adjustment may depend on the object, an object movement/location/direction/action, an object characteristics/spatial-temporal information/size/property/trait/habit/behavior, the venue, a feature/fixture/furniture/barrier/material/machine/living thing/thing/object/boundary/surface/medium that is in/at/of the venue, a map, a constraint of the map, the event/state/situation/condition, a time, a timing, a duration, a current state, a past history, a user, and/or a personal preference, etc.

A stopping criterion of an iterative algorithm may be that change of a current parameter (e.g. offset value) in the updating in an iteration is less than a threshold. The threshold may be 0.5, 1, 1.5, 2, or another number. The threshold may be adaptive. It may change as the iteration progresses. For the offset value, the adaptive threshold may be determined based on the task, particular value of the first time, the current time offset value, the regression window, the regression analysis, the regression function, the regression error, the convexity of the regression function, and/or an iteration number.

The local extremum may be determined as the corresponding extremum of the regression function in the regression window. The local extremum may be determined based on a set of time offset values in the regression window and a set of associated regression function values. Each of the set of associated regression function values associated with the set of time offset values may be within a range from the corresponding extremum of the regression function in the regression window.

The searching for a local extremum may comprise a robust search, a minimization, a maximization, an optimization, a statistical optimization, a dual optimization, a constraint optimization, a convex optimization, a global optimization, a local optimization an energy minimization, a linear regression, a quadratic regression, a higher order regression, a linear programming, a nonlinear programming, a stochastic programming, a combinatorial optimization, a constraint programming, a constraint satisfaction, a calculus of variations, an optimal control, a dynamic programming, a mathematical programming, a multi-objective optimization, a multi-modal optimization, a disjunctive programming, a space mapping, an infinite-dimensional optimization, a heuristics, a metaheuristics, a convex programming, a semidefinite programming, a conic programming, a cone programming, an integer programming, a quadratic programming, a fractional programming, a numerical analysis, a simplex algorithm, an iterative method, a gradient descent, a subgradient method, a coordinate descent, a conjugate gradient method, a Newton's algorithm, a sequential quadratic programming, an interior point method, an ellipsoid method, a reduced gradient method, a quasi-Newton method, a simultaneous perturbation stochastic approximation, an interpolation method, a pattern search method, a line search, a non-differentiable optimization, a genetic algorithm, an evolutionary algorithm, a dynamic relaxation, a hill climbing, a particle swarm optimization, a gravitation search algorithm, a simulated annealing, a memetic algorithm, a differential evolution, a dynamic relaxation, a stochastic tunneling, a Tabu search, a reactive search optimization, a curve fitting, a least square, a simulation based optimization, a variational calculus, and/or a variant. The search for a local extremum may be associated with an objective function, a loss function, a cost function, a utility function, a fitness function, an energy function, and/or an energy function.

Regression may be performed using a regression function to fit sampled data (e.g. CI, a feature of CI, a component of CI) or another function (e.g. autocorrelation function) in a regression window. In at least one iteration, a length of the regression window and/or a location of the regression window may change. The regression function may be a linear function, a quadratic function, a cubic function, a polynomial function, and/or another function.

The regression analysis may minimize an absolute error, a square error, a higher order error (e.g. third order, fourth order, etc.), a robust error (e.g. square error for smaller error magnitude and absolute error for larger error magnitude, or a first kind of error for smaller error magnitude and a second kind of error for larger error magnitude), another error, a weighted sum of absolute error (e.g. for a wireless transmitter with multiple antennas and a wireless receiver with multiple antennas, each pair of transmitter antenna and receiver antenna form a link. Error associated with different links may have different weights. One possibility is that some links and/or some components with larger noise may have smaller or bigger weight.), a weighted sum of square error, a weighted sum of higher order error, a weighted sum of robust error, a weighted sum of the another error, an absolute cost, a square cost, a higher order cost, a robust cost, another cost, a weighted sum of absolute cost, a weighted sum of square cost, a weighted sum of higher order cost, a weighted sum of robust cost, and/or a weighted sum of another cost.

The regression error determined may be an absolute error, a square error, a higher order error, a robust error, yet another error, a weighted sum of absolute error, a weighted sum of square error, a weighted sum of higher order error, a weighted sum of robust error, and/or a weighted sum of the yet another error.

The time offset associated with maximum regression error (or minimum regression error) of the regression function with respect to the particular function in the regression window may become the updated current time offset in the iteration.

A local extremum may be searched based on a quantity comprising a difference of two different errors (e.g. a difference between absolute error and square error). Each of the two different errors may comprise an absolute error, a square error, a higher order error, a robust error, another error, a weighted sum of absolute error, a weighted sum of square error, a weighted sum of higher order error, a weighted sum of robust error, and/or a weighted sum of the another error.

The quantity may be compared with an F-distribution, a central F-distribution, another statistical distribution, a threshold, a threshold associated with a probability, a threshold associated with a probability of finding a false peak, a threshold associated with the F-distribution, a threshold associated the central F-distribution, and/or a threshold associated with the another statistical distribution.

The regression window may be determined based on at least one of: the movement of the object, a quantity associated with the object, the at least one characteristics and/or spatial-temporal information of the object associated with the movement of the object, an estimated location of the local extremum, a noise characteristics, an estimated noise characteristics, an F-distribution, a central F-distribution, another statistical distribution, a threshold, a preset threshold, a threshold associated with a probability, a threshold associated with a desired probability, a threshold associated with a probability of finding a false peak, a threshold associated with the F-distribution, a threshold associated the central F-distribution, a threshold associated with the another statistical distribution, a condition that a quantity at the window center is largest within the regression window, a condition that the quantity at the window center is largest within the regression window, a condition that there is only one of the local extremum of the particular function for the particular value of the first time in the regression window, another regression window, and/or another condition.

The width of the regression window may be determined based on the particular local extremum to be searched. The local extremum may comprise first local maximum, second local maximum, higher order local maximum, first local maximum with positive time offset value, second local maximum with positive time offset value, higher local maximum with positive time offset value, first local maximum with negative time offset value, second local maximum with negative time offset value, higher local maximum with negative time offset value, first local minimum, second local minimum, higher local minimum, first local minimum with positive time offset value, second local minimum with positive time offset value, higher local minimum with positive time offset value, first local minimum with negative time offset value, second local minimum with negative time offset value, higher local minimum with negative time offset value, first local extremum, second local extremum, higher local extremum, first local extremum with positive time offset value, second local extremum with positive time offset value, higher local extremum with positive time offset value, first local extremum with negative time offset value, second local extremum with negative time offset value, and/or higher local extremum with negative time offset value.

A current parameter (e.g. time offset value) may be initialized based on a target value, a target profile, a trend, a past trend, a current trend, a target speed, a speed profile, a target speed profile, a past speed trend, the movement of the object, at least one characteristics and/or spatial-temporal information of the object associated with the movement of object, a positional quantity of the object, an initial speed of the object associated with the movement of the object, a predefined value, an initial width of the regression window, a time duration, a value based on a carrier frequency of the wireless signal, a bandwidth of the wireless signal, an amount of antennas associated with the wireless multipath channel, a noise characteristics, and/or an adaptive value. The current time offset may be at the center, on the left side, on the right side, and/or at another fixed relative location, of the regression window.

FIG. 1 illustrates an exemplary network environment 100 for event detection and monitoring in a venue, according to one embodiment of the present teaching. As shown in FIG. 1, the exemplary network environment 100 includes a transmitter 110, an antenna 112, a wireless channel 130, an antenna 122, and a receiver 120. The antenna 112 is electrically coupled to the transmitter 110; the antenna 122 is electrically coupled to the receiver 120.

In one embodiment, the transmitter 110 is located at a first position in a venue; while the receiver 120 is located at a second position in the venue. The transmitter 110 is configured for transmitting a wireless signal through the wireless channel 130. The wireless channel 130 in this example is a wireless multipath channel that is impacted by a motion of an object in the venue. According to various embodiments, the object may be a human (e.g. a baby 142, or a patient 146) or a pet (e.g. a puppy 144). The receiver 120 in this example receives the wireless signal through the wireless multipath channel 130 and obtains at least one time series of channel information (CI) of the wireless multipath channel based on the wireless signal. Because the motion of the object impacts the wireless multipath channel through which the wireless signal is transmitted, the channel information 125 extracted from the wireless signal includes information related to the object motion.

In various embodiments, the transmitter 110 may be part of a Bot or a Type 1 device placed in a venue, while the receiver 120 may be part of an Origin or a Type 2 device placed in the venue. In various embodiments, the Bot and/or the Origin may include (not shown) multiple transmitters, multiple receivers, and/or multiple transceivers. In one embodiment, the antenna 112 and/or the antenna 122 is replaced with a multi-antenna array that can form a plurality of beams each of which points in a distinct direction. The transmitter 110 can be configured to wirelessly transmit signals having different types or functions. Similarly, the receiver 120 is configured to receive wireless signals having different types or functions. In one embodiment, the transmitter 110 has at least one antenna; and the receiver 120 has at least one antenna. Each of the at least one time series of CI is associated with one of the at least one antenna of the transmitter 110 and one of the at least one antenna of the receiver 120.

Figure 2:
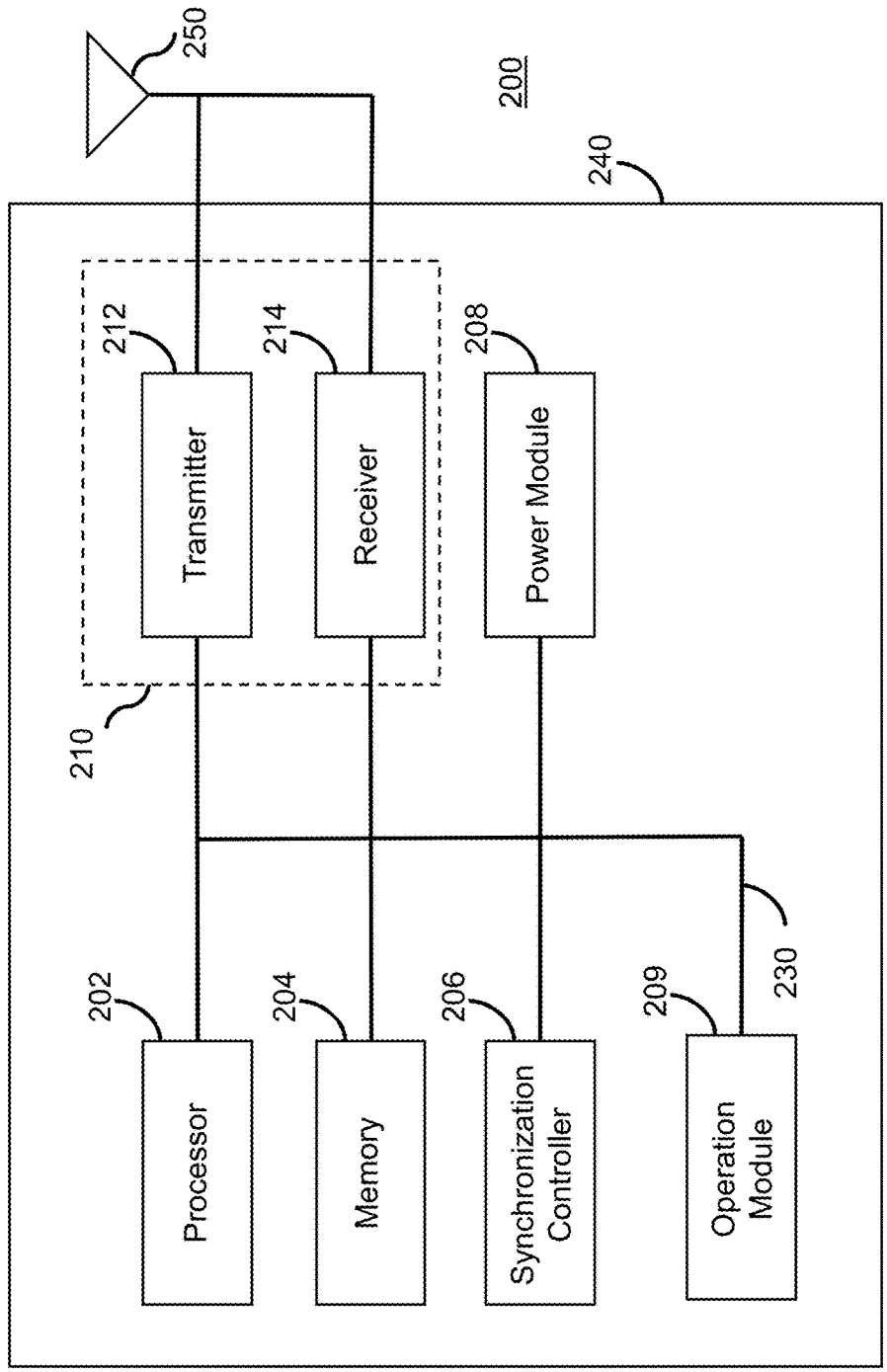
FIG. 2 illustrates an exemplary diagram of a device in a wireless monitoring system, according to one embodiment of the present teaching.

FIG. 2 illustrates an exemplary diagram of a device 200 in a wireless monitoring system, according to one embodiment of the present teaching. The device 200 is an example of a device that can be configured to implement the various methods described herein. According to various embodiments, the device may be: a Type 1 device which is a Bot including a transmitter, a Type 2 device which is an Origin including a receiver, an event recognition engine, and/or other components in FIGS. 1 and 3-18. As shown in FIG. 2, the device 200 includes a housing 240 containing a processor 202, a memory 204, a transceiver 210 comprising a transmitter 212 and a receiver 214, a synchronization controller 206, a power module 208, and an operation module 209.

In this embodiment, the processor 202 controls the general operation of the device 200 and can include one or more processing circuits or modules such as a central processing unit (CPU) and/or any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable circuits, devices and/or structures that can perform calculations or other manipulations of data.

The memory 204, which can include both read-only memory (ROM) and random access memory (RAM), can provide instructions and data to the processor 202. A portion of the memory 204 can also include non-volatile random access memory (NVRAM). The processor 202 typically performs logical and arithmetic operations based on program instructions stored within the memory 204. The instructions (a.k.a., software) stored in the memory 204 can be executed by the processor 202 to perform the methods described herein. The processor 202 and the memory 204 together form a processing system that stores and executes software. As used herein, "software" means any type of instructions, whether referred to as software, firmware, middleware, microcode, etc. which can configure a machine or device to perform one or more desired functions or processes. Instructions can include code (e.g., in source code format, binary code format, executable code format, or any other suitable format of code). The instructions, when executed by the one or more processors, cause the processing system to perform the various functions described herein.

The transceiver 210, which includes the transmitter 212 and receiver 214, allows the device 200 to transmit and receive data to and from a remote device (e.g., an Origin or a Bot). An antenna 250 is typically attached to the housing 240 and electrically coupled to the transceiver 210. In various embodiments, the device 200 includes (not shown) multiple transmitters, multiple receivers, and multiple transceivers. In one embodiment, the antenna 250 is replaced with a multi-antenna array 250 that can form a plurality of beams each of which points in a distinct direction. The transmitter 212 can be configured to wirelessly transmit signals having different types or functions, such signals being generated by the processor 202. Similarly, the receiver 214 is configured to receive wireless signals having different types or functions, and the processor 202 is configured to process signals of a plurality of different types.

In one embodiment, the device 200 may be a Bot or an Origin of a wireless monitoring system. The wireless monitoring system may comprise at least one Bot and at least one Origin. The synchronization controller 206 in this example may be configured to control the operations of the device 200 to be synchronized or un-synchronized with another device, e.g. another Origin or another Bot. In one embodiment, each of the device 200 and other Bots or Origins in the system may transmit or receive the wireless signals individually and asynchronously.

The operation module 209 in this example may perform one or more operations for event detection and monitoring. The operation module 209 may comprise one or more sub-modules to implement different methods disclosed herein. In one embodiment, the device 200 may be an event recognition engine of a wireless monitoring system, where the operation module 209 includes one or more of the components for recognizing and/or classifying an event, e.g. door open, door close, door x % open, or other events related to security.

The power module 208 can include a power source such as one or more batteries, and a power regulator, to provide regulated power to each of the above-described modules in FIG. 2. In some embodiments, if the device 200 is coupled to a dedicated external power source (e.g., a wall electrical outlet), the power module 208 can include a transformer and a power regulator.

The various modules discussed above are coupled together by a bus system 230. The bus system 230 can include a data bus and, for example, a power bus, a control signal bus, and/or a status signal bus in addition to the data bus. It is understood that the modules of the device 200 can be operatively coupled to one another using any suitable techniques and mediums.

Although a number of separate modules or components are illustrated in FIG. 2, persons of ordinary skill in the art will understand that one or more of the modules can be combined or commonly implemented. For example, the processor 202 can implement not only the functionality described above with respect to the processor 202, but also implement the functionality described above with respect to the operation module 209. Conversely, each of the modules illustrated in FIG. 2 can be implemented using a plurality of separate components or elements.

In one embodiment, a method of a system having a processor, a memory communicatively coupled with the processor and a set of instructions stored in the memory for recognizing events in a venue is disclosed. The system comprises a first transmitter, a second transmitter, at least one first receiver, at least one second receiver, and an event recognition engine. Each of the first transmitter, the second transmitter, the at least one first receiver, the at least one second receiver, and the event recognition engine can be implemented as the device 200. The method comprises: for each of at least one known event happening in a venue: transmitting, by an antenna of the first transmitter, a respective training wireless signal to the at least one first receiver through a wireless multipath channel in the venue in a training time period associated with the known event, obtaining, asynchronously by each of the at least one first receiver based on the training wireless signal, at least one time series of training channel information (training CI time series) of the wireless multipath channel between the first receiver and the first transmitter in the training time period associated with the known event, and pre-processing the at least one training CI time series; training, by the event recognition engine, at least one classifier for the at least one known event based on the at least one training CI time series; and for a current event happening in the venue in a current time period, transmitting, by an antenna of the second transmitter, a current wireless signal to the at least one second receiver through the wireless multipath channel impacted by the current event in the venue in the current time period associated with the current event, obtaining, asynchronously by each of the at least one second receiver based on the current wireless signal, at least one time series of current channel information (current CI time series) of the wireless multipath channel between the second receiver and the second transmitter in the current time period associated with the current event, pre-processing the at least one current CI time series, and applying, by the event recognition engine, the at least one classifier to: classify at least one of: the at least one current CI time series, a portion of a particular current CI time series, and a combination of the portion of the particular current CI time series and a portion of an additional CI time series, and associate the current event with at least one of: a known event, an unknown event and another event. A training CI time series associated with a first receiver and a current CI time series associated with a second receiver have at least one of: different starting times, different time durations, different stopping times, different counts of items in their respective time series, different sampling frequencies, different sampling periods between two consecutive items in their respective time series, and channel information (CI) with different features.

The venue may be a house to be guarded. The known events may include: e.g. "front door open", "back door open", "all door close", "bedroom window open", etc. The set of devices (the first transmitter, the at least one first receiver) used during training and the set of devices (the second transmitter, the at least one second receiver) used during operation may be the same or different in various situations. When they are the same, once two devices (a transmitter and a receiver) are plugged in or installed, training can be performed and security operation can begin. In case the devices are moved, another round of training may be performed for security operation. Pre-processing may include denoising and correction of phase error and other errors. The system may perform monitoring and guard operation using a small section of CI time series (e.g. 0.1 second, or 1 second). In case a portion of CI contains part of a training motion (e.g. the door moves from "close" to 30% open, and then does not move), the portion may be combined with a past recording of the door opening from 30% to fully open so that the classification can be applied. If the CI associated with the current event does not match any of the training CI, the current event may be declared as an "unknown event".

In one embodiment, each training CI time series and each current CI time series comprise at least two CI each with an associated time stamp. Each CI is associated with a respective time stamp. According to various embodiments, the first transmitter and the second transmitter may be the same device; the first transmitter and the second transmitter may be at a same location in the venue; the at least one first receiver and the at least one second receiver may be the same; the at least one first receiver may be a permutation of the at least one second receiver; a particular first receiver and a particular second receiver may be the same device; at least one of: the at least one second receiver and a subset of the at least one second receiver, may be a subset of the at least one first receiver; at least one of: the at least one second receiver and a subset of the at least one second receiver, may be a permutation of a subset of the at least one first receiver; at least one of: the at least one first receiver and a subset of the at least one first receiver, may be a subset of the at least one second receiver; at least one of: the at least one first receiver and a subset of the at least one first receiver, may be a permutation of a subset of the at least one second receiver; an antenna of the first transmitter and an antenna of the second transmitter may be at a same location in the venue; at least one of: the at least one second receiver and a subset of the at least one second receiver, may be at a same respective location as a subset of the at least one first receiver; at least one of: the at least one first receiver and a subset of the at least one first receiver, may be at a same respective location as a subset of the at least one second receiver; an antenna of the first transmitter and an antenna of the second transmitter may be at a same location in the venue; at least one of: antennas of the at least one second receiver and antennas of a subset of the at least one second receiver, may be at same respective locations as respective antennas of a subset of the at least one first receiver; at least one of: antennas of the at least one first receiver and antennas of a subset of the at least one first receiver, may be at same respective locations as respective antennas of a subset of the at least one second receiver.

In one embodiment, the pre-processing comprises at least one of: doing nothing, zero-padding, time-domain processing, frequency domain processing, time-frequency processing, spatially varying processing, temporally varying processing, adaptive processing, de-noising, smoothing, conditioning, enhancement, restoration, feature extraction, weighted averaging, averaging over antenna links, averaging over selected frequency, averaging over selected components, quantization, vector quantization, filtering, linear filtering, nonlinear filtering, low-pass filtering, bandpass filtering, high-pass filtering, median filtering, ranked filtering, quartile filtering, percentile filtering, mode filtering, linear filtering, nonlinear filtering, finite impulse response (FIR) filtering, infinite impulse response (IIR) filtering, moving average (MA) filtering, auto-regressive (AR) filtering, auto-regressive moving average (ARMA) filtering, thresholding, soft thresholding, hard thresholding, soft clipping, local maximization, local minimization, optimization of a cost function, neural network, machine learning, supervised learning, unsupervised learning, semi-supervised learning, transformation, mapping, transform, inverse transform, integer transform, power-of-2 transform, real transform, floating-point transform, fixed-point transform, complex transform, fast transform, Fourier transform, Laplace transform, Hadamard transform, Hilbert transform, sine transform, cosine transform, triangular transform, wavelet transform, transformation, decomposition, selective filtering, adaptive filtering, derivative, first order derivative, second order derivative, higher order derivative, integration, zero crossing, indicator function, absolute conversion, convolution, multiplication, division, another transform, another processing, another filter, another function, and another preprocessing. In one embodiment, the pre-processing comprises at least one of: normalization, temporal normalization, frequency normalization, magnitude correction, phase correction, phase cleaning, cleaning a phase associated with the channel information, normalizing components associated with the channel information, cleaning a phase of frequency components of the channel information, normalizing the frequency components, re-sampling, labeling, tagging, training, sorting, grouping, folding, thresholding, matched filtering, spectral analysis, clustering, quantization, vector quantization, time correction, time base correction, time stamp correction, sampling rate up-conversion/down-conversion, interpolation, intrapolation, extrapolation, subsampling, decimation, compression, expansion, encryption decryption, coding, storing, retrieving, transmitting, receiving, representing, merging, combining, splitting, tracking, monitoring, projection, orthogonal projection, non-orthogonal projection, over-complete projection, decomposition, eigen-decomposition, principal component analysis (PCA), sparse approximation, matching pursuit, and another operation etc.

In one embodiment, the method comprises aligning a first section of a first time duration of a first CI time series (e.g. the training CI time series) and a second section of a second time duration of a second CI time series (e.g. the current CI time series), and computing a map between items of the first section and items of the second section.

In one embodiment, the first CI time series may be processed by a first operation. The second CI time series may be processed by a second operation. At least one of: the first operation and the second operation, to comprise at least one of: subsampling, re-sampling, interpolation, filtering, transformation, feature extraction, pre-processing, and another operation.

In one embodiment, the method further comprises mapping a first item of the first section to a second item of the second section. In one embodiment, the method further comprises mapping the first item of the first section also to another item of the second section. In one embodiment, mapping another item of the first section to the second item of the second section.

In one embodiment, at least one constraint is satisfied by at least one function of at least one of: the first item of the first section of the first CI time series, another item of the first CI time series, a time stamp of the first item, a time difference of the first item, a time differential of the first item, a neighboring time stamp of the first item, another time stamp associated with the first item, the second item of the second section of the second CI time series, another item of the second CI time series, a time stamp of the second item, a time difference of the second item, a time differential of the second item, a neighboring time stamp of the second item, and another time stamp associated with the second item. In one embodiment, one of the at least one constraint is that a difference between the time stamp of the first item and the time stamp of the second item is upper-bounded by an adaptive upper threshold and lower-bounded by an adaptive lower threshold.

In one embodiment, the first section is the entire first CI time series, and/or the second section is the entire second CI time series. In one embodiment, the first time duration is not equal to the second time duration. In one embodiment, the method further comprises determining a section of a time duration of a CI time series adaptively.

In one embodiment, the method further comprises determining a starting time and an ending time of a section. In one embodiment, the method further comprises computing a tentative section of the CI time series, and determining the section by removing a beginning portion and an ending portion of the tentative section.

In one embodiment, the method further comprises: determining a beginning portion of a tentative section by: considering items of the tentative section with increasing time stamp as a current item iteratively, one item at a time; computing recursively an activity measure associated with at least one of: the current item associated with a current time stamp, past items of the tentative section with time stamps not larger than the current time stamp, and future items of the tentative section with time stamps not smaller than the current time stamp; adding the current item to the beginning portion of the tentative section if a criterion associated with the activity measure is satisfied.

In one embodiment, the method further comprises: determining an ending portion of a tentative section by: considering items of the tentative section with decreasing time stamp as a current item iteratively, one item at a time; iteratively computing and determining at least one activity measure associated with at least one of: the current item associated with a current time stamp, past items of the tentative section with time stamps not larger than the current time stamp, and future items of the tentative section with time stamps not smaller than the current time stamp; and adding the current item to the ending portion of the tentative section if a criterion associated with the at least one activity measure is satisfied. In one embodiment, the criterion associated with the activity measure comprises at least one of: the activity measure is smaller than an adaptive upper threshold, the activity measure is larger than an adaptive lower threshold, the activity measure is smaller than an adaptive upper threshold consecutively for at least a predetermined amount of consecutive time stamps, the activity measure is larger than an adaptive lower threshold consecutively for at least another predetermined amount of consecutive time stamps, the activity measure is smaller than an adaptive upper threshold consecutively for at least a predetermined percentage of the predetermined amount of consecutive time stamps, the activity measure is larger than an adaptive lower threshold consecutively for at least another predetermined percentage of the another predetermined amount of consecutive time stamps, another activity measure associated with another time stamp associated with the current time stamp is smaller than another adaptive upper threshold and larger than another adaptive lower threshold, at least one activity measure associated with at least one respective time stamp associated with the current time stamp is smaller than respective upper threshold and larger than respective lower threshold, percentage of time stamps with associated activity measure smaller than respective upper threshold and larger than respective lower threshold in a set of time stamps associated with the current time stamp exceeds a threshold, and another criterion. In one embodiment, the activity measure associated with an item at time T1 to comprise at least one of: a first function of the item at time T1 and an item at time T1−D1, wherein D1 is a pre-determined positive quantity, a second function of the item at time T1 and an item at time T1+D1, a third function of the item at time T1 and an item at time T2, wherein T2 is a pre-determined quantity, and a fourth function of the item at time T1 and another item.

In one embodiment, at least one of: the first function, the second function, the third function, and the fourth function, is at least one of: a function F1(x, y, . . . ) with at least two scalar arguments: x and y, a function F2(X, Y, . . . ) with at least two vector arguments: X and Y, and a function F3(X1, Y1, . . . ) with at least two arguments: X1 and Y1. In one embodiment, the function F1 is a function of at least one of the following: x, y, (x−y), (y−x), abs(x−y), x^a1, y^b1, abs(x^a1−y^b1), (x−y)^a1, (x/y), (x+a1)/(y+b1), (x^a1/y^b1), and ((x/y)^a1−b1), wherein a1 and b1 are predetermined quantities; both X and Y are n-tuples such that X=(x_1, x_2, . . . , x_n) and Y=(y_1, y_2, . . . , y_n); the function F2 is a function of at least one of the following: x_i, y_i, (x_i−y_i), (y_i−x_i), abs(x_i−y_i), x_i^a2, y_i^b2, abs (x_i^a2−y_i^b2), (x_i−y_i)^a2, (x_i/y_i), (x_i+a2)/(y_i+b2), (x_i^a2/y_i^b2), and ((x_i/y_i)^a2−b2); i, ranging from 1 to n, is a component index of the n-tuples X and Y; both X1 and Y1 are n-tuples comprising N components such that X1= (x1_1, x1_2, . . . , x1_N) and Y1=(y1_1, y1_2, . . . , y1_N); the function F3 comprises a component-by-component summation of another function of at least one of the following: x1_j, y1_j, (x1_j−y1_j), (y1_j−x1_j), abs(x1_j−y1_j), x1_j^a3, y1_j^b3, abs(x1_j^a3−y1_j^b3), (x1_j−y1_)^a3, (x1_j/y1_j), (x1_j+a3)/(y1_j+b3), (x1_j^a3/y1_j^b3), and ((x1_j/y1_j)^a3−b3); and j, ranging from 1 to N, is a component index of the n-tuples X1 and Y1.

In one embodiment, the method further comprises computing the map using dynamic time warping (DTW). In one embodiment, the dynamic time warping (DTW) comprises a constraint on at least one of: the map, the items of the first CI time series, the items of the second CI time series, the first time duration, the second time duration, the first section, and the second section.

In one embodiment, the method further comprises: aligning a first section of a first time duration of a first CI time series and a second section of a second time duration of a second CI time series, computing a map comprising more than one links between first items of the first section and second items of the second section, each link associating a first item with a first time stamp with a second item with a second time stamp, computing a mismatch cost between the aligned first section and the aligned second section, and applying the at least one classifier based on the mismatch cost. In one embodiment, the mismatch cost comprises a function of: an item-wise cost between a first item of the first section of the first CI time series and a second item of the second section of the second CI time series associated with the first item by a link of the map, and a link-wise cost associated with the link of the map. In one embodiment, the aligned first section and the aligned second section are represented respectively as a first vector and a second vector, both of same vector length; the mismatch cost to comprise at least one of: an inner product, an inner-product-like quantity, a quantity based on correlation, a quantity based on covariance, a discriminating score, a distance, a Euclidean distance, an absolute distance, an L_1 distance, an L_2 distance, an L_k distance, a weighted distance, a distance-like quantity and another similarity value, between the first vector and the second vector; and the mismatch cost is normalized by the vector length. In one embodiment, a parameter derived from the mismatch cost between the first section of the first time duration of the first CI time series and the second section of the second time duration of the second CI time series is modeled with a statistical distribution; and at least one of: a scale parameter, a location parameter and another parameter, of the statistical distribution is estimated. In one embodiment, the first section of the first time duration of the first CI time series is a sliding section of the first CI time series, and the second section of the second time duration of the second CI time series is a sliding section of the second CI time series.

In one embodiment, the method further comprises: applying a first sliding window to the first CI time series and a corresponding second sliding window to the second CI time series, aligning the first sliding window of the first CI time series and the corresponding second sliding window of the second CI time series, computing mismatch cost between the aligned first sliding window of the first CI time series and the corresponding aligned second sliding window of the second CI time series, and associating the current event with at least one of: the known event, the unknown event and the another event, based on the mismatch cost. In one embodiment, the method further comprises: applying the classifier to at least one of: the first section of the first time duration of the first CI time series, and the second section of the second time duration of the second CI time series. In one embodiment, the method further comprises: applying the at least one classifier to more than one first sections of the first CI time series and more than one respective second sections of the second CI time series, obtaining at least one tentative classification results, each tentative classification result being associated with a respective first section and a respective second section, and associating the current event with at least one of: the known event, the unknown event and the another event, based on a largest number of the at least one tentative classification results associated with at least one of: the known event, the unknown event and the another event. In one embodiment, the method further comprises: associating the current event with at least one of: the known event, the unknown event and the another event, based on the mismatch cost. In one embodiment, the method further comprises: associating the current event with at least one of: the known event, the unknown event and the another event, based on the mismatch cost and additional mismatch cost associated with at least one additional section of the first CI time series and at least one additional section of the second CI time series.

In one embodiment, the known events comprise at least one of: a door closed event, a door open event, a window closed event, a window open event, a multi-state event, an on-state event, an off-state event, an intermediate state event, a continuous state event, a discrete state event, a continuous event, a discrete event, a sequential event, a proximity event, a presence event, an absence event, an entrance event, an exit event, a movement event, an approaching event, a receding event, a progressing event, an action event, a factory event, a logistic event, a navigation event, an alignment event, a vehicle event, a parking event, a machine event, a manufacturing event, a robot event, a drone event, a landing event, a take-off event, a launching event, an accident event, a collision event, an impact event, a striking event, a breaking event, a breakthrough event, an explosive event, an office event, a keyboard event, a computer interface event, a home event, a cleaning event, a hygiene event, a pet event, an insect event, a kitchen event, a cooking event, a meal event, a laundry event, a furniture movement event, a bathroom event, a bedroom event, a living room event, a family room event, a dining room event, a garage event, a foyer event, a staircase event, a basement event, an attic event, a pantry event, a fire event, a water event, a shower event, an air-flow event, a fan event, a heat-related event, a light-related event, a wind event, a sit-down event, a stand-up event, a lie-down event, a get-up event, a rolling event, a turning event, a repeated event, an exercise event, a relaxation event, a resting event, a sleeping event, a fall-down event, a staircase event, a party event, a running event, a walking event, a reading event, a musical event, a sound event, an instrument event, a human motion event, a baby event, a child event, an older adult event, a gesture event, a handwriting event, a drawing event, a home event, an office event, a pet event, a sleeping event, a human-present event, a human-absent event, a sign-of-life-present event, and a sign-of-life-absent event.

In one embodiment, instead of using the whole CSI (which has many components), the system can train (e.g. by using some training algorithm on some training data) a data reduction scheme (a projection). For example, one may find a projection to reduce a 256-dimension CSI to a 10-dimension feature space. One training method is principal component analysis (PCA). In one embodiment, the method further comprises: training a projection for each CI using a dimension reduction method based on the training CI time series associated with the at least one known event, wherein the dimension reduction method to comprise at least one of: principal component analysis (PCA), PCA with different kernel, independent component analysis (ICA), Fisher linear discriminant, vector quantization, supervised learning, unsupervised learning, self-organizing maps, auto-encoder, neural network, deep neural network, and another method, applying the projection to all CI, training the at least one classifier of the at least one event based on the projection and the training CI time series associated with the at least one event, and classifying the at least one current CI time series based on the projection and the at least one current CI time series.

Sometimes the environment is changed over time (e.g. some furniture such as sofa or table is moved) such that the previously trained classifier is no longer appropriate or valid. Thus retraining is performed. In other words, the classifier is re-trained, adapted, updated, or refreshed. In one embodiment, the method further comprises: re-training the projection using at least one of: the dimension reduction method, and another dimension reduction method, based on at least one of: the projection before the re-training, the training CI time series, at least one current CI time series obtained as of the re-training of the projection, and additional training CI time series, wherein the another dimension reduction method to comprise at least one of: a simplified dimension reduction method, principal component analysis (PCA), PCA with different kernels, independent component analysis (ICA), Fisher linear discriminant, vector quantization, supervised learning, unsupervised learning, self-organizing maps, auto-encoder, neural network, deep neural network, and yet another method; re-training the at least one classifier of the at least one event based on at least one of: the re-trained projection, the training CI time series associated with the at least one events, and at least one current CI time series; and classifying the at least one current CI time series based on the re-trained projection, the re-trained classifier, and the current CI time series.

The CSI may be preprocessed before projection. For example, one may retain only the magnitude of each CSI component as the phase tends to be sensitive to noise. If the CSI has 128 components, the preprocessing would give 128 new components each being magnitude of correspond component of the CSI. In one embodiment, each CI to comprise a vector of complex values; each complex value is preprocessed to give the magnitude of the complex value; each CI is preprocessed to give a vector of non-negative real numbers comprising the magnitude of corresponding complex values.

During training, some training CI time series may be weighted more. For example, an important training CI time series may be used more than once in the training, or may have a larger weight in the training cost. In one embodiment, each training CI time series is weighted in the training of the projection. The projection may have N (more than 1) components, e.g. N=5, or 10, or 15, or 20, etc. In one embodiment, the projection comprises more than one projected components. The projection may have at least one most significant component. For example, we may use PCA and retain the N components with highest energy. In one embodiment, the projection comprises at least one projected component that is beneficial for the at least one classifier.

In one embodiment, the current section may be 2 seconds long, with 2M current CSI each with corresponding time stamp. A trained representative section of "front door open" may be 3 seconds long, with 3M training CSI (i.e. duration is different). In DTW, one can establish correspondence between time stamps of the 2M current CSI and time stamps of the 3M training CSI. Then one can compute a mismatch cost between the two sections. Each mismatch cost is a "distance" between a current CSI and a training CSI. To compute the distance, one can compute a CSI-distance between a current CSI and a training CSI, and one can compute the CSI-distance 3M times. The distance may be normalized by the amount of aligned CSI (3M, which is the largest of the two section length) so that distance associated with different events can be compared. In one embodiment, the method further comprises: for at least one first section of a first time duration of the current CI time series: for each of the at least one known event: determining a respective second section of a respective second time duration of a respective representative training CI time series of the respective event, aligning the first section and the respective second section, and computing a mismatch cost between the aligned first section and the aligned respective second section; applying the at least one classifier; and obtaining a tentative classification result based on the mismatch costs; and associating the at least one section with at least one of: one of the at least one known event, an unknown event and the another event based on the at least one tentative classification result.

In one embodiment, a particular classifier associates a first section of the first time duration of the current CI time series to a known event whose respective second section has smallest mismatch cost with the first section. The classifier may choose the event that gives that smallest (normalized) mismatch cost. In one embodiment, the method further comprises: computing how many times each known event achieves the smallest mismatch cost; and associating the at least one section with at least one of: a known event that achieves the smallest mismatch cost for the most times, a known event that achieves smallest overall mismatch cost, wherein overall mismatch cost is a weighted average of at least one mismatch cost associated with the at least one first sections, a known event that achieves smallest of another overall cost, and an unknown event. The associated event is the unknown event in at least one of the following situations: none of the events achieve mismatch cost lower than a first threshold T1 in a sufficient percentage of the at least one first section; and none of the events achieve an overall mismatch cost lower than a second threshold T2.

In one embodiment, the trained representative CI time series is trained based on a large number of training CI time series of the event collected during training phase/stage (e.g. the event may be front-door-open). Distance (mismatch cost) between CI time series may be defined as follows: DTW is applied to a pair (any pair) of training CI time series (or an "activity" or "significant" section of it) so that normalized mismatch cost can be computed. The trained representative may be obtained by clustering, discriminative training, or some kind of machine learning. Important training CI time series may be weighted more than others. In one embodiment, the trained representative CI time series associated with the known event is obtained based on the at least one training CI time series associated with the known event. In one embodiment, the trained representative CI time series associated with the known event is one of the at least one training CI time series associated with the known event.

In one embodiment, the aggregate mismatch associated with a training data point (a training CI time series) among a set of training data points (e.g. a set of training CI time series for "front door open") is a measure of how good it is to represent a set of training data points. The aggregate mismatch can be an average (or weighted average, or other function of) distance between the training data point and each of the other training data point in the set. A good representative data point is close to the other data points. Training representative CI time series is one of the training CI time series. In one embodiment, the trained representative CI time series associated with the known event is a particular one of the at least one training CI time series associated with the known event such that it has smallest aggregate mismatch among the at least one training CI time series; the aggregate mismatch of a particular training CI time series is a function of at least one mismatch cost between the particular training CI time series and each of the rest of the at least one training CI time series aligned with the particular training CI time series; and the function to comprise at least one of: average, weighed average, mean, trimmed mean, median, mode, arithmetic mean, geometric mean, harmonic mean, truncated mean, generalized mean, power mean, f-mean, interquartile mean, and another mean.

In one embodiment, training representative CI time series is not one of the training CI time series. It is computed by minimizing aggregate mismatch. Its duration (length) needs to be determined. In one embodiment, a particular trained representative CI time series associated with a particular known event has a particular time duration; the particular trained representative CI time series of the particular time duration is aligned with each of the at least one training CI time series associated with the known event and respective mismatch cost is computed; the particular trained representative CI time series to minimize an aggregate mismatch with respect to the at least one training CI time series; the aggregate mismatch of a CI time series is a function of at least one mismatch cost between the CI time series and each of at least one training CI time series aligned with the CI time series; and the function to comprise at least one of: average, weighed average, mean, trimmed mean, median, mode, arithmetic mean, geometric mean, harmonic mean, truncated mean, generalized mean, power mean, f-mean, interquartile mean, and another mean.

In one embodiment, even the duration/length of the representative CI time series (section) is obtained by training. Different duration can be checked (trial computed). Different duration of the section can be examined. In one embodiment, the particular time duration minimizes the aggregate mismatch among more than one candidate time durations of the particular trained representative CI time series. In one embodiment, for each of at least one candidate time duration, the optimal trained representative CI time series with the candidate time duration is computed; the particular time duration is chosen as the candidate time duration that gives minimal normalized aggregate mismatch; and the normalized aggregated mismatch associated with a candidate time duration is the respective aggregate mismatch normalized by the candidate time duration.

In another embodiment, the particular time duration is obtained by performing a search among the at least one candidate time durations with the cost function being at least one of: normalized aggregate mismatch, hybrid normalized aggregate mismatch, combination normalized aggregate match, a simplified mismatch, and another cost function; the normalized aggregated mismatch associated with a candidate time duration is the respective aggregate mismatch normalized by the candidate time duration; and the search to comprise at least one of: brute force exhaustive search, gradient descent, steepest descent, stochastic search, genetic search, predictive search, local search, multi-resolution search, hierarchical search, constrained search, unconstrained search, fast search, simplified search, and another search. In one embodiment, the particular time duration and the particular trained representative CI time series with the particular time duration are computed iteratively; a current time duration is initialized as one of the candidate time durations; for the current time duration, a current optimal trained representative CI time series with the current time duration is computed; and for the current optimal trained representative CI time series with the current time duration, the current time duration is changed to give smaller normalized aggregate mismatch.

The initial duration/length of current section of the current CI time series (section) may be equal to a "typical" duration of the event (e.g. "front-door-open"). In one embodiment, the current time duration is initialized with a value based on durations associated with the at least one training CI time series associated with the known event. The initial duration/length of current section of the current CI time series (section) may be computed based on duration of training CI time series of the event (e.g. "front-door-open"). In one embodiment, the current time duration is initialized with a value based on durations associated with the at least one training CI time series associated with the known event.

In one embodiment, each pair of transmitting antenna and receiving antenna corresponds to a current CI time series. For example, each current CI time series is associated with an antenna of the second transmitter and an antenna of a second Type 2 heterogeneous wireless device.

Figure 3:
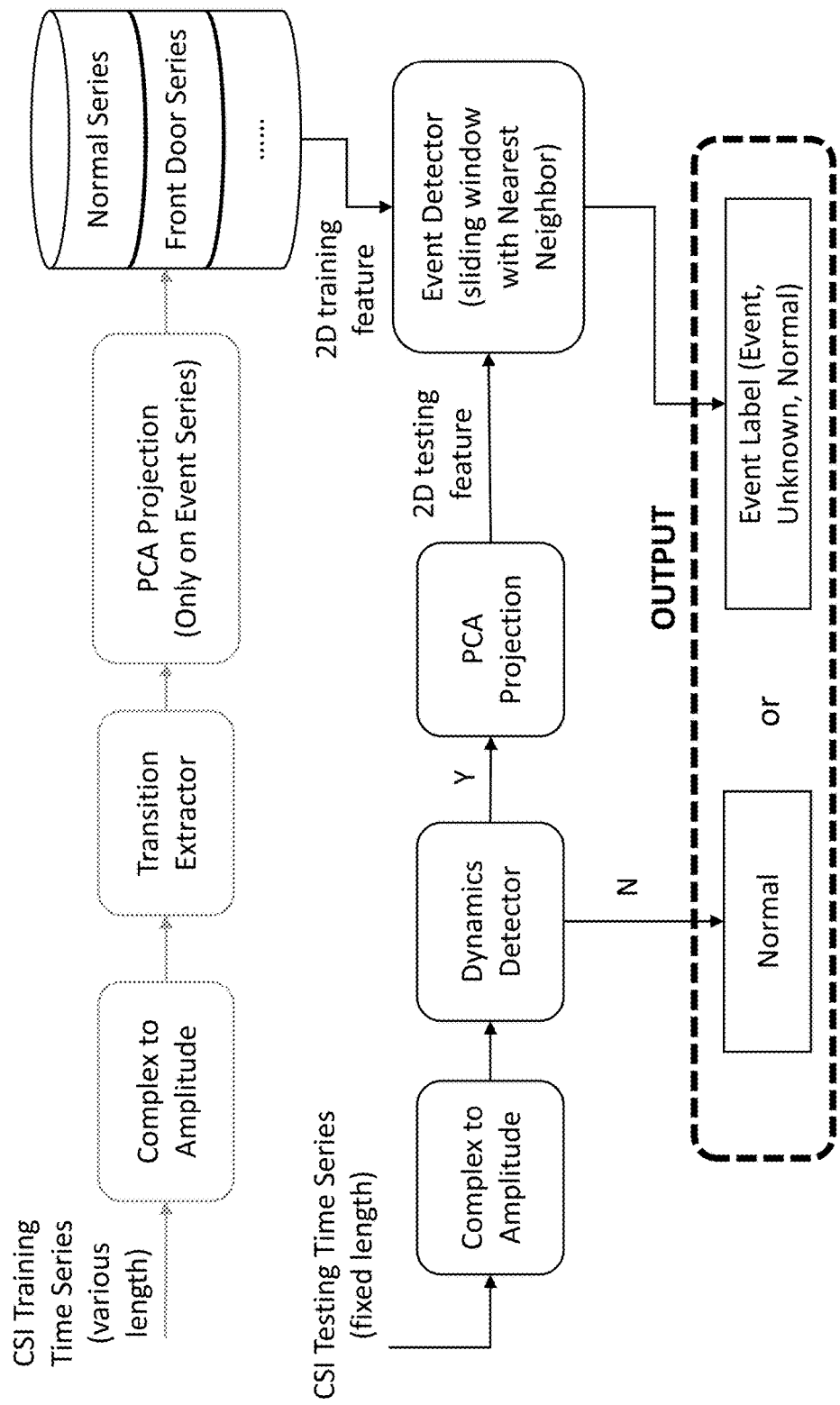
FIG. 3 illustrates an exemplary flow of detecting indoor events using time-reversal technology, according to one embodiment of the present teaching.

FIG. 3 illustrates an exemplary flow of detecting indoor events using time-reversal technology, according to one embodiment of the present teaching. In one embodiment, the present teaching discloses methods, apparatus, devices, and software of a wireless monitoring system comprising training at least one classifier of at least one known events in a venue based on training CI time series associated with the at least one events. For each of the at least one known event happening in the venue in a respective training time period associated with the known event, a respective series of training probe signals is transmitted by an antenna of a first wireless device using a processor, a memory and a set of instructions of the first wireless device to at least one heterogeneous first target wireless receiver through a wireless multipath channel in the venue in the respective training time period. At least one respective time series of training channel information (training CI time series) is obtained asynchronously by each of the at least one heterogeneous first target wireless receiver from the (respective) series of training probe signals. The channel information (CI) is CI of the wireless multipath channel between the heterogeneous first target wireless receiver and the first wireless device in the training time period associated with the known event. The at least one training CI time series is preprocessed. For a current event happening in the venue in a current time period, a series of current probe signals is transmitted by an antenna of a second wireless device using a processor, a memory and a set of instructions of the second wireless device to at least one heterogeneous second target wireless receiver through the wireless multipath channel impacted by the current event in the venue in the current time period associated with the current event. At least one time series of current channel information (current CI time series) is obtained asynchronously by each of the at least one heterogeneous second target wireless receiver from the series of current probe signals. The channel information (CI) is CI of the wireless multipath channel between the heterogeneous second target wireless receiver and the second wireless device in the current time period associated with the current event. The at least one current CI time series is preprocessed.

The at least one classifier is applied to classify at least one current CI time series obtained from the series of current probe signals by the at least one heterogeneous second target wireless receiver, to classify at least one portion of a particular current CI time series, and/or to classify a combination of the at least one portion of the particular current CI time series and another portion of another CI time series. The at least one classifier is also applied to associate the current event with a known event, an unknown event and/or another event. Each series of probe signals may comprise at least two CI each with an associated time stamp. Each CI may be associated with a respective time stamp. A current CI time series associated with a heterogeneous second target wireless receiver and another current CI time series associated with another heterogeneous second target wireless receiver may have different starting time, different time duration, different stopping time, different count of items in the time series, different sampling frequency, different sampling period between two consecutive items in the time series, and/or channel information (CI) with different features.

The first wireless device and the second wireless device may be the same device. The first wireless device and the second wireless device may be at same location in the venue. The at least one heterogeneous first target wireless receiver and the at least one heterogeneous second target wireless receiver may be the same. The at least one heterogeneous first target wireless receiver may be a permutation of the at least one heterogeneous second target wireless receiver. A particular heterogeneous first target wireless receiver and a particular heterogeneous second target wireless receiver may be the same device. The at least one heterogeneous first target wireless receiver and/or a subset of the at least one heterogeneous first target wireless receiver may be a subset of the at least one heterogeneous second target wireless receiver. The at least one heterogeneous second target wireless receiver and/or a subset of the at least one heterogeneous second target wireless receiver may be a subset of the at least one heterogeneous first target wireless receiver.

The at least one heterogeneous first target wireless receiver and/or a subset of the at least one heterogeneous first target wireless receiver may be a permutation of a subset of the at least one heterogeneous second target wireless receiver. The at least one heterogeneous second target wireless receiver and/or a subset of the at least one heterogeneous second target wireless receiver may be a permutation of a subset of the at least one heterogeneous first target wireless receiver. The at least one heterogeneous second target wireless receiver and/or a subset of the at least one heterogeneous second target wireless receiver may be at same respective location as a subset of the at least one heterogeneous first target wireless receiver. The at least one heterogeneous first target wireless receiver and/or a subset of the at least one heterogeneous first target wireless receiver may be at same respective location as a subset of the at least one heterogeneous second target wireless receiver.

The antenna of the first wireless device and the antenna of the second wireless device may be at same location in the venue. Antenna(s) of the at least one heterogeneous second target wireless receiver and/or antenna(s) of a subset of the at least one heterogeneous second target wireless receiver may be at same respective location as respective antenna(s) of a subset of the at least one heterogeneous first target wireless receiver. Antenna(s) of the at least one heterogeneous first target wireless receiver and/or antenna(s) of a subset of the at least one heterogeneous first target wireless receiver may be at same respective location(s) as respective antenna(s) of a subset of the at least one heterogeneous second target wireless receiver.

The pre-processing may comprise at least one of: doing nothing, zero-padding, time-domain processing, frequency domain processing, time-frequency processing, spatially varying processing, temporally varying processing, adaptive processing, de-noising, smoothing, conditioning, enhancement, restoration, feature extraction, weighted averaging, averaging over antenna links, averaging over selected frequency, averaging over selected components, quantization, vector quantization, filtering, linear filtering, nonlinear filtering, low-pass filtering, bandpass filtering, high-pass filtering, median filtering, ranked filtering, quartile filtering, percentile filtering, mode filtering, linear filtering, nonlinear filtering, finite impulse response (FIR) filtering, infinite impulse response (IIR) filtering, moving average (MA) filtering, auto-regressive (AR) filtering, auto-regressive moving average (ARMA) filtering, thresholding, soft thresholding, hard thresholding, soft clipping, local maximization, local minimization, optimization of a cost function, neural network, machine learning, supervised learning, unsupervised learning, semi-supervised learning, transformation, mapping, transform, inverse transform, integer transform, power-of-2 transform, real transform, floating-point transform, fixed-point transform, complex transform, fast transform, Fourier transform, Laplace transform, Hadamard transform, Hilbert transform, sine transform, cosine transform, triangular transform, wavelet transform, transformation, decomposition, selective filtering, adaptive filtering, derivative, first order derivative, second order derivative, higher order derivative, integration, zero crossing, indicator function, absolute conversion, convolution, multiplication, division, another transform, another processing, another filter, another function, and/or another preprocessing. The pre-processing may also comprise at least one of: normalization, temporal normalization, frequency normalization, magnitude correction, phase correction, phase cleaning, cleaning a phase associated with the channel information, normalizing components associated with the channel information, cleaning a phase of frequency components of the channel information, normalizing the frequency components, re-sampling, labeling, tagging, training, sorting, grouping, folding, thresholding, matched filtering, spectral analysis, clustering, quantization, vector quantization, time correction, time base correction, time stamp correction, sampling rate up-conversion/down-conversion, interpolation, intrapolation, extrapolation, subsampling, decimation, compression, expansion, encryption decryption, coding, storing, retrieving, transmitting, receiving, representing, merging, combining, splitting, tracking, monitoring, projection, orthogonal projection, non-orthogonal projection, overcomplete projection, decomposition, eigen-decomposition, principal component analysis (PCA), sparse approximation, matching pursuit, and/or another operation, etc.

A first section of a first time duration of the first CI time series and a second section of a second time duration of the second section of the second CI time series may be aligned. A map between items of the first section and items of the second section may be computed. The first CI time series may be processed by a first operation. The second CI time series may be processed by a second operation. The first operation and/or the second operation may comprise at least one of: subsampling, re-sampling, interpolation, filtering, transformation, feature extraction, pre-processing, and/or another operation.

A first item of the first section may be mapped to a second item of the second section. The first item of the first section may also be mapped to another item of the second section. Another item of the first section may also be mapped to the second item of the second section. At least one function of at least one of: the first item of the first section of the first CI time series, another item of the first CI time series, a time stamp of the first item, a time difference of the first item, a time differential of the first item, a neighboring time stamp of the first item, another time stamp associated with the first item, the second item of the second section of the second CI time series, another item of the second CI time series, a time stamp of the second item, a time difference of the second item, a time differential of the second item, a neighboring time stamp of the second item, and another time stamp associated with the second item, may satisfy at least one constraint. One constraint may be that a difference between the time stamp of the first item and the time stamp of the second item may be upper-bounded by an adaptive upper threshold and lower-bounded by an adaptive lower threshold. The first section may be the entire first CI time series. The second section may be the entire second CI time series. The first time duration may be equal to the second time duration.

A section of a time duration of a CI time series may be determined adaptively. A tentative section of the CI time series may be computed. A starting time and an ending time of a section (e.g. the tentative section, the section) may be determined. The section may be determined by removing a beginning portion and an ending portion of the tentative section. A beginning portion of a tentative section may be determined as follows. Iteratively, items of the tentative section with increasing time stamp may be considered as a current item, one item at a time. In each iteration, at least one activity measure may be computed and/or considered. The at least one activity measure may be associated with at least one of: the current item associated with a current time stamp, past items of the tentative section with time stamps not larger than the current time stamp, and/or future items of the tentative section with time stamps not smaller than the current time stamp. The current item may be added to the beginning portion of the tentative section if at least one criterion associated with the at least one activity measure is satisfied. The at least one criterion associated with the activity measure may comprise at least one of: (a) the activity measure is smaller than an adaptive upper threshold, (b) the activity measure is larger than an adaptive lower threshold, (c) the activity measure is smaller than an adaptive upper threshold consecutively for at least a predetermined amount of consecutive time stamps, (d) the activity measure is larger than an adaptive lower threshold consecutively for at least another predetermined amount of consecutive time stamps, (e) the activity measure is smaller than an adaptive upper threshold consecutively for at least a predetermined percentage of the predetermined amount of consecutive time stamps, (f) the activity measure is larger than an adaptive lower threshold consecutively for at least another predetermined percentage of the another predetermined amount of consecutive time stamps, (g) another activity measure associated with another time stamp associated with the current time stamp is smaller than another adaptive upper threshold and larger than another adaptive lower threshold, (h) at least one activity measure associated with at least one respective time stamp associated with the current time stamp is smaller than respective upper threshold and larger than respective lower threshold, (i) percentage of time stamps with associated activity measure smaller than respective upper threshold and larger than respective lower threshold in a set of time stamps associated with the current time stamp exceeds a threshold, and (j) another criterion.

An activity measure associated with an item at time $T1$ may comprise at least one of: (1) a first function of the item at time $T1$ and an item at time $T1-D1$, wherein $D1$ is a pre-determined positive quantity (e.g. a constant time offset), (2) a second function of the item at time $T1$ and an item at time $T1+D1$, (3) a third function of the item at time $T1$ and an item at time $T2$, wherein $T2$ is a pre-determined quantity (e.g. a fixed initial reference time; $T2$ may be changed over time; $T2$ may be updated periodically; $T2$ may be the beginning of a time period and $T1$ may be a sliding time in the time period), and (4) a fourth function of the item at time $T1$ and another item.

At least one of: the first function, the second function, the third function, and/or the fourth function may be a function (e.g. $F(X, Y, \ldots)$) with at least two arguments: $X$ and $Y$. The function (e.g. F) may be a function of at least one of: $X$, $Y$, $(X-Y)$, $(Y-X)$, $abs(X-Y)$, $X^a$, $Y^b$, $abs(X^a-Y^b)$, $(X-Y)^a$, $(X/Y)$, $(X+a)/(Y+b)$, $(X^a/Y^b)$, and $((X/Y)^a-b)$, wherein a and b may be some predetermined quantities. For example, the function may simply be $abs(X-Y)$, or $(X-Y)^2$, $(X-Y)^4$. The function may be a robust function. For example, the function may be $(X-Y)^2$ when $abs(X-Y)$ is less than a threshold $T$, and $(X-Y)+a$ when $abs(X-Y)$ is larger than $T$. Alternatively, the function may be a constant when $abs(X-Y)$ is larger than $T$. The function may also be bounded by a slowly increasing function when $abs(X-y)$ is larger than $T$, so that outliers cannot severely affect the result. Another example of the function may be $(abs(X/Y)-a)$, where $a=1$. In this way, if $X=Y$ (i.e. no change or no activity), the function will give a value of 0. If X is larger than Y, $(X/Y)$ will be larger than 1 (assuming X and Y are positive) and the function will be positive. And if X is less than Y, $(X/Y)$ will be smaller than 1 and the function will be negative. In another example, both X and Y may be n-tuples such that $X=(x\_1, x\_2, \ldots, x\_n)$ and $Y=(y\_1, y\_2, \ldots, y\_n)$. The function may be a function of at least one of: $x\_i$, $y\_i$, $(x\_i-y\_i)$, $(y\_i-x\_i)$, $abs(x\_i-y\_i)$, $x\_i^a$, $y\_i^b$, $abs(x\_i^a-y\_i^b)$, $(x\_i-y\_i)^a$, $(x\_i/y\_i)$, $(x\_i+a)/(y\_i+b)$, $(x\_i^a/y\_i^b)$, and $((x\_i/y\_i)^a-b)$, wherein i is a component index of the n-tuple X and Y, and $1<=i<=n$. E.g. component index of $x\_1$ is $i=1$, component index of $x\_2$ is $i=2$. The function may comprise a component-by-component summation of another function of at least one of the following: $x\_i$, $y\_i$ $(x\_i-y\_i)$, $(y\_i-x\_i)$, $abs(x\_i-y\_i)$, $x\_i^a$, $y\_i^b$, $abs(x\_i^a-y\_i^b)$, $(x\_i-y\_i)^a$, $(x\_i/y\_i)$, $(x\_i+a)/(y\_i+b)$, $(x\_i^a/y\_i^b)$, and $((x\_i/y\_i)^a-b)$, wherein i is the component index of the n-tuple X and Y. For example, the function may be in a form of $sum\_\{i=1\}^n (abs(x\_i/y\_i)-1)/n$, or $sum\_\{i=1\}^n w\_i*(abs(x^i/y^i)-1)$, where $w\_i$ is some weight for component i.

The map may be computed using dynamic time warping (DTW). The DTW may comprise a constraint on at least one of: the map, the items of the first CI time series, the items of the second CI time series, the first time duration, the second time duration, the first section, and/or the second section. Suppose in the map, the $i^{th}$ domain item is mapped to the $j^{th}$ range item. The constraint may be on admissible combination of i and j (constraint on relationship between i and j). Pairwise mismatch between a first section of a first time duration of a first CI time series and a second section of a second time duration of a second CI time series may be computed. The first section and the second section may be aligned such that a map comprising more than one links may be established between first items of the first CI time series and second items of the second CI time series. With each link, one of the first items with a first time stamp may be associated with one of the second items with a second time stamp.

A mismatch cost between the aligned first section and the aligned second section may be computed. The mismatch cost may comprise a function of: an item-wise mismatch cost between a first item and a second item associated by a particular link of the map, and a link-wise cost associated with the particular link of the map. The aligned first section and the aligned second section may be represented respectively as a first vector and a second vector of same vector length. The mismatch cost may comprise at least one of: an inner product, an inner-product-like quantity, a quantity based on correlation, a quantity based on covariance, a discriminating score, a distance, a Euclidean distance, an absolute distance, an Lk distance (e.g. L1, L2, . . . ), a weighted distance, a distance-like quantity and/or another similarity value, between the first vector and the second vector. The mismatch cost may be normalized by the respective vector length. A parameter derived from the pairwise mismatch between the first section of the first time duration of the first CI time series and the second section of the second time duration of the second CI time series may be modeled with a statistical distribution. At least one of: a scale parameter, a location parameter and/or another parameter, of the statistical distribution may be estimated.

The first section of the first time duration of the first CI time series may be a sliding section of the first CI time series. The second section of the second time duration of the second CI time series may be a sliding section of the second CI time series. A first sliding window may be applied to the first CI time series and a corresponding second sliding window may be applied to the second CI time series. The first sliding window of the first CI time series and the corresponding second sliding window of the second CI time series may be aligned.

Pairwise mismatch between the aligned first sliding window of the first CI time series and the corresponding aligned second sliding window of the second CI time series may be computed. The current event may be associated with at least one of: the known event, the unknown event and/or the another event, based on the pairwise mismatch. The classifier may be applied to at least one of: the first section of the first time duration of the first CI time series, and/or the second section of the second time duration of the second CI time series.

The current event may be associated with at least one of: the known event, the unknown event and/or the another event, based on a largest number of tentative classification results in more than one sections of the first CI time series and corresponding more than sections of the second CI time series. For example, the current event may be associated with a particular known event if the pairwise mismatch points to the particular known event for N consecutive times (e.g. N=10). In another example, the current event may be associated with a particular known event if the percentage of pairwise mismatch within the immediate past N consecutive N pointing to the particular known event exceeds a certain threshold (e.g. >80%).

The current event may be associated with at least one of: the known event, the unknown event and/or the another event, based on the mismatch cost. The current event may be associated with at least one of: the known event, the unknown event and/or the another event, based on the mismatch cost and additional mismatch cost associated with at least one additional section of the first CI time series and at least one additional section of the second CI time series.

The known events may comprise at least one of: a door closed event, a door open event, a window closed event, a window open event, a multi-state event, an on-state event, an off-state event, an intermediate state event, a continuous state event, a discrete state event, a human-present event, a human-absent event, a sign-of-life-present event, and/or a sign-of-life-absent event.

A projection for each channel information may be trained using a dimension reduction method based on the training CI time series. The dimension reduction method may comprise at least one of: principal component analysis (PCA), PCA with different kernel, independent component analysis (ICA), Fisher linear discriminant, vector quantization, supervised learning, unsupervised learning, self-organizing maps, auto-encoder, neural network, deep neural network, and/or another method. The projection may be applied to at least one of: the training CI time series associated with the at least one event, and/or the current CI time series, for the at least one classifier.

The at least one classifier of the at least one event may be trained based on the projection and the training CI time series associated with the at least one event. The at least one current CI time series may be classified based on the projection and the current CI time series. The projection may be re-trained using at least one of: the dimension reduction method, and another dimension reduction method, based on at least one of: the projection before the re-training, the training CI time series, at least one current CI time series before retraining the projection, and/or additional training CI time series.

The another dimension reduction method may comprise at least one of: a simplified dimension reduction method, principal component analysis (PCA), PCA with different kernels, independent component analysis (ICA), Fisher linear discriminant, vector quantization, supervised learning, unsupervised learning, self-organizing maps, auto-encoder, neural network, deep neural network, and/or yet another method.

The at least one classifier of the at least one event may be re-trained based on at least one of: the re-trained projection, the training CI time series associated with the at least one events, and/or at least one current CI time series. The at least one current CI time series may be classified based on: the re-trained projection, the re-trained classifier, and/or the current CI time series. Each CI may comprise a vector of complex values. Each complex value may be preprocessed to give the magnitude of the complex value. Each CI may be preprocessed to give a vector of non-negative real numbers comprising the magnitude of corresponding complex values. Each training CI time series may be weighted in the training of the projection. The projection may comprise more than one projected components. The projection may comprise at least one most significant projected component. The projection may comprise at least one projected component that may be beneficial for the at least one classifier.

A particular classifier may be configured to compute, for a first section of a first time duration of the current CI time series and for each of the at least one known event, pairwise mismatch between the first section of the first time duration of the current CI time series and a second section of a second time duration of a trained representative CI time series associated with the known event. The particular classifier may associate the first section of the first time duration of the current CI time series to a known event whose second section has smallest pairwise mismatch with the first section. The particular classifier may associate the first section of the first time duration of the current CI time series to a known event whose second section has smallest pairwise mismatch with the first section, if a previous first section of another first time duration of the current CI time series has smallest pairwise mismatch with another second section of another second time duration of the trained CI time series associated with the known event.

The trained representative CI time series associated with the known event may be obtained based on the at least one training CI time series associated with the known event. The trained representative CI time series associated with the known event may be one of the at least one training CI time series associated with the known event. The trained representative CI time series associated with the known event may be a particular one of the at least one training CI time series associated with the known event such that it has smallest aggregate mismatch compared with the at least one training CI time series.

The aggregate mismatch may be a function of at least one pairwise mismatch between the particular one and each of the rest of the at least one training CI time series. The function may comprise at least one of: average, weighed average, mean, trimmed mean, median, mode, arithmetic mean, geometric mean, harmonic mean, truncated mean, generalized mean, power mean, f-mean, interquartile mean, and/or another mean.

A particular trained representative CI time series associated with a particular known event may have a particular time duration. The particular trained representative CI time series of the particular time duration may be aligned with each of the at least one training CI time series associated with the known event. Respective pairwise mismatch may be computed. The particular trained representative CI time series may minimize an aggregate mismatch with respect to the at least one training CI time series. The aggregate mismatch of a CI time series may be a function of at least one pairwise mismatch between the CI time series and each of the at least one training CI time series aligned with the CI time series. The particular time duration may minimize the aggregate mismatch among more than one candidate time durations of the particular trained representative CI time series. The function may comprise at least one of: average, weighed average, mean, trimmed mean, median, mode, arithmetic mean, geometric mean, harmonic mean, truncated mean, generalized mean, power mean, f-mean, interquartile mean, and/or another mean.

At least one of: the aggregate mismatch and/or each pairwise mismatch, may be normalized, so that the aggregate mismatch of each of the at least one training CI time series can be compared in search of the one with minimum aggregate mismatch. The particular time duration may minimize the aggregate mismatch among more than one candidate time durations of the particular trained representative CI time series.

For each of at least one candidate time duration, the optimal trained representative CI time series with the candidate time duration may be computed. The particular time duration may be chosen as the candidate time duration that gives minimal normalized aggregate mismatch. The normalized aggregated mismatch associated with a candidate time duration may be the respective aggregate mismatch normalized by the candidate time duration.

The particular time duration may be obtained by performing a search among the at least one candidate time durations with the cost function being at least one of: normalized aggregate mismatch, hybrid normalized aggregate mismatch, combination normalized aggregate match, a simplified mismatch, and/or another cost function. The normalized aggregated mismatch associated with a candidate time duration may be the respective aggregate mismatch normalized by the candidate time duration. The search may comprise at least one of: brute force exhaustive search, gradient descent, steepest descent, stochastic search, genetic search, predictive search, local search, multi-resolution search, hierarchical search, constrained search, unconstrained search, fast search, simplified search, and/or another search.

The particular time duration and the particular trained representative CI time series with the particular time duration may be computed iteratively. A current time duration may be initialized as one of the candidate time durations. For the current time duration, a current optimal trained representative CI time series with the current time duration may be computed. For the current optimal trained representative CI time series with the current time duration, the current time duration may be changed to give smaller normalized aggregate mismatch. The current time duration may be initialized with a value based on durations associated with the at least one training CI time series associated with the known event. The current time duration may be initialized with a value based on durations associated with the at least one training CI time series associated with the known event.

At least one of: the first wireless device, and/or the first target wireless receiver, may comprise at least two antennas. Each pair of first wireless device antenna and first target wireless receiver antenna may form a link between the first wireless device and the first target wireless receiver. At least two links may be formed between the first wireless device and the first target wireless receiver. Each link may correspond to a current CI time series.

In one embodiment, the at least one time series of training channel information (CI) of the wireless multipath channel may be obtained from a second wireless signal sent through the wireless multipath channel in a training phase. The wireless multipath channel may be impacted by a training movement of a second object in the training phase. The training phase may be a training session, which may be carried out once, occasionally, regularly, and/or on demand.

At least one time series of first training channel information of the wireless multipath channel associated with a target positive training movement of the second object in the training phase may be obtained. The positive training movement may be a target movement to be recognized, monitored, measured, studied, processed, detected, estimated, verified, and/or captured.

At least one time series of second training channel information of the wireless multipath channel associated with a target negative training movement of the second object in the training phase may be obtained. The negative training movement may be a target movement to be ignored, missed, not monitored, not detected, not estimated, not recognized, not verified, not captured, not measured, and/or not studied.

At least one first quantity from the at least one time series of first training channel information and/or at least one second quantity from the at least one time series of second training channel information may be computed. The at least one first quantity and/or the at least one second quantity may comprise a motion statistics, a location statistics, a map coordinate statistics, a height statistics, a speed statistics, an acceleration statistics, a movement angle statistics, a rotation statistics, a size statistics, a volume statistics, a time trend, a time trend statistics, a time profile statistics, a periodic motion statistics, a frequency statistics, a transient statistics, a breathing statistics, a gait statistics, an action statistics, an event statistics, a suspicious event statistics, a dangerous event statistics, an alarming event statistics, a warning statistics, a belief statistics, a proximity statistics, a collision statistics, a power statistics, a signal statistics, a signal power statistics, a signal strength statistics, a received signal strength indicator (RSSI), a signal amplitude, a signal phase, a signal frequency component, a signal frequency band component, a channel state information (CSI), a CSI statistics, a map statistics, a time statistics, a frequency statistics, a time-frequency statistics, a decomposition statistics, a orthogonal decomposition statistics, a non-orthogonal decomposition statistics, a tracking statistics, a breathing statistics, a heartbeat statistics, a biometric statistics, a baby statistics, a patient statistics, a machine statistics, a device statistics, a temperature statistics, a vehicle statistics, a parking lot statistics, a venue statistics, a lift statistics, an elevator statistics, a spatial statistics, a road statistics, a fluid flow statistics, a home statistics, a room statistics, an office statistics, a house statistics, a building statistics, a warehouse statistics, a storage statistics, a system statistics, a ventilation statistics, a fan statistics, a pipe statistics, a duct statistics, a people statistics, a human statistics, a car statistics, a boat statistics, a truck statistics, an airplane statistics, a drone statistics, a downtown statistics, a crowd statistics, an impulsive event statistics, a cyclo-stationary statistics, an environment statistics, a vibration statistics, a material statistics, a surface statistics, a 3-dimensional statistics, a 2-dimensional statistics, a local statistics, a global statistics, a presence statistics, and/or another statistics.

The at least one threshold may be determined based on the at least one first quantity and/or the at least one second quantity. The at least one threshold may be determined such that a first percentage of the first quantity is larger than, equal to and/or less than a first threshold (not the at least one threshold). The at least one threshold may be determined such that a second percentage of the second quantity is larger than, equal to and/or less than a second threshold (not the at least one threshold).

The first threshold may be greater than, equal to and/or less than the second threshold. The first threshold may be the second threshold. The first percentage may be greater than, equal to and/or less than the second percentage.

The at least one time series of first training channel information of the wireless multipath channel may be associated with a training movement of the second object inside a monitored area in the training phase. The target positive training movement of the second object may be the training movement of the second object inside the monitored area.

The at least one time series of second training channel information of the wireless multipath channel may be associated with a training movement of the second object outside the monitored area in the training phase. The target negative training movement of the second object may be the training movement of the second object outside the monitored area.

The second object may be the first object. The second object may be an imitation, a replacement, a backup, and/or a replica of the first object. The second object may be another object similar to the first object. The second object may be similar to the first object in terms of structure, size, shape, functionality, periodicity, deformation characteristics, motion characteristics, speed, acceleration, gait, trend, habit, wireless properties, and other characteristics.

In one embodiment, the present teaching discloses a method, apparatus, and a system for sleep monitoring. The disclosed method comprises: obtaining a time series of channel information (CI) of a wireless multipath channel using a processor, a memory communicatively coupled with the processor and a set of instructions stored in the memory, and monitoring the sleep-related motion of the user based on the time series of CI.

The time series of CI is extracted from a wireless signal transmitted between a Type 1 heterogeneous wireless device and a Type 2 heterogeneous wireless device in a venue through the wireless multipath channel. The wireless multipath channel is impacted by a sleep-related motion of a user in the venue.

Monitoring the sleep-related motion comprises monitoring at least one of the following of the user: sleep timings, sleep durations, sleep stages, sleep quality, sleep apnea, sleep problems, sleep disorders, breathing problems, gasping, choking, teeth-grinding, pause of sleep, absence of sleep, insomnia, restlessness during sleep, hypersomnia, parasomnia, day-time sleepiness, sleep locations, sleep-while-driving, sleep disruptions, nightmares, night terrors, sleep walking, REM sleep behavior disorder, Circadian rhythm disorder, non-24-hour sleep-wake disorder, periodic limb movement disorder, shift-work sleep disorder, narcolepsy, confusional arousals, sleep paralysis, another sleep-related condition, and/or another sleep-related behavior.

Sleep timings comprises timings of at least one of: go-to-bed, sleep-onset, wake-up, REM-onset, NREM-onset, onset of sleep stage transitions, sleep disorders, sleep problems, breathing problems, insomnia, hypersomnia, parasomnia, sleep hypnogram-related events, sleep disruptions, sleep apnea, snoring during sleep, sleeping-not-on-a-bed, day-time sleep, sleep-walking, sleep-related events, sleep-related condition, and/or, sleep-related behavior, etc.

Sleep stages comprises at least one of: wake-up, rapid-eye-movement (REM) and/or non-REM (NREM).

At least one of: a time function of breathing rate, and a time function of motion statistics, of the user may be computed based on the series of CI. If breathing is not detected at time t, the breathing rate at time t may be computed as zero. The sleep-related motion of the user may be monitored based on at least one of: the time function of breathing rate, and/or the time function of motion statistics, of the user.

At least one of: a time function of breathing ratio, and a time function of motion ratio, of the user may be computed based on the series of CI. The breathing ratio at time t may be computed as percentage of time when the time function of breathing rate is non-zero in a first time window comprising the time t. The motion ratio at time t may be computed as percentage of time when the time function of motion statistics is larger than a first threshold within a second time window comprising the time t. The sleep-related motion of the user may be monitored based on at least one of: the time function of breathing ratio, and/or the time function of motion ratio, of the user.

A sleep stage may be classified as "awake" if at least one of: the motion ratio is greater than a second threshold, and/or the breathing ratio is less than a third threshold. The sleep stage may be classified as "asleep" if at least one of: the motion ratio is less than the second threshold, and/or the breathing ratio is greater than the third threshold. The "asleep" stage may comprise at least one of: rapid-eye-movement (REM) stage, and/or non-REM (NREM) stage.

A breathing rate trend function may be computed by low-pass filtering the time function of breathing rate. A detrended breathing rate function may be computed by subtracting the breathing rate trend function from the time function of breathing rate. A time function of breathing rate variance may be computed by computing variance of the detrended breathing rate function within a sliding time window. The sleep-related motion of the user may be monitored based on the time function of breathing rate variance.

An average NREM breathing rate may be computed by identifying a peak of a histogram of the time function of breathing rate in "asleep" stage in an overnight period. (e.g. the whole night, or the whole night subtracting any "awake" periods). A time function of breathing rate deviation may be computed by computing a distance between the average NREM and a percentile of the breathing rate within a sliding time window. The sleep stage may be classified as at least one of: REM stage and/or NREM stage, based on the time function of breathing rate deviation.

A time function of breathing rate variance may be computed by computing variance of a detrended breathing rate function within a first sliding time window. A time function of breathing rate deviation may be computed by computing a distance between an average NREM and a percentile of the breathing rate within a second sliding time window. The sleep stage may be classified as at least one of: REM stage, and/or NREM stage, based on the time function of breathing rate variance and the time function of breathing rate deviation.

A classifier may be trained based on at least one of: breathing rate variance, and breathing rate deviation, using machine learning. The machine learning may comprise at least one of: supervised learning, unsupervised learning, semi-supervised learning, active learning, reinforcement learning, support vector machine, deep learning, feature learning, clustering, regression, and/or dimensionality reduction. The sleep stage may be classified as at least one of: REM stage, and/or NREM stage, based on the classifier.

A quantity related to the sleep-related motion of the user may be computed based on the time series of CI. The sleep-related motion of the user may be monitored based on the quantity.

The quantity may comprise at least one of: the time the user goes to bed, the time the user gets out of bed, the sleep onset time, total time it takes the user to fall asleep, the wake up time, sleep disruption time, number of sleep disruption period, mean disruption duration, variance of disruption duration, total time in bed, total time the user is asleep, time periods of REM, time periods of NREM, time periods of awake, total time of REM, total time of NREM, number of REM periods, number of NREM periods, time of toss and turn in bed, duration of tossing and turning, hypnogram, periods of apnea, periods of snore, total duration of apnea, number of apnea periods, average duration of apnea period, periods of breathing problems, sleep quality score, daytime sleep, time periods of daytime sleep, total duration of daytime sleep, number of period of daytime sleep, average duration of period of daytime sleep, and another quantity.

Figure 4:
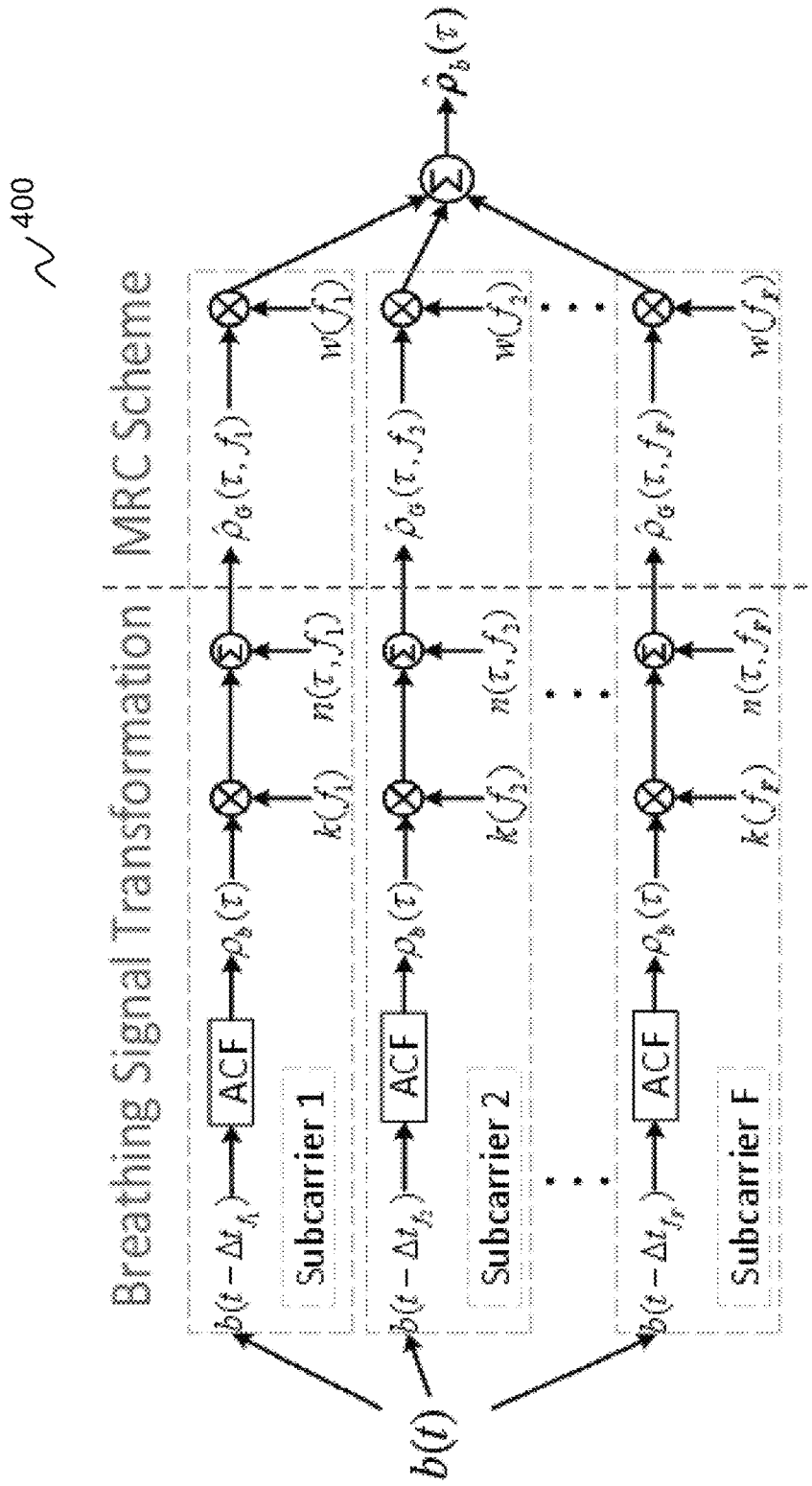
FIG. 4 illustrates an exemplary scheme for breathing signal extraction and maximization, according to one embodiment of the present teaching.
Figure 5:
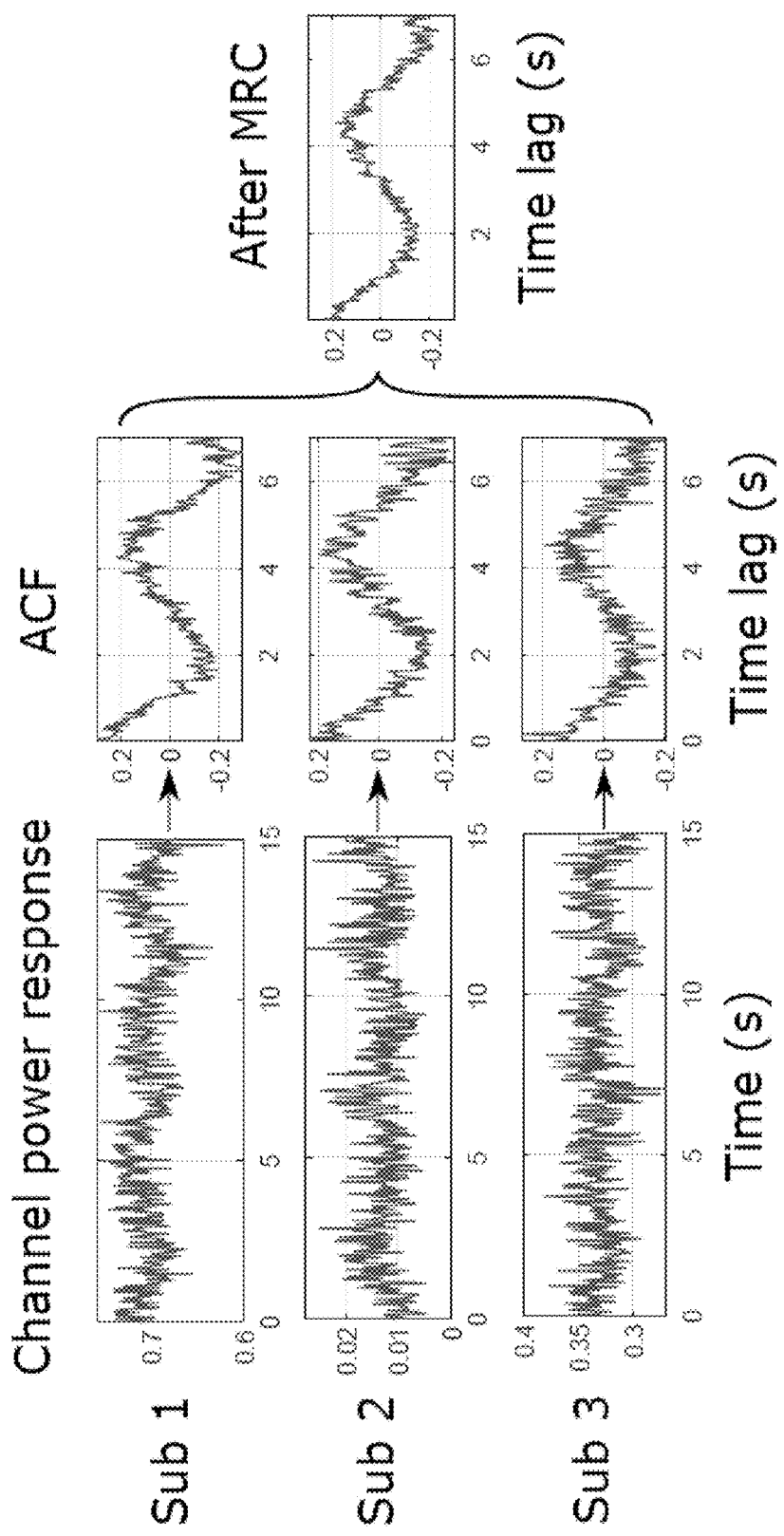
FIG. 5 illustrates an exemplary breathing signal based on real-world measurements, according to one embodiment of the present teaching.
Figure 6:
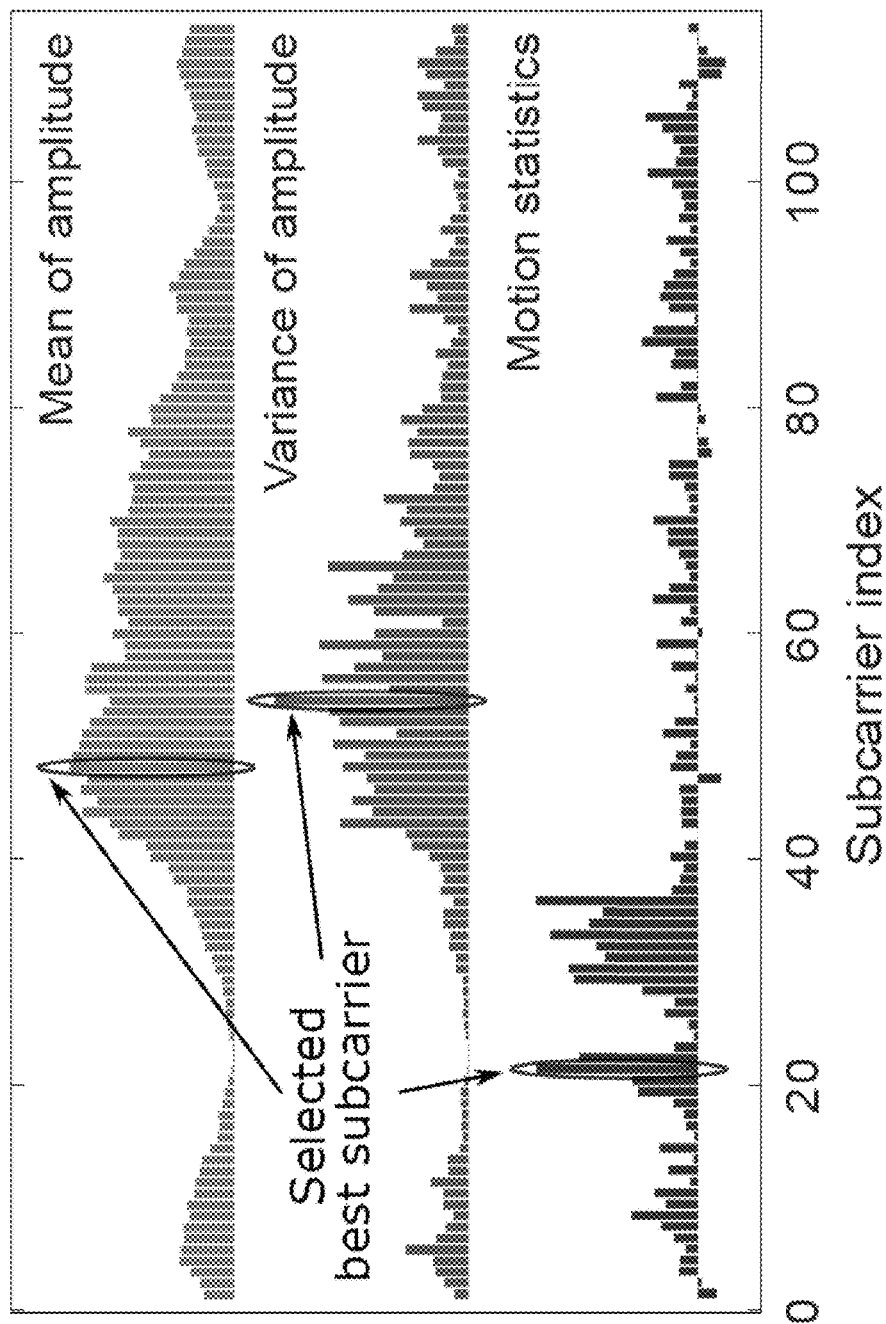
FIG. 6 demonstrates gains of a disclosed scheme for breathing signal extraction and maximization, according to one embodiment of the present teaching.

FIG. 4 summarizes a proposed scheme for breathing signal extraction and maximization. The left part of FIG. 4 shows the decomposition of the measured ACF of the channel power response when a person breathes normally in the monitored area, and the right part shows the MRC scheme for boosting the SNR of the ACF of the breathing signal. FIG. 5 depicts an illustrative example based on real-world measurements, where the SNR of the breathing signal is amplified by 2.5 dB compared to the best subcarrier indicated by largest variance and by 3.7 dB compared to directly averaging all subcarriers. FIG. 6 further demonstrates the gains of the disclosed ACF-based MRC scheme and confirms the observations herein that amplitudes and their variances are not effective metrics for subcarrier selection. As seen, the subcarrier that is the most sensitive to motion (i.e., holding the largest motion statistic) could experience very small amplitude and low variance.

Sleep Stage Recognition

SMARS divides the continuous motion and breathing estimates of overnight sleep into 300-second epochs. For each epoch, SMARS recognizes three different sleep stages, i.e., wake, REM sleep and NREM sleep. The staging is performed in two steps: First, SMARS differentiates wake from sleep mainly by body motions; Second, REM and NREM stages are further identified during sleep period.

Sleep/Wake Detection. SMARS first implements a sleep-wake detector to identify the sleep and wake states. The key insight is that, more frequent body movements will be observed when a subject is awake, while mainly breathing motion presents when he/she is asleep. Since bodily movements are significantly stronger than breathing motions, and both of them can be easily captured and quantified by the motion statistic defined herein, SMARS utilizes it to distinguish between sleep and wake states.

Figure 7A:
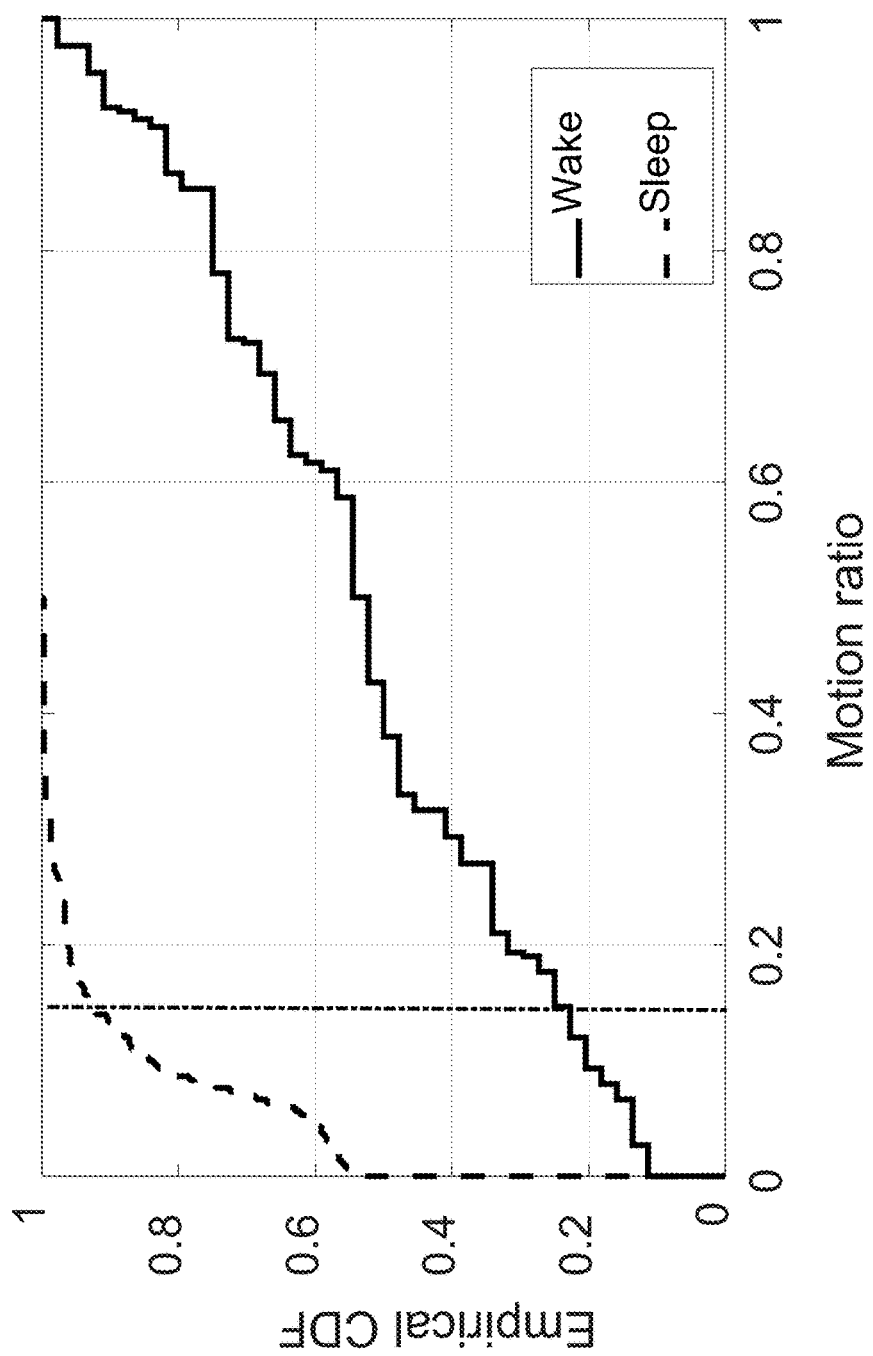
FIG. 7A and FIG. 7B illustrate comparison results between a wake state and a sleep state, according to one embodiment of the present teaching.
Figure 7B:
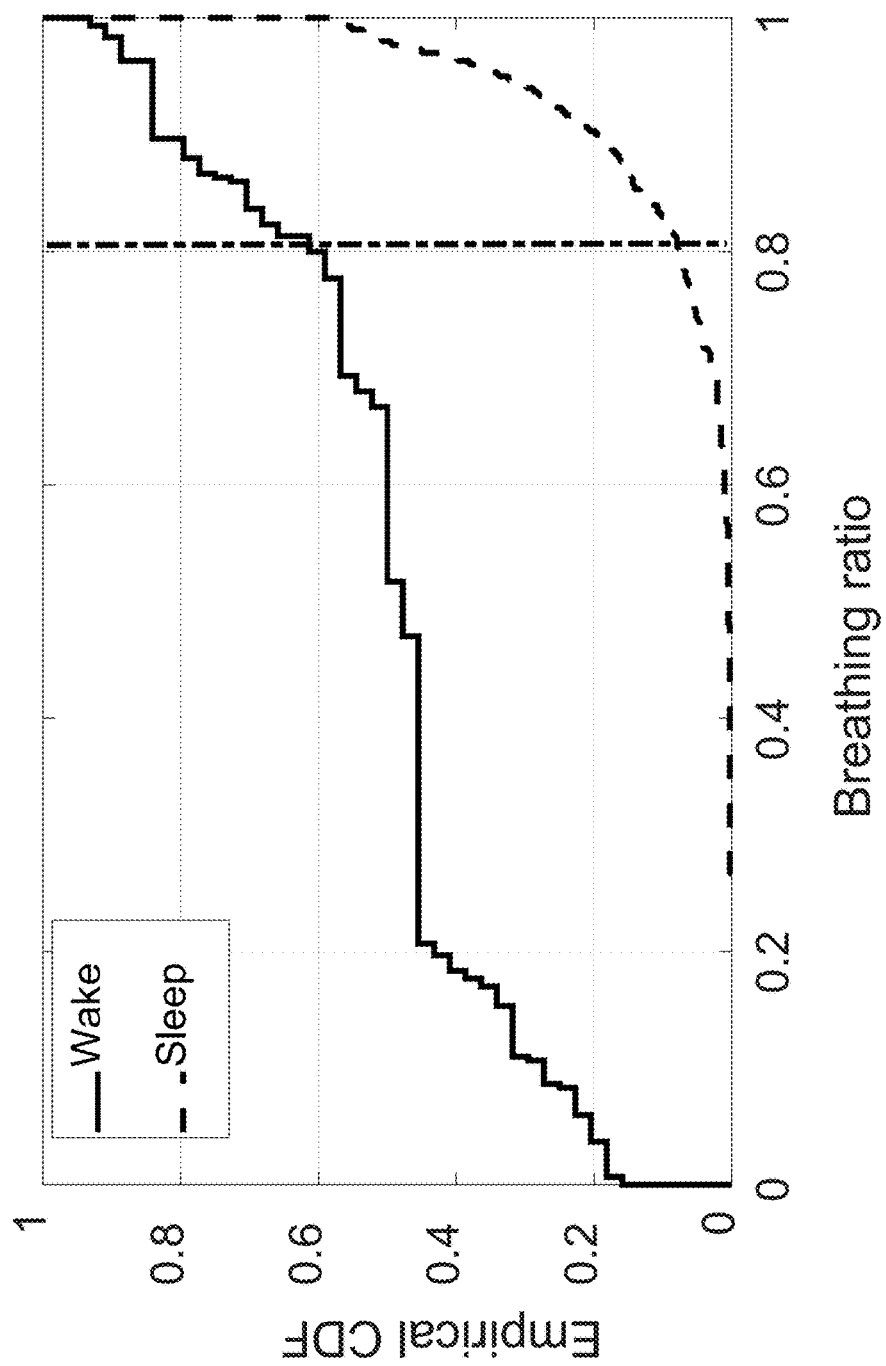

Specifically, one can define motion ratio as the percentage of time when the motion statistic, $\hat{\rho}_b(1/F_s)$, is larger than a preset threshold. Thus for the wake state, a higher motion ratio is expected, as shown in FIG. 7A. Similarly, one can also define breathing ratio as the percentage of time when the breathing signal is detected. Since bodily movements destroy the periodicity of the environmental dynamics, the breathing ratio will be lower when a subject is awake, as shown in FIG. 7B.

Combining the above two features, SMARS identifies an epoch as sleep only when the motion ratio is smaller than the predefined threshold and the breathing ratio is larger than the other threshold. Both thresholds are empirically determined as in FIG. 7A and FIG. 7B. Since the disclosed model statistically considers all multipaths indoors, the values of both thresholds generalize to different environments and subjects.

REM/NREM Recognition. SMARS exploits the following clinical facts and accordingly extracts two distinctive features from breathing rate estimates for REM/NREM stages classification: Breathing rate is usually faster and presents higher variability and irregular patterns for REM stage, while more stable and slower for NREM stage.

Figure 8A:
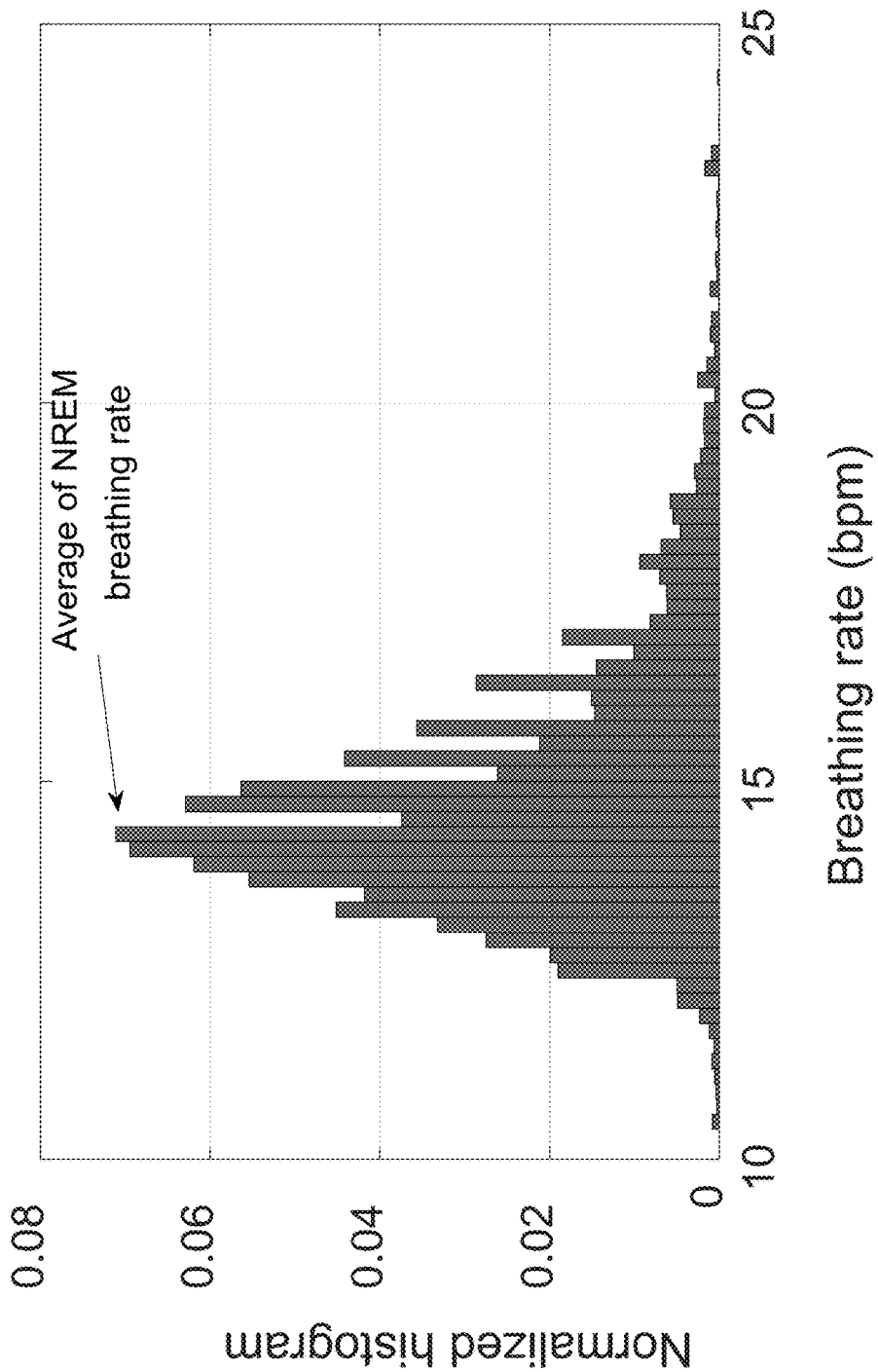
FIG. 8A and FIG. 8B illustrate breathing rate performances of different sleep stages, according to one embodiment of the present teaching.

Since NREM stage constitutes the majority (about 75% to 80%) of total sleep for typical healthy adults, the average breathing rate during NREM stage can be estimated by localizing the peak of the histogram of overnight breathing rate estimates, as shown in FIG. 8A. On this basis, one can define breathing rate deviation, the distance between the estimated average NREM breathing rate and the 90% tile of the breathing rate for each epoch, to quantify the deviation of the breathing rate during REM stage from that during NREM stage.

To extract the variability of the breathing rate for each epoch, one can first estimate the trend of breathing rate by applying a low pass filter to the breathing estimates of the whole night, and obtain the detrended breathing rate estimates by subtracting the trend from the original breathing rate estimates. Then, the breathing rate variability is defined and calculated for each epoch as the variance of the detrended estimates normalized by the length of epoch.

Figure 8B:
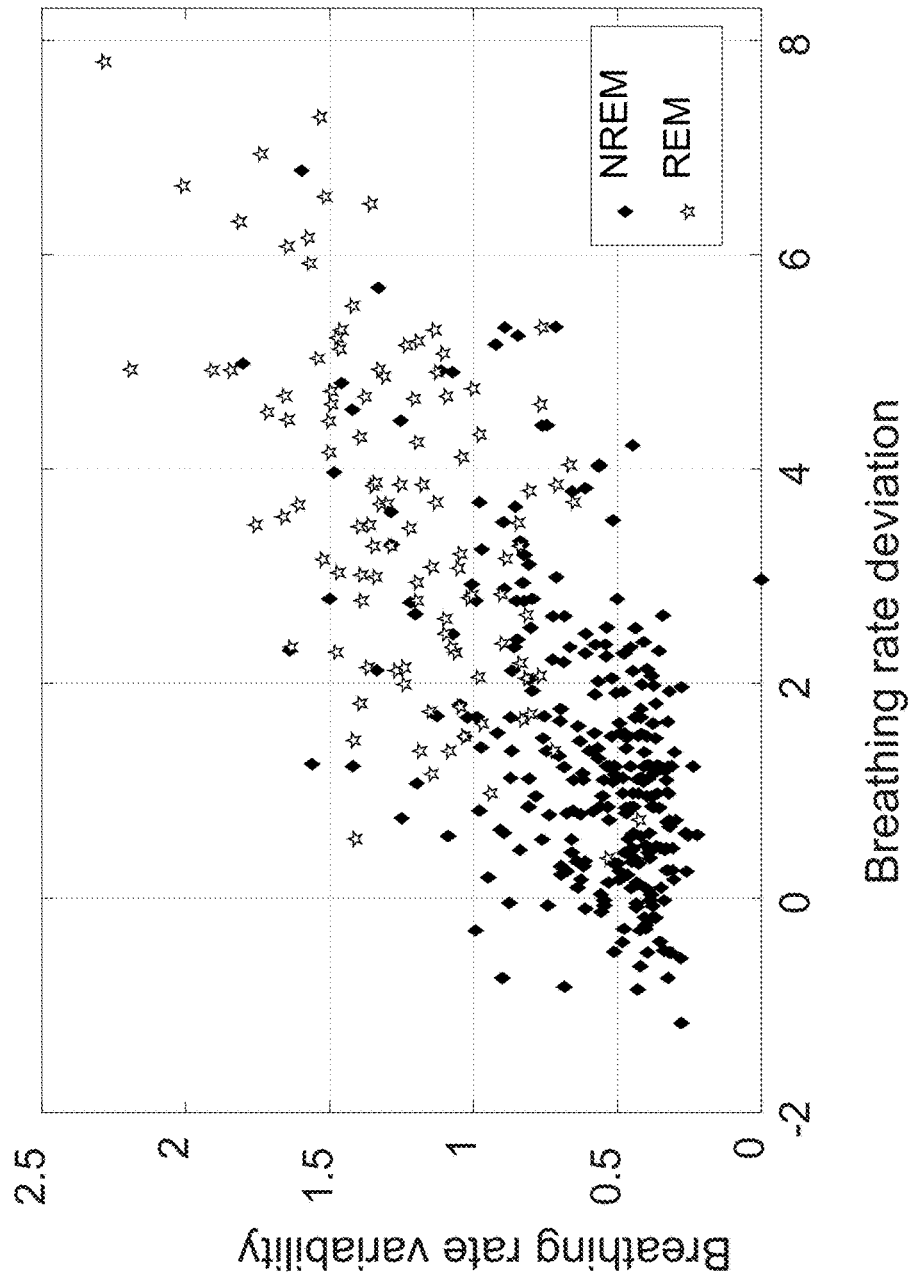

FIG. 8B visualizes the distribution of the proposed two features under NREM and REM sleep, respectively. As one can see from FIG. 8B, the majority of the breathing rate variability and breathing rate deviation of NREM sleep are much smaller than those of REM sleep. Based on these two features, one can train a support vector machine (SVM), a widely used binary classifier, to differentiate between REM and NREM sleep.

Sleep Quality Assessment

When one obtains the estimates of wake, REM, and NREM stages of a whole sleep, one can assess the elusive sleep quality for a user by following standard approach used in clinical practice. In particular, one can calculate the sleep score for each night based on the recognized sleep stages as follows. Let $T_N$, $T_R$ and $T_W$ denote the durations (measured in hours) of NREM sleep, REM sleep and wake, respectively. Since there is no standard formula for sleep score calculation, a simple formula for the sleep score is applied in SMARS:

$$S=10*T_N+20*T_R-10*T_W,$$

which means that the more you sleep, the more you have REM sleep, the less you keep awake in the bed, the better your sleep score is. According to recent research, REM sleep is crucial for mental recovery, and thus a higher weight has been assigned to REM sleep.

Figure 9:
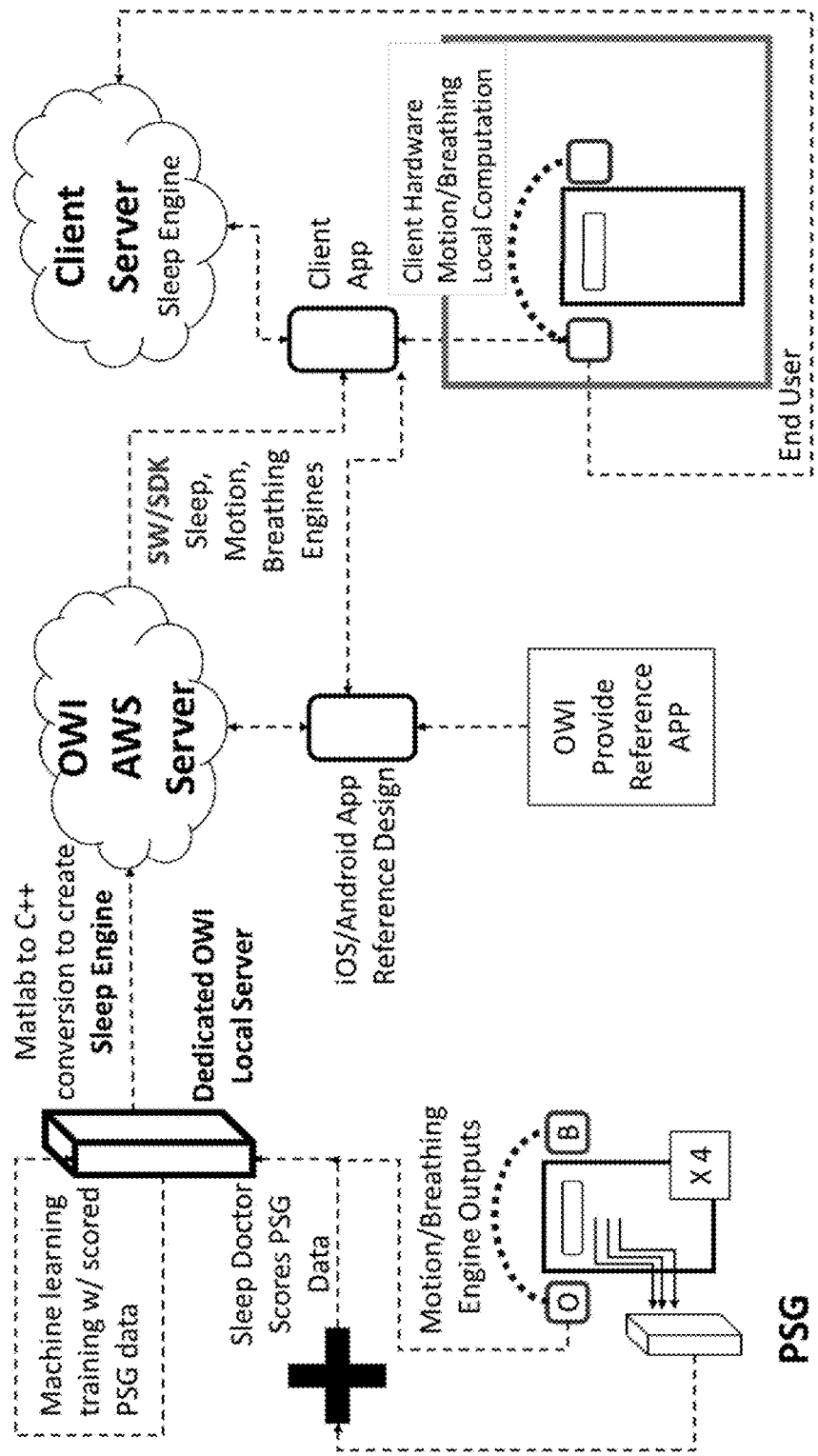
FIG. 9 illustrates an exemplary network environment for sleep monitoring, according to one embodiment of the present teaching.
Figure 10:
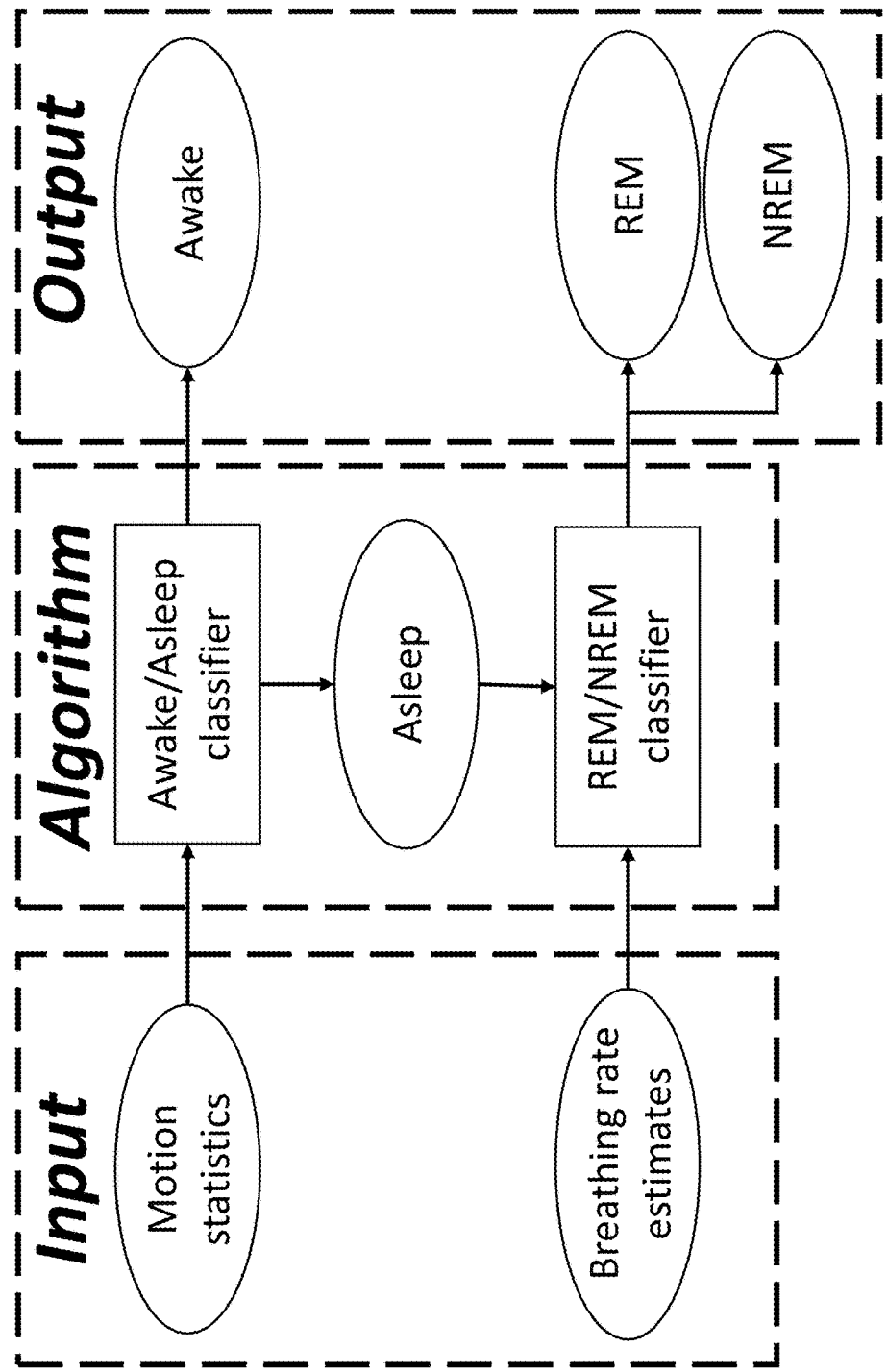
FIG. 10 illustrates an exemplary algorithm design for sleep monitoring, according to one embodiment of the present teaching.

SMARS envisions a practical sleep monitoring for daily in-home use. Although it does not make much sense to compare the sleep score among different users, the trend or history of the sleep score for a particular user would reflect the changes of his/her sleep quality. Such results provide clinically meaningful evidences to help diagnose sleep disorders and manage personal health, in an attractive way. FIG. 9 illustrates an exemplary network environment for sleep monitoring, according to one embodiment of the present teaching. FIG. 10 illustrates an exemplary algorithm design for sleep monitoring, according to one embodiment of the present teaching.

In the era of Internet of Things (IoT), smart appliances are designed and developed to achieve customer satisfaction and convenience and the market for smart appliances is primed. For instance, a Smart TV can deliver an innovative TV usage pattern. Instead of using the conventional remote controller to control a TV at home, with the help of wireless sensing, the Smart TV can be automatically turned on/off, paused and/or resumed by detecting certain motion patterns in front of the TV and by sensing the presence of a human in a certain area, e.g., the living room. In one embodiment, the present teaching discloses monitoring the presence of a live object and potential motion of the object based on time-reversal technology in a rich-scattering environment, e.g. an indoor environment or urban metropolitan area, enclosed environment, underground environment, etc.

Figure 11:
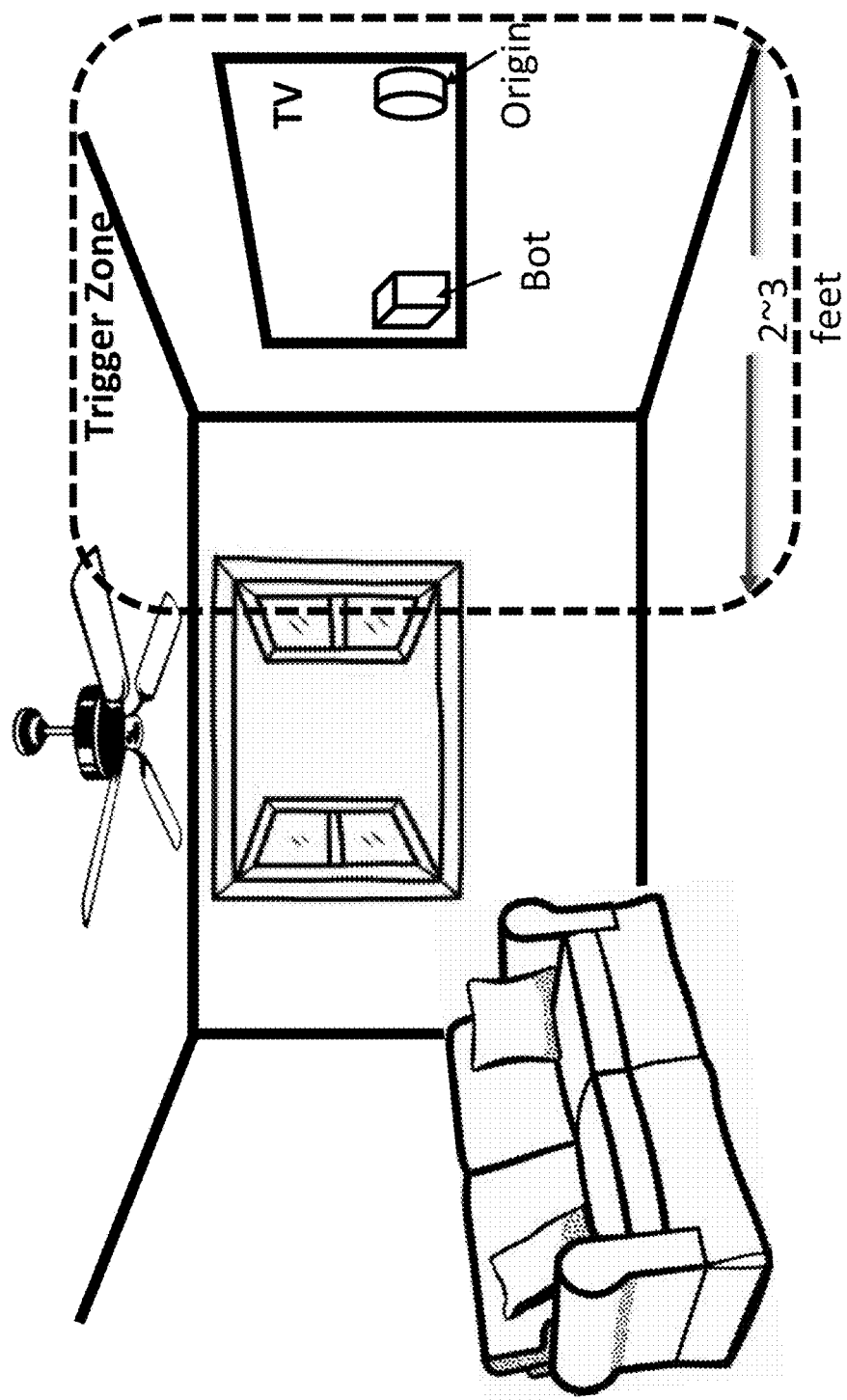
FIG. 11 illustrates an exemplary demonstration of a Smart TV use case, according to one embodiment of the present teaching.

As shown in FIG. 11, hang on the wall of the living room, the Smart TV has one Origin and one Bot, i.e., two WiFi transceivers, embedded inside of it to sense the wireless propagation environment of the living room. When the user is pacing around in front of the TV within a certain distance, e.g. 2 to 3 feet from the TV, the TV will detect it by sensing the environment with the Origin and the Bot and capturing and analyzing the channel state information (CSI), and will finally automatically turn on. When the user is watching the TV and sitting on the sofa, even it might be far away from the TV, the Origin and the Bot can still capture the perturbation introduced to the CSI by the motion or vital signals of the present user. Only when no one is in the living room, the propagation environment will be quiet and the CSI will be consistent along the time and can be sensed by the Origin and the Bot inside the Smart TV. In other words, with the help of the Origin and the Bot inside the Smart TV, the Smart TV can sense the indoor environment wirelessly and differentiate between different indoor states: (1) when the user is pacing close to the TV within the target area (2 to 3 feet), (2) when the user is sitting on the sofa and watching TV (i.e., daily activity inside the living room), and (3) when the room is empty and no one is there.

In the designed scheme of one embodiment, the Smart TV will turn on and off automatically as a response to the three detected indoor states. When TV is on (or off) and state (1) is detected, the TV will be turned off (or on) immediately. When the TV is on and state (2) is detected, the TV will remain as on. When the TV is on and state (3) is detected for a certain time period, the TV will enter into a countdown mode. During the count-down period and before the count-down limit is reached, if the state (2) is detected, the TV will remain on and the count-down mode is reset and disabled. However, if the state (3) persists during the count-down period, the TV will be shut down when the countdown limit is reached.

Methodology:

In the Smart TV, the Bot keeps transmitting channel probing signals to the Origin at a given sounding rate 1/Ts where Ts is the channel probing interval in seconds. Based on each received channel probing signal, the Origin can estimate the channel state information (CSI). For every 1/Ts CSI, a motion statistic value (metric) is derived as the averaged auto-correlation value between adjacent CSIs for a total of M consecutive CSIs. Due to the nature of multipath propagation, the CSI will be disturbed when users are inside the room and different activities will result in a different motion pattern in the CSIs. When the motion is close to the Smart TV (the Origin and the Bot), a larger motion statistic value will be produced than the one associated to when the motion is away from the TV. When there is no motion inside the room, the corresponding motion statistics will be very small, e.g. around 0. Hence, by using motion statistics, the aforementioned 3 indoor states can be categorized well.

Algorithm:

Different algorithms are disclosed to guarantee the accuracy as well as the robustness of the proposed Smart TV system.

A) To detect state (1) when the user is pacing in front of the TV, a first-in-first-out buffer B_1 with a fixed length W_1 is used to store the latest motion statistics calculated from incoming CSIs. The median value X_1 of all elements in buffer B_1 is used as the metric. X_1 keeps updating and is compared with a predefined threshold R_1. When X_1>R_1, it is determined that state (1) is detected and the Smart TV will be turned on (or off) if its current state is off (or on).

B) Meanwhile, to detect state (3) when no one is inside the room, another first-in-first-out buffer B_2 with a fixed length W_2 is used to store the latest motion statistics calculated from incoming CSIs. The median value X_2 of all elements in buffer B_2 is used as the metric. X_2 keeps being updated and is compared with a predefined threshold R_2. When X_2<R_2, it is determined that state (3) is detected and the Smart TV will enter the countdown mode with the countdown limit being T_0. During the countdown mode and before the limit T_0 is reached, the Origin and the Bot keeps sensing the indoor propagation environment and updating the buffer B_1 and B_2 with latest motion statistics. Meanwhile, a new first-in first-out motion statistics buffer B_3 is opened with length W_3 and it is aimed to detect if the state (2) or any motion happens during this period. The median value X_3 of all elements in buffer B_3 is used as the metric and compared with a predefined threshold R_3. When X_3>R_3, it is determined that state (2) is detected, i.e., there is motion or the user present in the room. During the countdown period, if the state (2) is detected, the countdown will be terminated and the Smart TV will not be shut down. Otherwise, the Smart TV will automatically shut-down when the countdown limit is reached.

C) The length of each buffer is adjustable. Typically, W_1 is 5 seconds, W_2 is 15 seconds, W_3 is 5 seconds and T_0 is 30 seconds. The threshold of R_1, R_2, and R_3 can be adjusted manually or learned through a training process during the initial set-up.

The Smart TV disclosed herein may display any video on a TV screen. In one embodiment, the video can be paused and/or resumed automatically as a response to the three detected indoor states: (1) when the user is pacing close to the TV within the target area (2 to 3 feet), (2) when the user is sitting on the sofa and watching TV (i.e., daily activity inside the living room), and (3) when the room is empty and no one is there. When the TV is on and playing any video on the screen, if the state (1) is detected, the TV will immediately pause and start a countdown period T_1. During the countdown period of T_1, if the state (1) is detected again, the TV will resume and start to play from the paused scene. If state (1) is never detected while the state (2) is detected, the TV will remain paused with its screen being on and showing the paused scene. However, if the state (3) keeps being detected during the countdown period of T_1, i.e. none of the state (1) or the state (2) has been detected before the countdown limit T_1 is reached, the TV will enter the sleep mode with the display being off and start another countdown period T_2. During the countdown period of T_2, if the state (1) is detected, the TV will immediately light up and start to play from the paused scene. If the state (2) is detected instead of the state (1), the TV will immediately light up, stay in the pause mode, and show the paused screen. However, if before the limit T_2 is reached, none of the state (1) or the state (2) has ever been detected, i.e., the TV detects the state (3) all the time, then the TV which is in the sleep mode will turn off automatically, but remember the last scene before it is paused.

Algorithm:

Different algorithms are disclosed to guarantee the accuracy as well as the robustness of the proposed Smart TV system.

A) To detect the state (1) when the user is pacing in front of the TV, a first-in-first-out buffer B_1 with a fixed length W_1 is used to store the latest motion statistics calculated from incoming CSIs. The median value X_1 of all elements in buffer B_1 is used as the metric. X_1 keeps updating and is compared with a predefined threshold R_1. When X_1>R_1, it is determined that state (1) is detected and the Smart TV will be paused or resumed given its current state. If the current state of the Smart TV is being paused, the Smart TV will immediately resume to play from the paused scene. However, if the Smart TV was playing a movie and it is being paused as a response to the detection of the state (1), a countdown mode of limit T_1 will be started immediately to decide if the Smart TV enter the sleep mode or not.

B) Meanwhile, to detect the state (3) when no one is inside the room, another first-in-first-out buffer B_2 with a fixed length W_2 is used to store the latest motion statistics calculated from incoming CSIs. The median value X_2 of all elements in buffer B_2 is used as the metric. X_2 keeps being updated and is compared with a predefined threshold R_2. When X_2<R_2, it is determined that state (3) is detected.

C) Moreover, a first-in first-out motion statistics buffer B_3 is opened with length W_3 and it is aimed to detect if the state (2) or any motion happens during this period. The median value X_3 of all elements in buffer B_3 is used as the metric and compared with a predefined threshold R_3. When X_3>R_3, it is determined that state (2) is detected, i.e., there is motion or the user present in the room.

D) During the countdown of T_1 and before the limit T_1 is reached, the Origin and the Bot keeps sensing the indoor propagation environment and updating the buffer B_1, B_2, and B_3 with latest motion statistics. If the state (1) is detected before the limit T_1 is reached, the Smart TV will immediately resume and continue to play from the paused scene, and the countdown will be terminated. If the state (1) is not detected but the state (2) is detected before the limit T_1 is reached, the countdown of T_1 will be reset and started over again while the Smart TV remains in the paused mode. On the other hand, if none of the state (1) or the state (2) is detected, i.e., the Origin and the Bot in the Smart TV keeps detecting state (3), the TV will enter the sleep mode with the display being off when the countdown limit T_1 is reached.

E) As soon as the Smart TV enters the sleep mode, a new countdown of limit T_2 starts. During the countdown of T_2, the Smart TV keeps its display off until any of the following three cases happens. If the state (1) is detected, the countdown of T_2 will be terminated and the Smart TV will light up and resume to play from the paused scene immediately. If the state (2) is detected, the countdown of T_2 will be terminated while the countdown of T_1 will start over again. Meanwhile, the Smart TV will light up, remain paused with the display showing the paused scene. If the state (3) keeps being detected, i.e., none of the state (1) or the state (2) is detected, the Smart TV in the sleep mode will be turned off automatically at the time when the countdown limit T_2 is reached.

C) The length of each buffer is adjustable. The threshold of R_1, R_2, and R_3 can be adjusted manually or learned through a training process during the initial set-up.

Figure 12:
FIG. 12 illustrates an exemplary setting of Smart TV with deployment of devices under the TV, according to one embodiment of the present teaching.
Figure 13:
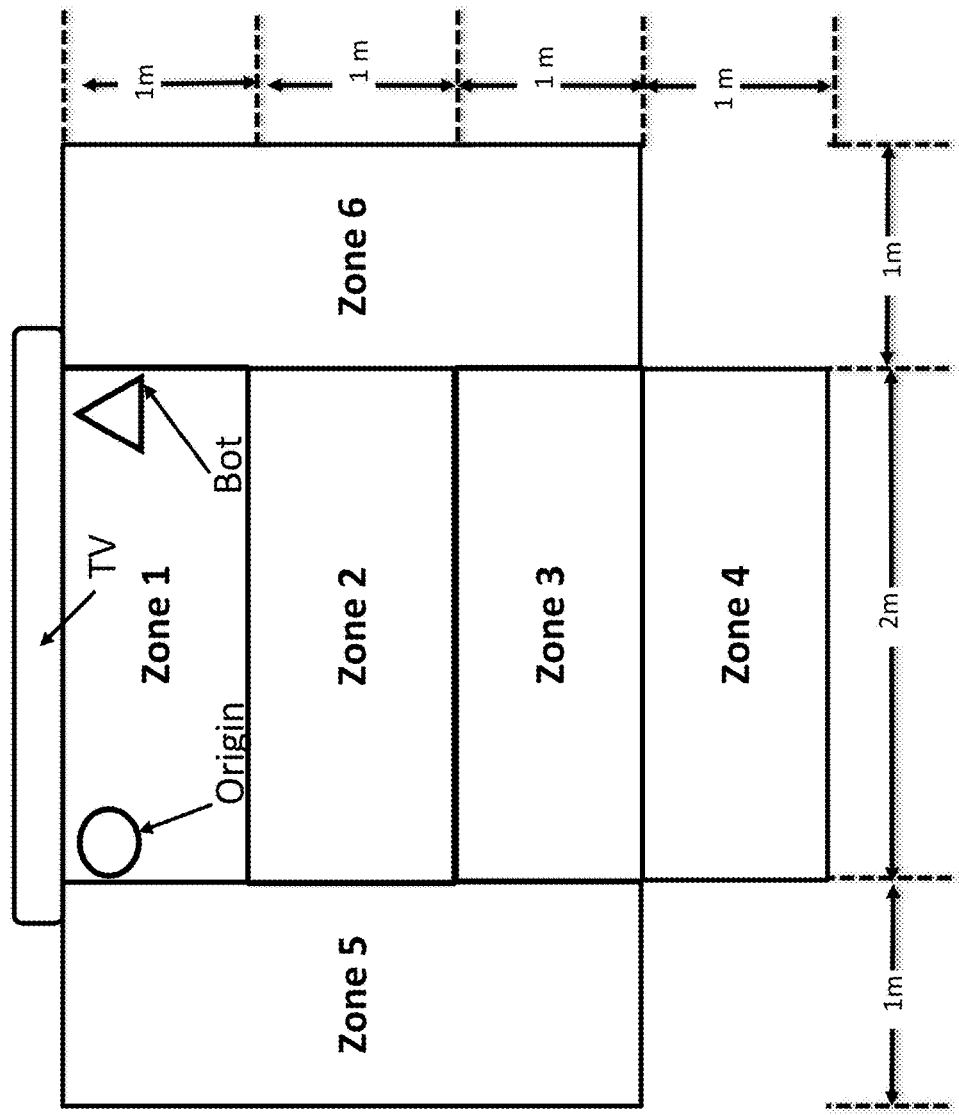
FIG. 13 illustrates an exemplary experiment setting of Smart TV with area partition in front of the TV, according to one embodiment of the present teaching.

Experimental Results:

To validate and demonstrate the idea of Smart TV, experiments are conducted and the set-up is shown in FIG. 12 where the Origin and the Bot are put at the left and right boundary of the TV, right under the TV. The space in front of the test TV is partitioned into 6 zones as shown in FIG. 13 and the Zone 1 which is within 1 meter from the TV is considered as the intended area of the state (1).

The CSI between the Origin and the Bot can be collected to calculate the motion statistics for cases when one tester is pacing in each zone for 1 minute and for the case when the room is empty for 1 minute. The distributions of statistics corresponding to different scenarios are plotted as the cumulative distribution function (CDF), where the legend "CX" means the scenario of user pacing in Zone X. It is clear that almost 90% of the statistics for an empty room are below 0, while almost 90% of statistics of pacing in Zone 1 are above 0.6. For other motion inside the room, most of the motion statistics fall into the range of 0.1 to 0.5. Hence, with the help of motion statistics, the proposed Smart TV is capable of differentiating between those 3 indoor states.

Based on motion statistics and the system output (turn-on detection) along the time for the user pacing at different zones, when the turn-on detection is one, the Smart TV will be turned on (off) automatically. 100% of detection is achieved for Zone 1, i.e. the intended trigger zone, and 0 false alarm for other zones.

Based on motion statistics and the system output (activity detection) along the time for both the scenarios of an empty room and someone sitting in Zone 4, when the activity detection is 1, the TV will not be turned off. When the activity detection is 0, the TV will be turned off after the countdown. The motion statistics may be sensitive and capable of detecting tiny and distant motion, while maintaining its robustness for an empty room.

Based on results of 5 turn-on tests and 5 passing-by tests, as the user is intentionally pacing in Zone 1 to activate the state (1), the proposed Smart TV system can always capture and respond to it quickly and accurately. When the user is only walking through Zone 1 randomly without an intention to activate the state (1), the proposed Smart TV system will never produce false alarm which demonstrates its robustness.

Potential Use Cases:

By utilizing the CSI that characterizes the indoor environment to detect and distinguish different indoor environments, the disclosed Smart TV system is intelligent and capable of turning on and off the TV automatically based on the indoor states of when no one is in the room, when the user is within the room performing daily activities and/or when the user is pacing in front of the TV. The disclosed Smart TV system can detect motion in close proximity, and quickly respond to it. Meanwhile, the disclosed system can also be extended to other smart appliances, such as the refrigerator, the electric fireplace, the display screen for advertising and so on.

Figure 14:
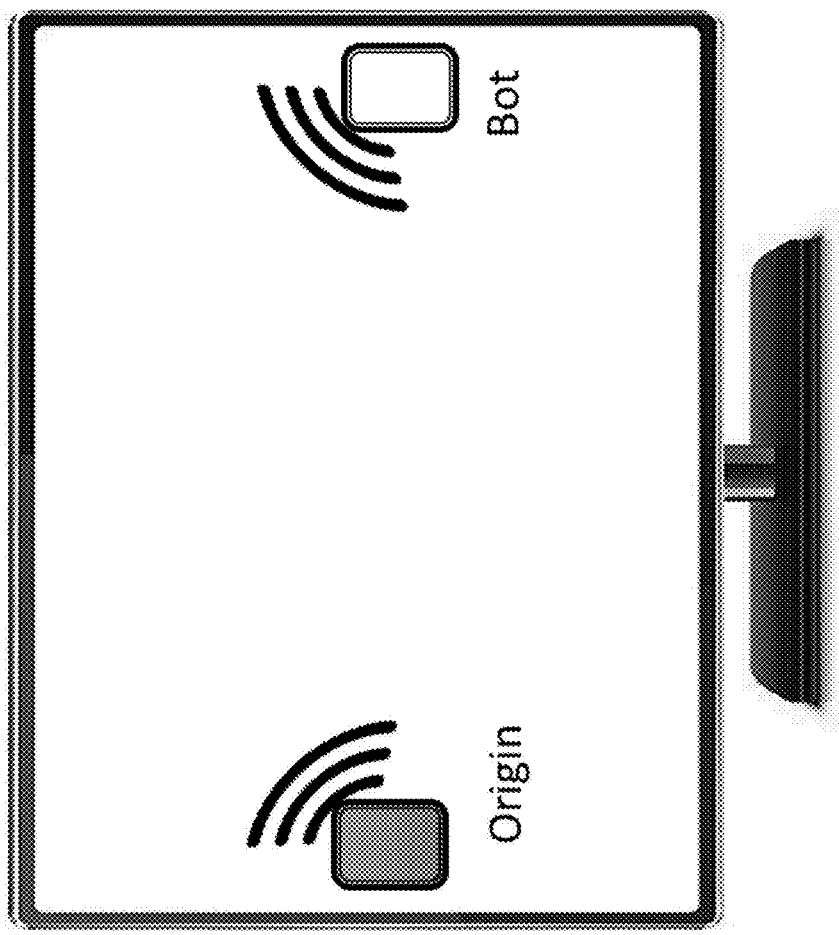
FIG. 14 illustrates an exemplary setting of Smart TV with deployment of devices inside the TV, according to one embodiment of the present teaching.
Figure 15:
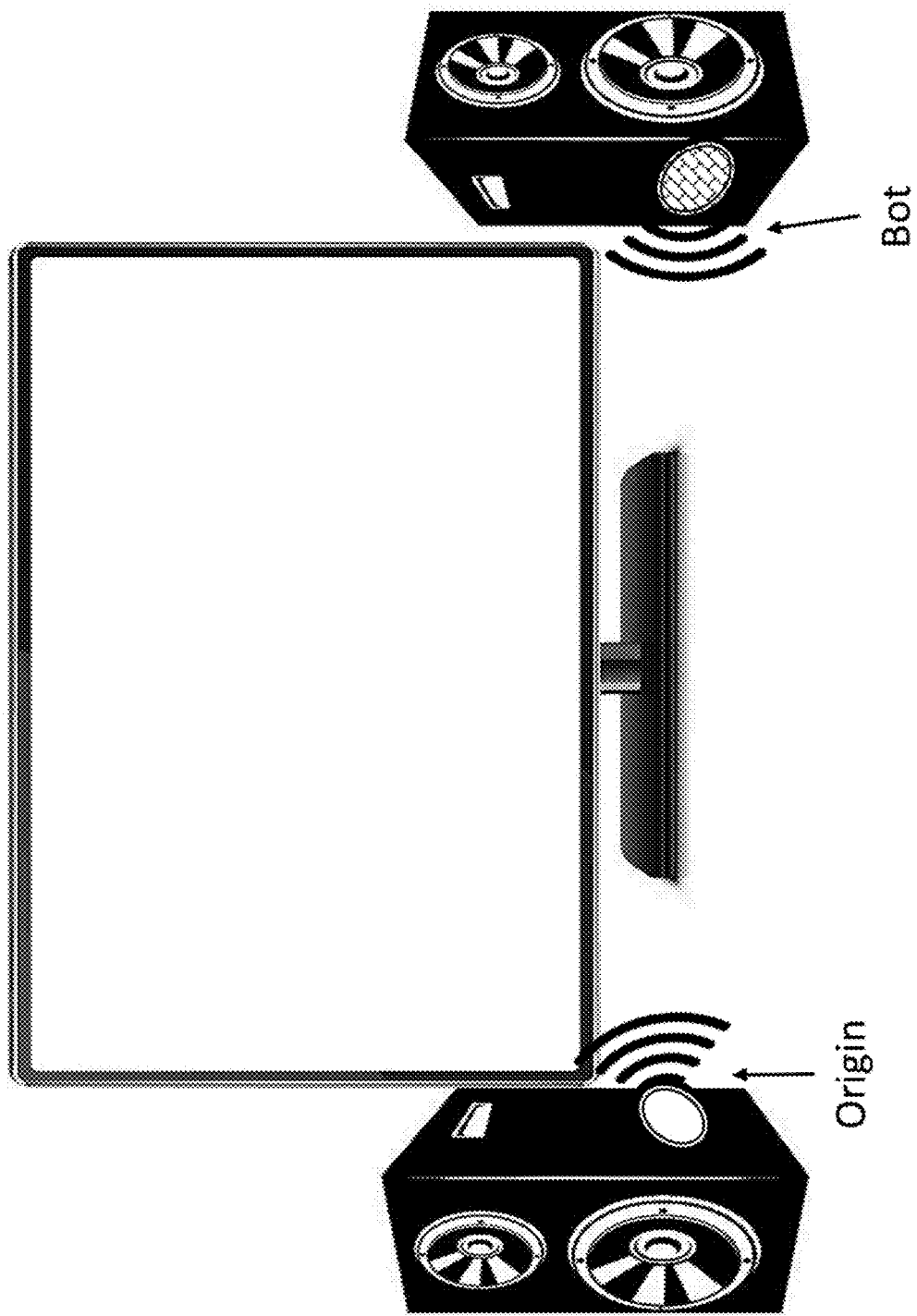
FIG. 15 illustrates an exemplary setting of Smart TV with Origin and Bot installed in a speaker close to the TV, according to one embodiment of the present teaching.
Figure 16:
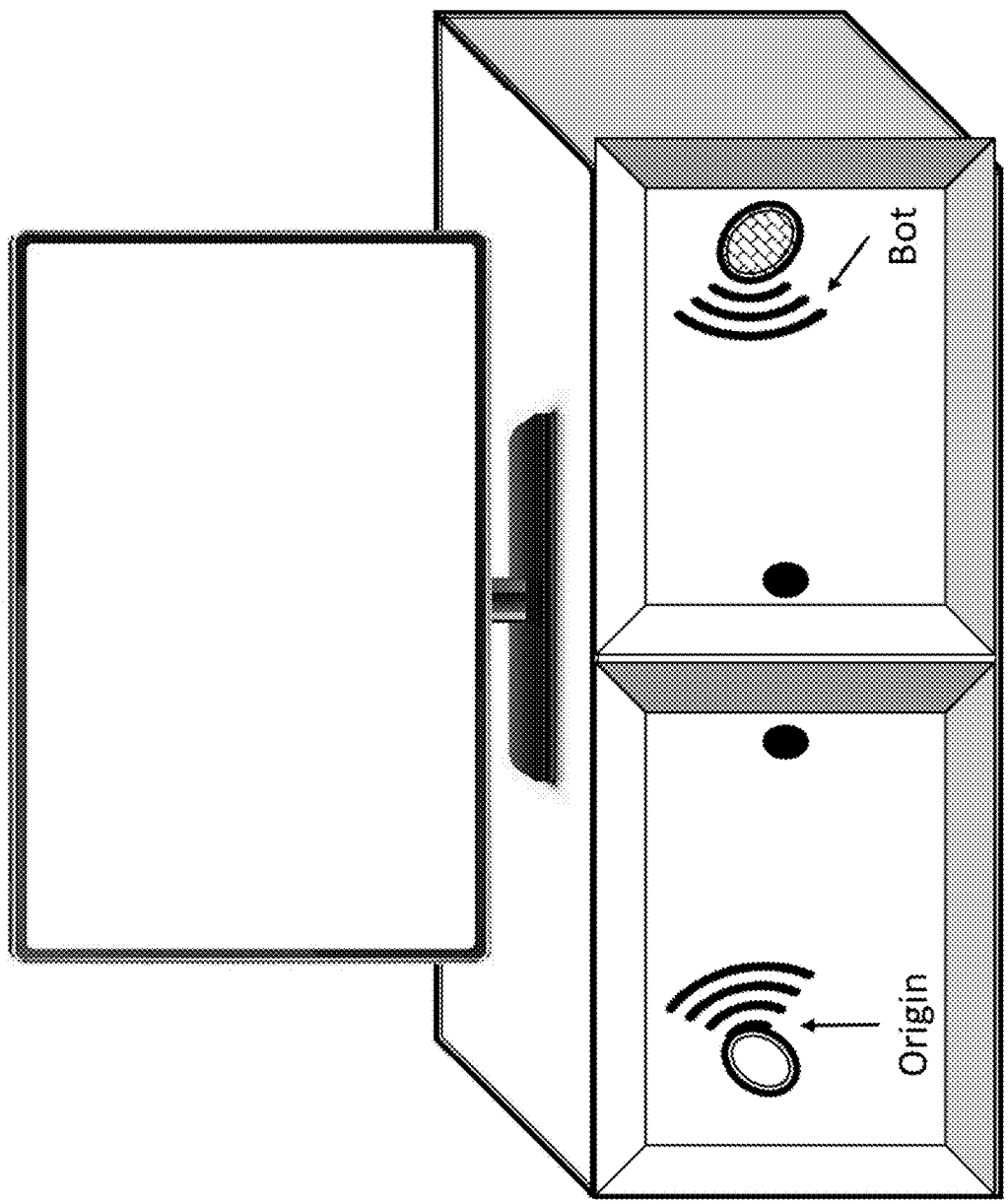
FIG. 16 illustrates an exemplary setting of Smart TV with Origin and Bot installed on a table close to the TV, according to one embodiment of the present teaching.

FIG. 14 illustrates another exemplary setting of Smart TV where the Origin and/or Bot may be integrated into the TV for presence detection. FIG. 15 illustrates another exemplary setting of Smart TV where the Origin and/or Bot may be installed in a speaker placed in front of the TV for presence detection. FIG. 16 illustrates another exemplary setting of Smart TV, with TV placed on a table, and Origin/Bot installed on the table. The table can be computer furniture to house the computer, or entertainment center to house the TV.

Figure 17:
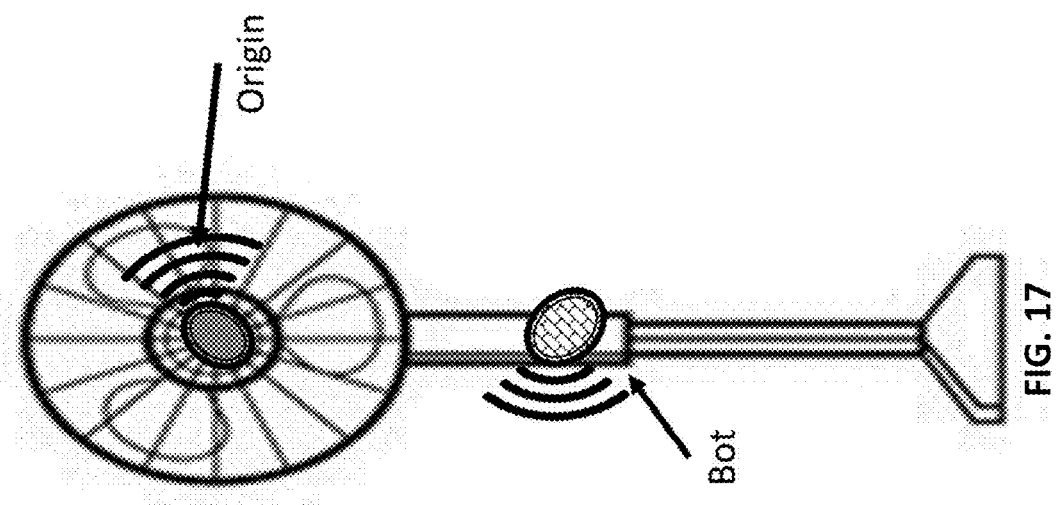
FIG. 17 illustrates an exemplary setting of Smart fan with Origin and Bot installed on the high stand of the fan, according to one embodiment of the present teaching.

FIG. 17 illustrates another scenario of a smart fan. The fan may be a standing fan with a high stand and the Origin and/or Bot may be installed on the high stand. When a person is detected, either through motion detection or vital signs (such as breathing) detection, the fan can be turned on.

Figure 18:
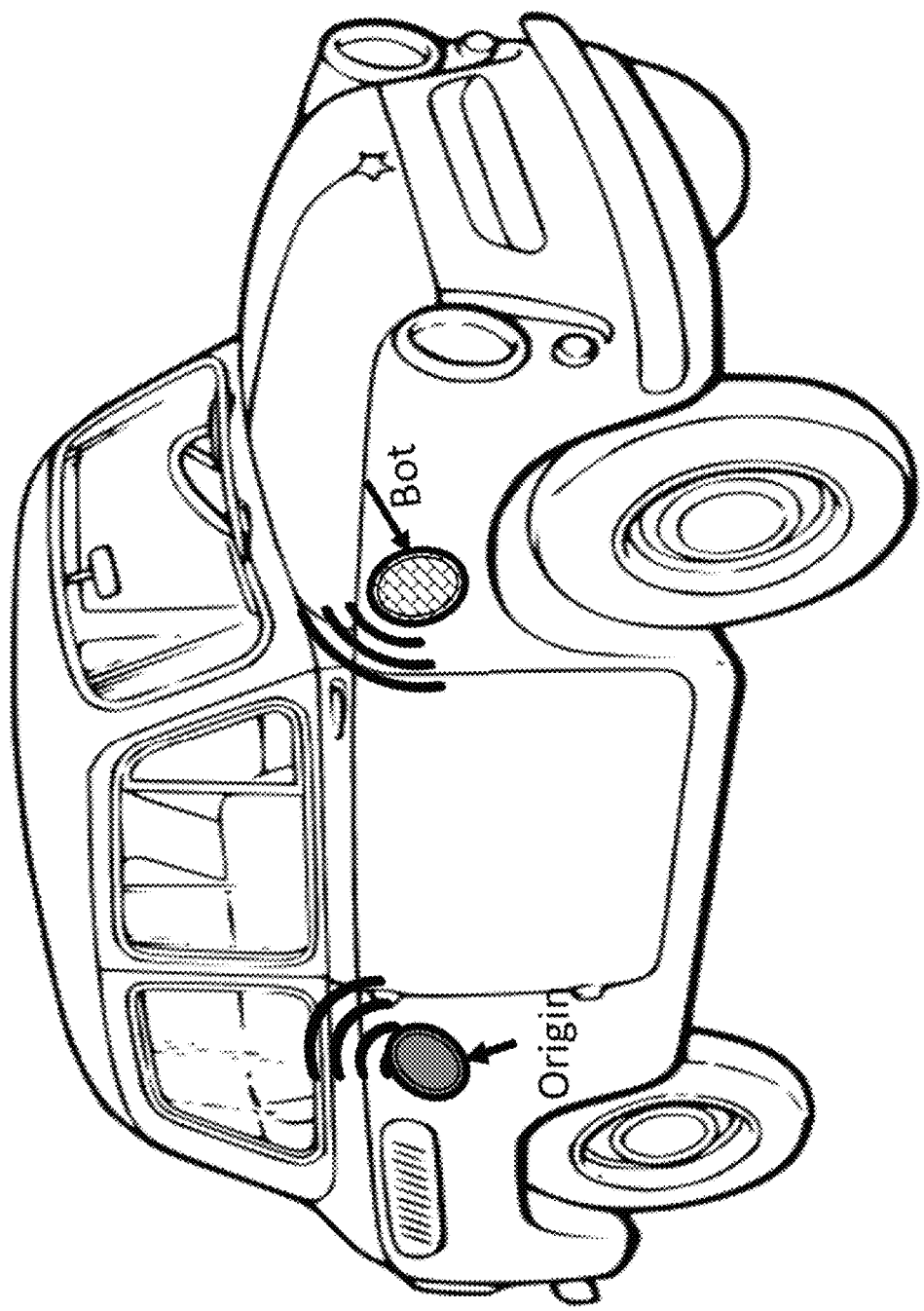
FIG. 18 illustrates an exemplary setting of Smart car with Origin and Bot installed outside of the car, according to one embodiment of the present teaching.

FIG. 18 illustrates another scenario of a smart car. The Origin and Bot may be installed on the outside of a car. When human presence is detected, the car may do something: e.g. activate security; check ID of the person; if the user is confirmed, the car may open the door, trunk, and etc. or start engine (warm up) or start AC to cool the car.

Figure 19:
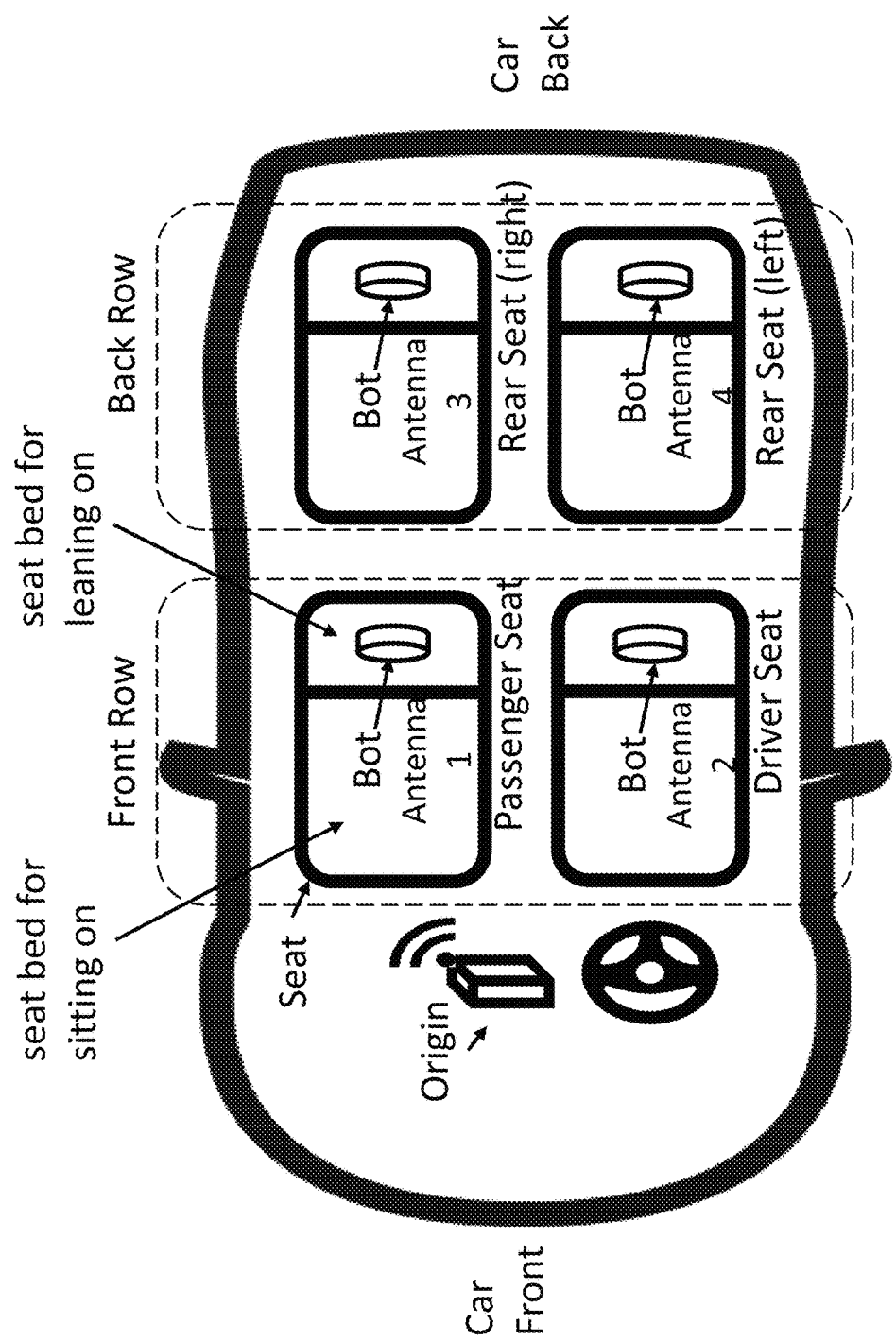
FIG. 19 illustrates an exemplary interior bird-view of a car for seat occupancy detection and people counting, according to one embodiment of the present teaching.

FIG. 19 illustrates an exemplary interior bird-view of a car for seat occupancy detection and people counting, according to one embodiment of the present teaching. In an example, one or more Type 1 devices and multiple Type 2 devices (e.g. N=4) may be placed in a confined area (e.g. closed area such as a car, a conference room, a bus, an airplane, or a cinema, semi-open area such as a bus with windows open, or a balcony with 8 outdoor chairs around an outdoor table) with multiple "seats" at fixed locations (may be a space for standing, sitting, kneeling, lying down, etc.) that may hold a person. A presence of a person at one or more "seats" may be detected based on time series of CI extracted from wireless signals sent from the Type 1 devices to the Type 2 devices.

FIG. 19 shows a particular example of a car with 4 seats, two in front row and two in back row. Note that each seat has a "seat bed" for a person to sit on and a "seat back" for a person to lean back on. The Type 1 device may be placed in the front, on the dash board. Four Type 2 devices may be deployed, one at each of the 4 seats (e.g. in/on/under the seat bed, or in/on/under the seat bed). When a seat A (e.g. driver seat, or right seat on front row, or back row left seat, etc.) is occupied by the driver or a passenger or a baby in a car-seat, the CI (channel information) associated with the occupied seat A may behave differently (e.g. become smaller or bigger) from the CI associated with an empty seat A. Thus one can detect the seat occupancy of each seat by examining the CI. By performing such test for all the seats, one can count the amount of people in the car. If a person sits at non-standard locations (e.g. between two seats, in the center of back row, in the center of front row, or a baby in a car seat), CI associated multiple Type 2 devices can be analyzed jointly to determine if there is a person there. As signature of a baby in car-seat may be different from an adult or a children, adult/children/baby classification may be performed based on the CI.

A task may be performed based on the seat occupancy described above. For example, the task may be to arm an air-bag if a seat is occupied, but disarm the airbag if the seat is not occupied. If a small size person (e.g. a child) instead of a regular-size adult is detected, an air-bag designed for adults may not be armed. The heating/air-condition setting may be adjusted. The task may be to control windows, lighting, audio system, entertainment system (e.g. video), noise cancelling, shock-absorbing system, stabilizing size, car avoidance system, safety features, tire pressure, any other car subsystems, etc. For example, if a passenger is detected at the front right seat, the temperature at that region (front, right) may be controlled to a preset level. If the seat is empty, the temperature may be adjusted differently.

Figure 20A:
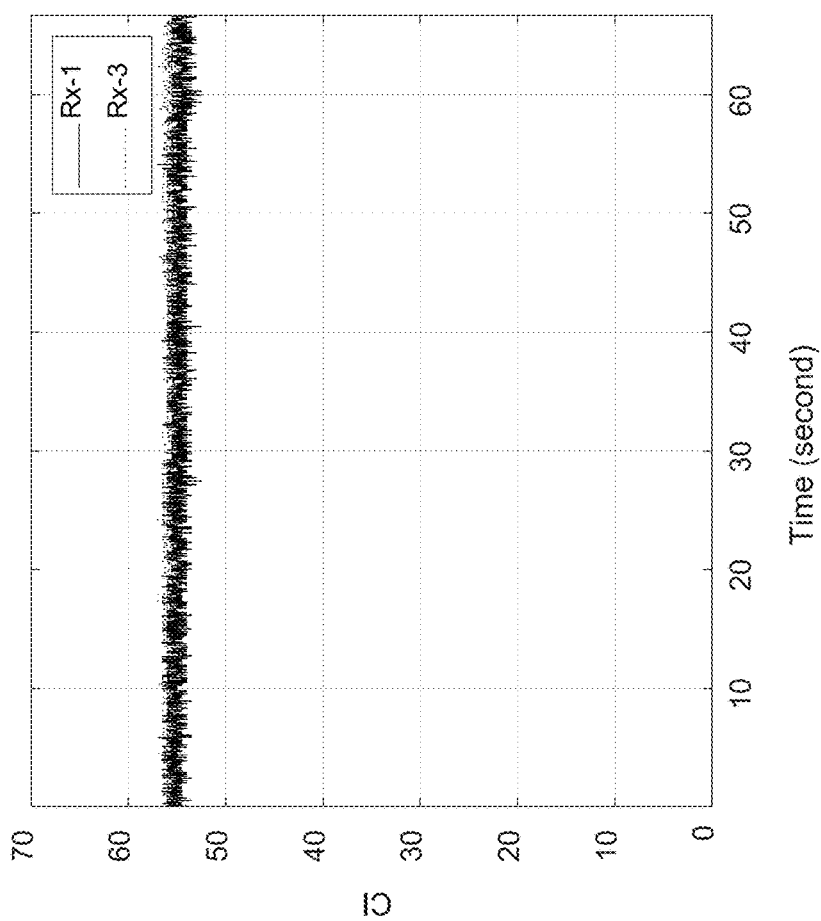
FIGS. 20A-20D illustrate changes of channel information according to various seat occupancy situations in a car, according to one embodiment of the present teaching.
Figure 20B:
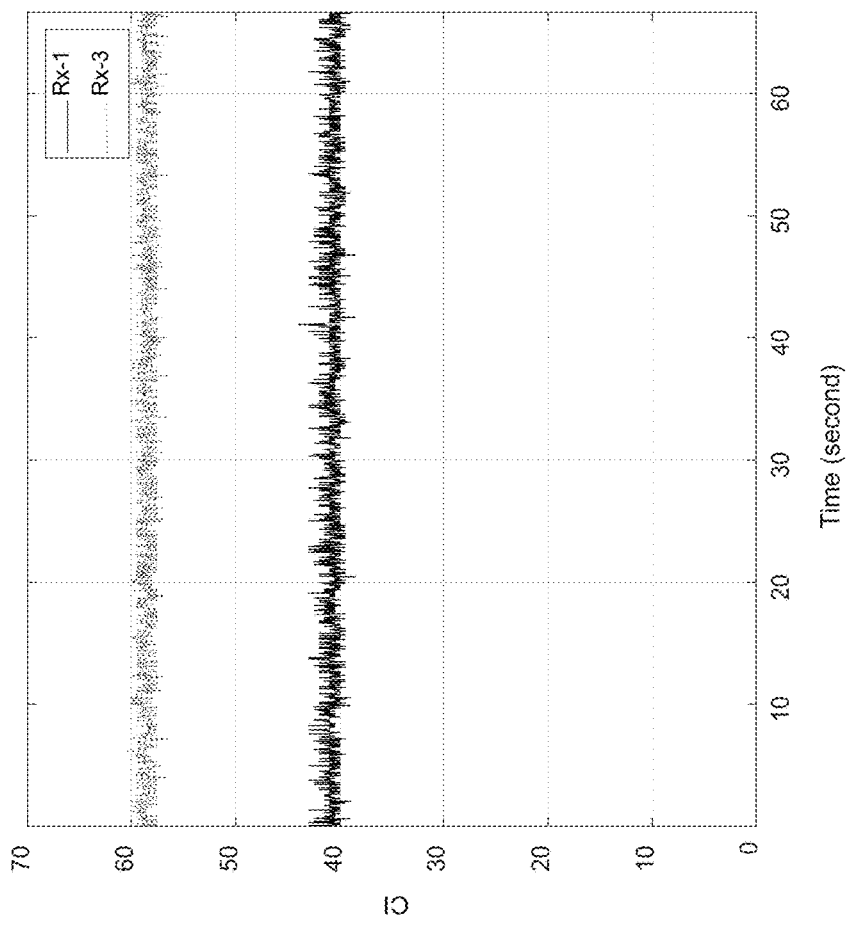
Figure 20C:
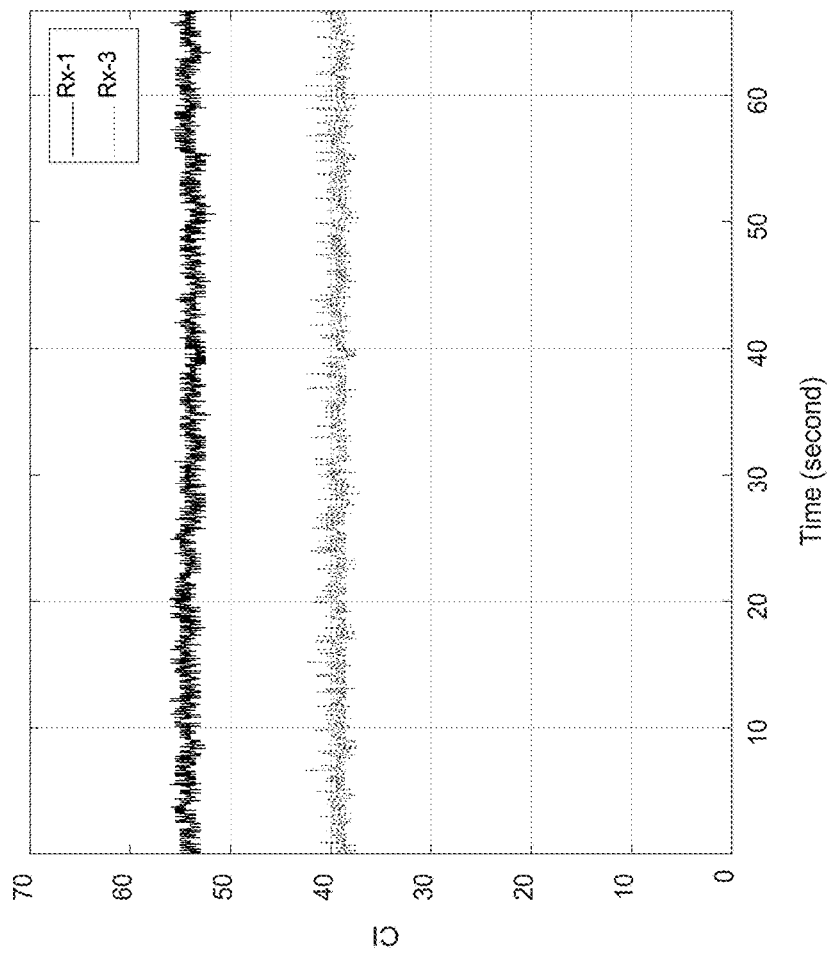
Figure 20D:
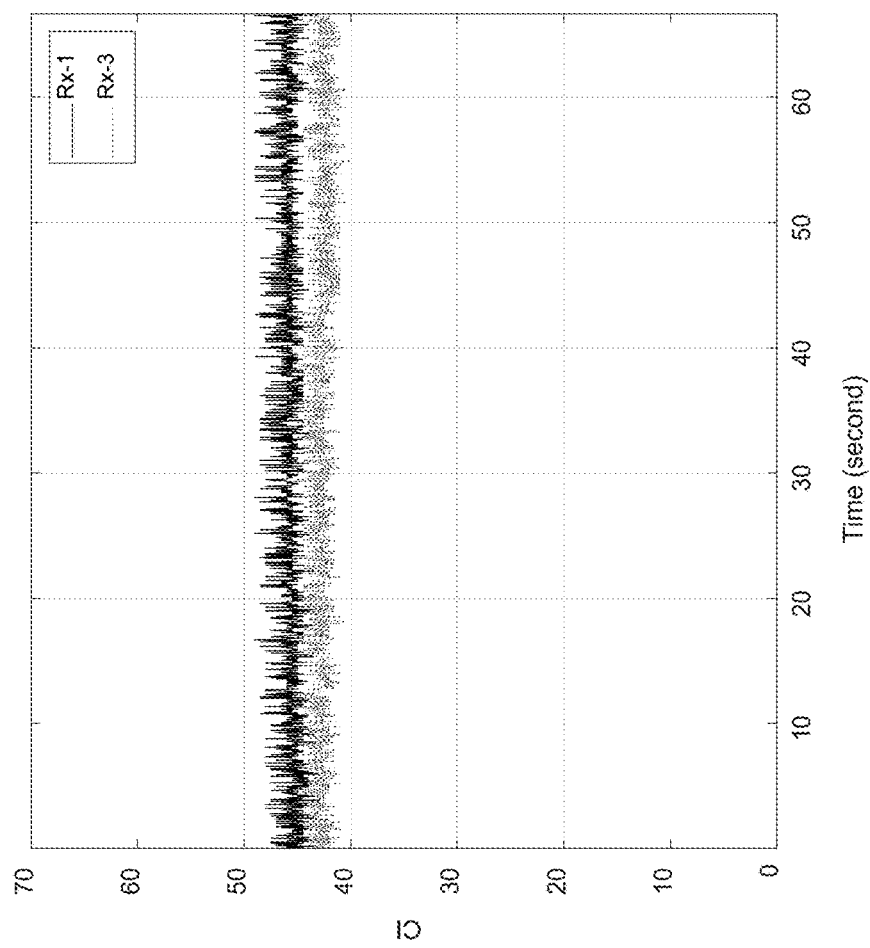

FIGS. 20A-20D illustrate changes of channel information (CI) according to various seat occupancy situations in a car, according to one embodiment of the present teaching. FIG. 20A shows CI when no seat is occupied. FIG. 20B shows CI when seat 1 (e.g. seat with Bot antenna 1 in FIG. 19) is occupied. FIG. 20C shows CI when seat 3 (e.g. seat with Bot antenna 3 in FIG. 19) is occupied. FIG. 20D shows CI when both seat 1 and seat 3 are occupied.

The features described above may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that may be used, directly or indirectly, in a computer to perform a certain activity or bring about a certain result. A computer program may be written in any form of programming language (e.g., C, Java), including compiled or interpreted languages, and it may be deployed in any form, including as a stand-alone program or as a module, component, subroutine, a browser-based web application, or other unit suitable for use in a computing environment.

Suitable processors for the execution of a program of instructions include, e.g., both general and special purpose microprocessors, digital signal processors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory may be supplemented by, or incorporated in, ASICs (application-specific integrated circuits).

While the present teaching contains many specific implementation details, these should not be construed as limitations on the scope of the present teaching or of what may be claimed, but rather as descriptions of features specific to particular embodiments of the present teaching. Certain features that are described in this specification in the context of separate embodiments may also be implemented in combination in a single embodiment. Conversely, various features that are described in the context of a single embodiment may also be implemented in multiple embodiments separately or in any suitable sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

Particular embodiments of the subject matter have been described. Any combination of the features and architectures described above is intended to be within the scope of the following claims. Other embodiments are also within the scope of the following claims. In some cases, the actions recited in the claims may be performed in a different order and still achieve desirable results. In addition, the processes depicted in the accompanying figures do not necessarily require the particular order shown, or sequential order, to achieve desirable results. In certain implementations, multitasking and parallel processing may be advantageous.

We claim:

1. A method implemented on a machine having a processor, a memory communicatively coupled with the processor and a set of instructions stored in the memory for recognizing an event, comprising:
   for each of at least one known event happening in a venue in a respective training time period:
      transmitting, by an antenna of a first transmitter, a respective training wireless signal to at least one first receiver through a wireless multipath channel impacted by the known event in the venue in the training time period associated with the known event,
      obtaining, asynchronously by each of the at least one first receiver based on the training wireless signal, at least one time series of training channel information (training CI time series) of the wireless multipath channel between the first receiver and the first transmitter in the training time period associated with the known event, and
      pre-processing the at least one training CI time series;
   training a projection for CI using a dimension reduction method based on the training CI time series associated with the at least one known event,
   training at least one classifier for the at least one known event based on the at least one training CI time series and the projection; and
   for a current event happening in the venue in a current time period,
      transmitting, by an antenna of a second transmitter, a current wireless signal to at least one second receiver through the wireless multipath channel impacted by the current event in the venue in the current time period associated with the current event,
      obtaining, asynchronously by each of the at least one second receiver based on the current wireless signal, at least one time series of current channel information (current CI time series) of the wireless multipath channel between the second receiver and the second transmitter in the current time period associated with the current event,
      pre-processing the at least one current CI time series, and
      applying the at least one classifier to:
         classify, based on the projection, at least one of: the at least one current CI time series, a portion of a particular current CI time series, and a combination of the portion of the particular current CI time series and a portion of an additional CI time series, and
         associate the current event with at least one of: a known event, an unknown event and another event,
   wherein a training CI time series associated with a first receiver and a current CI time series associated with a second receiver have at least one of:
      different starting times,
      different time durations,
      different stopping times,
      different counts of items in their respective time series,
      different sampling frequencies,
      different sampling periods between two consecutive items in their respective time series, and
      channel information (CI) with different features.

2. The method of claim 1, further comprising:
   aligning a first section of a first time duration of a first CI time series and a second section of a second time duration of a second CI time series, and
   determining a mapping between items of the first section and items of the second section.

3. The method of claim 2, wherein:
   the first CI time series is processed by a first operation;
   the second CI time series is processed by a second operation; and
   at least one of the first operation and the second operation comprises at least one of: subsampling, re-sampling, interpolation, filtering, transformation, feature extraction, and pre-processing.

4. The method of claim 2, further comprising mapping a first item of the first section to a second item of the second section, wherein at least one constraint is applied on at least one function of at least one of:
   the first item of the first section of the first CI time series;
   another item of the first CI time series;

a time stamp of the first item;
a time difference of the first item;
a time differential of the first item;
a neighboring time stamp of the first item;
another time stamp associated with the first item;
the second item of the second section of the second CI time series; another item of the second CI time series;
a time stamp of the second item;
a time difference of the second item;
a time differential of the second item;
a neighboring time stamp of the second item; and
another time stamp associated with the second item.

5. The method of claim 4, wherein one of the at least one constraint is that a difference between the time stamp of the first item and the time stamp of the second item is upper-bounded by an adaptive upper threshold and lower-bounded by an adaptive lower threshold.

6. The method of claim 1, further comprising:
determining a section of a time duration of a CI time series adaptively; and
determining a starting time and an ending time of the section, wherein determining the section comprises:
computing a tentative section of the CI time series, and
determining the section by removing a beginning portion and an ending portion of the tentative section.

7. The method of claim 6, wherein determining the section further comprises:
determining the beginning portion of the tentative section by:
considering items of the tentative section with increasing time stamp as a current item iteratively, one item at a time,
computing recursively an activity measure associated with at least one of:
the current item associated with a current time stamp,
past items of the tentative section with time stamps not larger than the current time stamp, and
future items of the tentative section with time stamps not smaller than the current time stamp,
adding the current item to the beginning portion of the tentative section when a first criterion associated with the activity measure is satisfied; and
determining the ending portion of the tentative section by:
considering items of the tentative section with decreasing time stamp as a current item iteratively, one item at a time,
iteratively computing and determining at least one activity measure associated with at least one of:
the current item associated with a current time stamp,
past items of the tentative section with time stamps not larger than the current time stamp, and
future items of the tentative section with time stamps not smaller than the current time stamp,
adding the current item to the ending portion of the tentative section when a second criterion associated with the at least one activity measure is satisfied.

8. The method of claim 7, wherein:
at least one of the first criterion and the second criterion comprises at least one of:
the activity measure is smaller than an adaptive upper threshold,
the activity measure is larger than an adaptive lower threshold,
the activity measure is smaller than an adaptive upper threshold consecutively for at least a predetermined amount of consecutive time stamps,
the activity measure is larger than an adaptive lower threshold consecutively for at least an additional predetermined amount of consecutive time stamps,
the activity measure is smaller than an adaptive upper threshold consecutively for at least a predetermined percentage of the predetermined amount of consecutive time stamps,
the activity measure is larger than an adaptive lower threshold consecutively for at least another predetermined percentage of the additional predetermined amount of consecutive time stamps,
another activity measure associated with another time stamp associated with the current time stamp is smaller than another adaptive upper threshold and larger than another adaptive lower threshold,
at least one activity measure associated with at least one respective time stamp associated with the current time stamp is smaller than respective upper threshold and larger than respective lower threshold, and
a percentage of time stamps with associated activity measure smaller than respective upper threshold and larger than respective lower threshold in a set of time stamps associated with the current time stamp exceeds a threshold; and
the activity measure associated with an item at time T1 comprises at least one of:
a first function of the item at time T1 and an item at time T1−D1, wherein D1 is a pre-determined positive quantity,
a second function of the item at time T1 and an item at time T1+D1,
a third function of the item at time T1 and an item at time T2, wherein T2 is a pre-determined quantity, and
a fourth function of the item at time T1 and another item.

9. The method of claim 8, wherein:
at least one of: the first function, the second function, the third function, and the fourth function, is at least one of:
a function F1(x, y, . . . ) with at least two scalar arguments: x and y,
a function F2(X, Y, . . . ) with at least two vector arguments: X and Y,
and a function F3(X1, Y1, . . . ) with at least two arguments: X1 and Y1;
the function F1 is a function of at least one of the following: x, y, (x−y), (y−x), abs(x−y), x^a1, y^b1, abs(x^a1−y^b1), (x−y)^a1, (x/y), (x+a1)/(y+b1), (x^a1/y^b1), and ((x/y)^a1−b1), wherein a1 and b1 are pre-determined quantities;
both X and Y are n-tuples such that X=(x_1, x_2, . . . , x_n) and Y=(y_1, y_2, . . . , y_n); the function F2 is a function of at least one of the following: x_i, y_i, (x_i−y_i), (y_i−x_i), abs(x_i−y_i), x_i ^a2, y_i ^b2, abs(x_i^a2−y_i ^b2), (x_i−y_i)^a2, (x_i/y_i), (x_i+a2)/(y_i+b2), (x_i ^a2/y_i ^b2), and ((x_i/y_i)^a2−b2);
i, ranging from 1 to n, is a component index of the n-tuples X and Y;
both X1 and Y1 are n-tuples comprising N components such that X1=(x1_1, x1_2, . . . , x1_N) and Y1=(y1_1, y1_2, . . . , y1_N);
the function F3 comprises a component-by-component summation of another function of at least one of the following: x1_j, y1_j, (x1_j−y1_j), (y1_j−x1_j), abs ($x1\_j-y1\_j$), $x1\_j\hat{\ }a3$, $y1\_j\hat{\ }b3$, $abs(x1\_j\hat{\ }a3-y1\_j\hat{\ }b3)$, ($x1\_j-y1\_j)\hat{\ }a3$, ($x1\_j/y1\_j$), ($x1\_j+a3$)/($y1\_j+b3$), ($x1\_j\hat{\ }a3/y1\_j\hat{\ }b3$), and (($x1\_j/y1\_j)\hat{\ }a3-b3$); and j, ranging from 1 to N, is a component index of the n-tuples X1 and Y1.

10. The method of claim 2, further comprising computing the mapping using dynamic time warping (DTW), wherein the DTW comprises a constraint on at least one of: the mapping, the items of the first CI time series, the items of the second CI time series, the first time duration, the second time duration, the first section, and the second section.

11. The method of claim 1, further comprising:
aligning a first section of a first time duration of a first CI time series and a second section of a second time duration of a second CI time series;
computing a map comprising a plurality of links between first items of the first section and second items of the second section, wherein each of the plurality of links associates a first item with a first time stamp with a second item with a second time stamp;
computing a mismatch cost between the aligned first section and the aligned second section;
applying the at least one classifier based on the mismatch cost, wherein:
the mismatch cost comprises at least one of: an inner product, an inner-product-like quantity, a quantity based on correlation, a quantity based on covariance, a discriminating score, a distance, a Euclidean distance, an absolute distance, an L_1 distance, an L_2 distance, an L_k distance, a weighted distance, a distance-like quantity and another similarity value, between the first vector and the second vector, and a function of: an item-wise cost between a first item of the first section of the first CI time series and a second item of the second section of the second CI time series associated with the first item by a link of the map, and a link-wise cost associated with the link of the map,
the aligned first section and the aligned second section are represented respectively as a first vector and a second vector that have a same vector length, and
the mismatch cost is normalized by the same vector length.

12. The method of claim 11, further comprising:
applying the at least one classifier to a plurality of first sections of the first CI time series and a plurality of respective second sections of the second CI time series;
obtaining at least one tentative classification result, each tentative classification result being associated with a respective first section and a respective second section; and
associating the current event with at least one of: the known event, the unknown event and the another event, based on a largest number of the at least one tentative classification result associated with at least one of: the known event, the unknown event and the another event.

13. The method of claim 1,
wherein the dimension reduction method comprises at least one of: principal component analysis (PCA), PCA with different kernel, independent component analysis (ICA), Fisher linear discriminant, vector quantization, supervised learning, unsupervised learning, self-organizing maps, auto-encoder, neural network, and deep neural network.

14. The method of claim 1, further comprising:
re-training the projection using at least one of: the dimension reduction method, and an additional dimension reduction method, based on at least one of: the projection before the re-training, the training CI time series, at least one current CI time series obtained as of the re-training of the projection, and additional training CI time series, wherein the additional dimension reduction method comprises at least one of: a simplified dimension reduction method, principal component analysis (PCA), PCA with different kernels, independent component analysis (ICA), Fisher linear discriminant, vector quantization, supervised learning, unsupervised learning, self-organizing maps, auto-encoder, neural network, and deep neural network;
re-training the at least one classifier based on at least one of: the re-trained projection, the training CI time series associated with the at least one known event, and the at least one current CI time series; and
classifying the at least one current CI time series based on the re-trained projection, the re-trained classifier, and the at least one current CI time series.

15. The method of claim 1, further comprising:
for at least one first section of a first time duration of the current CI time series:
for each of the at least one known event:
determining a respective second section of a respective second time duration of a respective representative training CI time series of the respective event,
aligning the first section and the respective second section, and
computing a mismatch cost between the aligned first section and the aligned respective second section,
applying the at least one classifier, and
obtaining a tentative classification result based on the mismatch costs; and
associating the at least one first section with at least one of: the at least one known event, an unknown event and the another event, based on the at least one tentative classification result.

16. The method of claim 15, further comprising:
computing how many times each known event achieves a smallest mismatch cost; and
associating the at least one first section with at least one of:
a known event that achieves the smallest mismatch cost for most times,
a known event that achieves a smallest overall mismatch cost, wherein an overall mismatch cost is a weighted average of at least one mismatch cost associated with the at least one first section,
a known event that achieves a smallest cost based on another overall cost,
and an unknown event,
wherein the at least one first section is associated with the unknown event in at least one of the following situations:
no event achieves a mismatch cost lower than a first threshold T1 in a sufficient percentage of the at least one first section, and
no event achieves an overall mismatch cost lower than a second threshold T2.

17. The method of claim 15, wherein the representative training CI time series associated with the known event is obtained based on the at least one training CI time series associated with the known event.

18. The method of claim 17, wherein:
the representative training CI time series associated with the known event is a particular one of the at least one training CI time series associated with the known event such that it has a smallest aggregate mismatch among the at least one training CI time series;

the aggregate mismatch of a particular training CI time series is a function of at least one mismatch cost between the particular training CI time series and each of the remaining of the at least one training CI time series aligned with the particular training CI time series;

the function comprises at least one of: average, weighed average, mean, trimmed mean, median, mode, arithmetic mean, geometric mean, harmonic mean, truncated mean, generalized mean, power mean, f-mean, interquartile mean, and another mean.

19. The method of claim 17, wherein:

a particular representative training CI time series associated with a particular known event has a particular time duration;

the particular representative training CI time series of the particular time duration is aligned with each of the at least one training CI time series associated with the known event and a respective mismatch cost is computed;

the particular representative training CI time series minimizes an aggregate mismatch with respect to the at least one training CI time series;

the aggregate mismatch of a CI time series is a function of at least one mismatch cost between the CI time series and each of the at least one training CI time series aligned with the CI time series; and the function comprises at least one of: average, weighed average, mean, trimmed mean, median, mode, arithmetic mean, geometric mean, harmonic mean, truncated mean, generalized mean, power mean, f-mean, interquartile mean, and another mean.

20. The method of claim 19, wherein:

the particular time duration minimizes the aggregate mismatch among a plurality of candidate time durations of the particular representative training CI time series;

the particular time duration and the particular representative training CI time series with the particular time duration are computed iteratively;

a current time duration is initialized as one of the plurality of candidate time durations;

for the current time duration, a current optimal trained representative CI time series with the current time duration is computed; and for the current optimal trained representative CI time series, the current time duration is changed to give a smaller normalized aggregate mismatch.

21. A system having a processor, a memory communicatively coupled with the processor and a set of instructions stored in the memory for recognizing an event, comprising:

a first transmitter in a venue and configured for:
  for each of at least one known event happening in the venue in a respective training time period, transmitting a respective training wireless signal through a wireless multipath channel impacted by the known event in the venue in the training time period associated with the known event;

at least one first receiver in the venue, wherein each of the at least one first receiver is configured for:
  for each of the at least one known event happening in the venue,
    receiving asynchronously the respective training wireless signal through the wireless multipath channel,
    obtaining, asynchronously based on the respective training wireless signal, at least one time series of training channel information (training CI time series) of the wireless multipath channel between the first receiver and the first transmitter in the training time period associated with the known event, and
    pre-processing the at least one training CI time series;

a second transmitter in the venue and configured for:
  for a current event happening in the venue in a current time period, transmitting a current wireless signal through the wireless multipath channel impacted by the current event in the venue in the current time period associated with the current event;

at least one second receiver in the venue, wherein each of the at least one second receiver is configured for:
  for the current event happening in the venue in the current time period,
    receiving asynchronously the current wireless signal through the wireless multipath channel,
    obtaining, asynchronously based on the current wireless signal, at least one time series of current channel information (current CI time series) of the wireless multipath channel between the second receiver and the second transmitter in the current time period associated with the current event, and
    pre-processing the at least one current CI time series; and an event recognition engine configured for:
  training a projection for CI using a dimension reduction method based on the training CI time series associated with the at least one known event,
  training at least one classifier for the at least one known event based on the at least one training CI time series and the projection,
  applying the at least one classifier to:
    classify, based on the projection, at least one of: the at least one current CI time series, a portion of a particular current CI time series, and a combination of the portion of the particular current CI time series and a portion of an additional CI time series, and
    associate the current event with at least one of: a known event, an unknown event and another event, wherein a training CI time series associated with a first receiver and a current CI time series associated with a second receiver have at least one of:
      different starting times,
      different time durations,
      different stopping times,
      different counts of items in their respective time series,
      different sampling frequencies,
      different sampling periods between two consecutive items in their respective time series, and
      channel information (CI) with different features.

22. The system of claim 21, wherein the event recognition engine is further configured for:

aligning a first section of a first time duration of a first CI time series and a second section of a second time duration of a second CI time series; and determining a mapping between items of the first section and items of the second section.

23. The system of claim 22, wherein:
the first CI time series is processed by a first operation;
the second CI time series is processed by a second operation; and
at least one of the first operation and the second operation comprises at least one of: subsampling, re-sampling, interpolation, filtering, transformation, feature extraction, and pre-processing.

24. The system of claim 22, wherein the event recognition engine is further configured for:
mapping a first item of the first section to a second item of the second section; and
applying at least one constraint on at least one function of at least one of:
the first item of the first section of the first CI time series;
another item of the first CI time series;
a time stamp of the first item;
a time difference of the first item;
a time differential of the first item;
a neighboring time stamp of the first item;
another time stamp associated with the first item;
the second item of the second section of the second CI time series;
another item of the second CI time series;
a time stamp of the second item;
a time difference of the second item;
a time differential of the second item;
a neighboring time stamp of the second item; and
another time stamp associated with the second item,
wherein one of the at least one constraint is that a difference between the time stamp of the first item and the time stamp of the second item is upper-bounded by an adaptive upper threshold and lower-bounded by an adaptive lower threshold.

25. The system of claim 21, wherein the event recognition engine is further configured for:
determining a section of a time duration of a CI time series adaptively; and
determining a starting time and an ending time of the section, wherein determining the section comprises:
computing a tentative section of the CI time series, and
determining the section by removing a beginning portion and an ending portion of the tentative section.

26. The system of claim 21, wherein:
at least one of: the current event and the at least one known event is related to security;
the event recognition engine is coupled to at least one of: the first transmitter, the second transmitter, an additional transmitter, the at least one first receiver, the at least one second receiver, an additional receiver, a cloud server, a fog server, a local server, and an edge server;
the first transmitter and the second transmitter are at a same location in the venue; and
at least one of: a subset of the at least one first receiver is a permutation of a subset of the at least one second receiver.

27. An event recognition engine of a wireless monitoring system, comprising:
a processor;
a memory communicatively coupled with the processor; and
a set of instructions stored in the memory which, when executed, causes the processor to perform:
for each of at least one known event happening in a venue in a respective training time period, obtaining, from each of at least one first receiver in the venue, at least one time series of training channel information (training CI time series) of a wireless multipath channel impacted by the known event, wherein the first receiver extracts the training CI time series from a respective training wireless signal received from a first transmitter in the venue through the wireless multipath channel between the first receiver and the first transmitter in the training time period associated with the known event,
training a projection for CI using a dimension reduction method based on the training CI time series associated with the at least one known event,
training at least one classifier for the at least one known event based on the at least one training CI time series and the projection,
for a current event happening in the venue in a current time period:
obtaining, from each of at least one second receiver in the venue, at least one time series of current channel information (current CI time series) of the wireless multipath channel impacted by the current event, wherein the second receiver extracts the current CI time series from a current wireless signal received from a second transmitter in the venue through the wireless multipath channel between the second receiver and the second transmitter in the current time period associated with the current event,
applying the at least one classifier to:
classify, based on the projection, at least one of: the at least one current CI time series, a portion of a particular current CI time series, and a combination of the portion of the particular current CI time series and a portion of an additional CI time series, and
associate the current event with at least one of: a known event, an unknown event and another event, wherein a training CI time series associated with a first receiver and a current CI time series associated with a second receiver have at least one of:
different starting times,
different time durations,
different stopping times,
different counts of items in their respective time series,
different sampling frequencies,
different sampling periods between two consecutive items in their respective time series, and
channel information (CI) with different features.

28. The event recognition engine of claim 27, wherein the set of instructions stored in the memory, when executed, further causes the processor to perform:
aligning a first section of a first time duration of a first CI time series and a second section of a second time duration of a second CI time series; and
determining a mapping between items of the first section and items of the second section, wherein:
the first CI time series is processed by a first operation,
the second CI time series is processed by a second operation, and
at least one of the first operation and the second operation comprises at least one of: subsampling, re-sampling, interpolation, filtering, transformation, feature extraction, and pre-processing.

29. The event recognition engine of claim 27, wherein the set of instructions stored in the memory, when executed, further causes the processor to perform:
- determining a section of a time duration of a CI time series adaptively; and
- determining a starting time and an ending time of the section, wherein determining the section comprises: computing a tentative section of the CI time series, and determining the section by removing a beginning portion and an ending portion of the tentative section.

30. A receiver of a wireless monitoring system, comprising:
- a wireless circuitry configured to:
  - for each of at least one known event happening in a venue in a respective training time period, receive a respective training wireless signal through a wireless multipath channel impacted by the known event, wherein the respective training wireless signal is transmitted by a first transmitter through the wireless multipath channel between the receiver and the first transmitter in the training time period associated with the known event, and
  - for a current event happening in the venue in a current time period, receive a current wireless signal through the wireless multipath channel impacted by the current event, wherein the current wireless signal is transmitted by a second transmitter through the wireless multipath channel between the receiver and the second transmitter in the current time period associated with the current event;
- a processor communicatively coupled with the wireless circuitry;
- a memory communicatively coupled with the processor; and
- a set of instructions stored in the memory which, when executed, causes the processor to:
  - for each of the at least one known event happening in the venue, obtain, asynchronously based on the respective training wireless signal, at least one time series of training channel information (training CI time series) of the wireless multipath channel, and
  - for the current event happening in the venue in the current time period, obtain, asynchronously based on the current wireless signal, at least one time series of current channel information (current CI time series) of the wireless multipath channel, wherein:
    - a projection for the CI is trained using a dimension reduction method based on the training CI time series associated with the at least one known event,
    - the at least one training CI time series is used by an event recognition engine of the wireless monitoring system to train at least one classifier for the at least one known event based on the projection, and
    - the at least one classifier is applied to:
      - classify, based on the projection, at least one of: the at least one current CI time series, a portion of a particular current CI time series, and a combination of the portion of the particular current CI time series and a portion of an additional CI time series, and
      - associate the current event with at least one of: a known event, an unknown event and another event.

* * * * *